(12) United States Patent
Shen et al.

(10) Patent No.: US 7,416,870 B2
(45) Date of Patent: Aug. 26, 2008

(54) METHODS OF DIRECTING C-O BOND FORMATION UTILIZING A TYPE II POLYKETIDE SYNTHASE SYSTEM

(75) Inventors: Ben Shen, Verona, WI (US); Hyung-Jin Kwon, Austin, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 501 days.

(21) Appl. No.: 10/646,664

(22) Filed: Aug. 22, 2003

(65) Prior Publication Data

US 2004/0241799 A1 Dec. 2, 2004

Related U.S. Application Data

(60) Provisional application No. 60/405,245, filed on Aug. 22, 2002.

(51) Int. Cl.
*C12N 9/02* (2006.01)
*C07H 21/04* (2006.01)

(52) U.S. Cl. .................. 435/189; 435/69.1; 435/320.1; 435/325; 536/23.2

(58) Field of Classification Search ................ 435/69.1, 435/189, 320.1, 325; 536/23.2
See application file for complete search history.

(56) References Cited

OTHER PUBLICATIONS

Bao, W.; Sheldon, P. J., Hutchinson, C. R. Biochemistry 1999, 38, 9752.
Bao W.; Wendt-Pienkowski, E.; Hutchinson, C.R. Biochemistry 1998, 37, 8132.
Bibb, M.J.; Findlay, P.R.; Johnson, M.W. Gene 1984, 30, 157.
Birch, A.W.; Robinson, J. A. In Genetics and Biochemistry of Antibiotic Production; 1995; pp. 443-476; Vining, L. C., Stuttard, C., Eds.; Butterworth-Heinermann: Boston.
Callewaert, D. M.; Radcliff, G.; Tanouchi, T.; Schichi, H. Immunopharmacology 1988, 16, 25.
Carreras, C. W.; Kholsa, C. Biochemistry 1998, 37, 2084.
Choi, K. H.; Kremer, L.; Besra, G. S.; Rock, C. O. J. Biol. Chem. 2000, 275, 28201.
Dreier, J.; Shah, A. N.; Kholsa, C. J. Biol. Chem. 1999, 274, 25108.
Fleck, W. F.; Ritzau M.; Heinze, S.; Grafe, U. J. Basic Micrbiol. 1996, 36, 235.
Funa, N.; Ohnishi, Y.; Fujii, I.; Shibuya, M.; Ebizuka, Y.; Horinouchi, S. Nature1999, 400, 897.
Ishikawa, J.; Hotta, K. Fems Microbiol. Lett. 1999, 174, 251.
Jez, J. M.; Bowman, M. E.; Dixon, R. A.; Noel, J. P. Nat. Struct. Biol. 2000, 7, 786.
Kwon, H. J.; Smith, W. C.; Scharon, A. J.; Hwang, S. H.; Kurth, M. J.; Shen, B. Science 2002, 297, 1327-1330.
Kwon, H. J.; Smith, W. C.; Xiang, L.; Shen, B. J.; Am Chem. Soc. 2001, 123, 3385.
Meadows, E. S.; Khosla, C. Biochemistry 2001, 40, 14855.
Mori, A.; Kaminuma, O.; Ogawa, K.; Nakata, A.; Egan, R. W.; Akiyama, K.; Okudaria, H. J. Allergy Clin. Immunol. 2000, 106, S58.
Mori, A.; Okudaria, H.; Kobayashi, N.; Akiyama, K. Int. Arch. Allergy Immunol. 2001, 124, 172.
Plater, R.; Robinson, J. A. Gene1992, 112, 117.
Smith, W.; Xiang, L.; Shen, B. Antimicrob. Agents Chemother. 2000, 44, 1809.
Stahl, P.; Pape, H. Arch. Mikrobiol. 1972, 85, 239.
Summers, R. G.; Ali, A.; Shen, B.; Wessel, W. A.; Hutchinson, C. R. Biochemistry 1995, 34, 9389.
Trueba, G.; Bolin, C.; Zuerner, R., Gene 1995, 160, 133.
Tanouchi, Y.; Shichi, H. Immunology 1988, 63, 471.
Teunissen, M. B. M.; Pistoor, F. H. M.; Rongen, H. A. H.; Kapsenberg, M. L.; BOS, J. D. Transplantation1992, 53, 875.
Walczak, R.J.; Woo, A. J.; Strohl, W. R.; Priestley, N. D. FEMS Microbiol. Lett. 2000, 183, 171.
Wang, Y.; Metz, P. Tetrahedron: Asymmetry 2000, 11, 3995.
Watanbe, C. M. H.; Townsend, C. A. Chem. Biol. 2002, 9, 981.
Wohlert, S. E.; Lomovskaya, N.; Kulowski, K.; Fonstein, L.; OCCI, J. L.; Gewain, K. M.; Mac Neil, D. J.; Hutchinson, C. R. Chem. Biol. 2001, 108, 1.
Woo, A. J.; Strohl, W. R.; Priestley, N. D. Antimicrob. Agents Chemother.1999, 43, 1662.
Zawada, R. J. X.; Khosla, C. Chem. Biol. 1999, 6, 607.

*Primary Examiner*—Chih-Min Kam
(74) *Attorney, Agent, or Firm*—Fulbright & Jaworski, LLP

(57) ABSTRACT

The present invention provides methods of modifying a biological molecule by C—O bond formation utilizing a type II polyketide synthase (PKS) system from the nonactin biosynthesis gene cluster. The type II PKS responsible for biosynthesis of the macrotetralide nonactin includes polypeptides encoded by the nonJK genes. The NonJ and NonK polypeptides have been identified by the inventors as ketoacyl synthases capable of directly catalyzing C—O bond formation between substrate molecules. This invention increases the scope and diversity of chemical syntheses available for drug design and combinatorial biosynthesis.

23 Claims, 16 Drawing Sheets

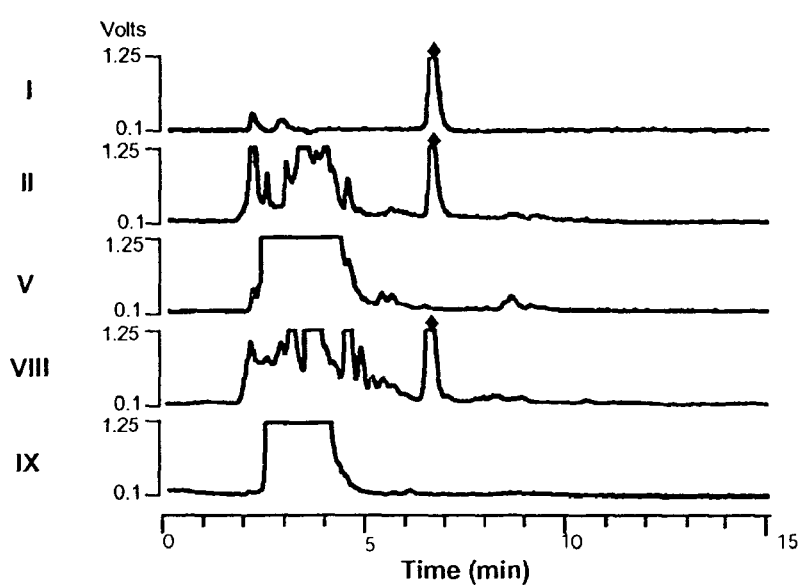
Figure 6

| | | | | | |
|---|---|---|---|---|---|
| Type II-FAS | FabB | ISSACATSA | -126aa- | YLNSHGTST | -24aa- | TKAMCHSLGA |
| | FabF | IATACTSGV | -131aa- | YVNAHGTGT | -26aa- | TKSMCHLLGA |
| Type I-PKS | DEBS1 | VDTACSSSL | -126aa- | AVEAHGTGT | -27aa- | VKSNLGHTQAA |
| Type I-PKS | PikAIV | VDTACSSSL | -126aa- | VVEGHGTGT | -29aa- | LKSNIGHGTGT |
| Type II-PKS | Act KSα | VSTGCTSGL | -131aa- | YINAHGSGT | -26aa- | TKSMVCHSLGA |
| | Tcm KSα | VSTGCTSGL | -131aa- | YINAHGSGT | -26aa- | LKSMICHSLGA |
| Type III-PKS | CHS2 | YQQGCFAGG | -130aa- | FWIAHPGGP | -22aa- | VLSDYGNMSSA |
| | RppA | AQLGCAAGG | -123aa- | FFIVHAGGP | -22aa- | TLTERGNIASS |
| | NonK | VSCGCASSS | -143aa- | YVNGGGEGD | -26aa- | QEACFGHSGAP |
| | NonJ | VSGSCNVAL | -122aa- | FVNDYADGN | -28aa- | QEAVFGHVAGT |

Figure 8

METHODS OF DIRECTING C-O BOND FORMATION UTILIZING A TYPE II POLYKETIDE SYNTHASE SYSTEM

RELATED APPLICATIONS

This application claims the benefit of U.S. Provisional Application No. 60/405,245 filed on Aug. 22, 2002, which is incorporated herein by reference in its entirety for all purposes.

STATEMENT AS TO RIGHTS TO INVENTIONS MADE UNDER FEDERALLY SPONSORED RESEARCH AND DEVELOPMENT

This invention was made with government support under grant MCB-0196528 awarded by the National Science Foundation. The government has certain rights in the invention.

FIELD OF THE INVENTION

This invention relates to the field of polyketide biosynthesis. In particular, this invention is directed to methods of using polyketide synthases and components thereof capable of catalyzing C—O bonds.

BACKGROUND OF THE INVENTION

Polyketides are a large family of structurally diverse natural products found in bacteria, fungi, and plants. Many polyketides are clinically important drugs such as erythromycin and tetracycline (antibacterial), daunorubicin and epothilone (anticancer), FK-506 and rapamycin (immunosuppresant), and lovastatin (antihypercholesterolemic). Despite their apparent structural diversity, polyketides share a common mechanism of biosynthesis. The carbon backbone of a polyketide results from sequential condensation of acyl coenzyme (CoA) precursors, and this process, in a mechanistic analogy to fatty acid biosynthesis by the fatty acid synthases (FASs), is catalyzed by the polyketide synthases (PKSs). Much of the current research on polyketide biosynthesis is driven by the following two factors: (1) the extraordinary structure, mechanism, and catalytic reactivity of PKSs that provide an unprecedented opportunity to investigate the molecular mechanism of enzyme catalysis, molecular recognition, and protein-protein interaction and (2) the remarkable flexibility and plasticity of PKSs that allow the production of novel compounds that are difficult to access by traditional chemical synthesis.

The success of the biosynthetic approach depends critically on the availability of novel genetic systems and on genes encoding novel enzyme activities. Of the various polyketide pathways currently being examined, the macrotetrolides, of polyketide origin, offer a distinct opportunity to study the biosynthesis of unique molecular scaffolds. Understanding the mechanisms underlying macrotetrolide production will provide access to rational engineering of macrotetrolide analogues for novel drug leads and also facilitate construction of improved macrotetrolide expression strains by altering specific components of the biosynthetic machinery. In addition, and more importantly, elucidation of the molecular mechanisms of macrotetrolide biosynthesis contribute to the general field of combinatorial biosynthesis by expanding the repertoire of novel PKSs available for use in combinatorial biosynthesis schemes. Consequently, identifying novel PKS mechanisms will further expand the size and diversity of chemical libraries accessible by combinatorial biosynthesis.

SUMMARY OF THE INVENTION

In general, the present invention provides methods of modifying biological molecules based on the C—O bond forming activities of polypeptides derived from or related to a type II polyketide synthase (PKS) system capable of C—O bond formation. In particular, the inventors have recently identified the unique C—O bond forming activity of NonJ and NonK, two ketoacyl synthases present within the type II PKS responsible for biosynthesis of the macrotetralide nonactin. NonJ and NonK are unique in their ability to act directly on acyl-CoA intermediates in catalyzing C—O bond formation. Based on the related disclosure provided herein, one of skill in the art will realize many practical and useful advantages provided by the present invention. The amino acid sequences for NonJ and NonK are set forth in SEQ ID NOS. 3 and 5, respectively. As well, nucleic acid sequences encoding NonJ and NonK are provided in SEQ ID NOS. 2 and 4, respectively. SEQ ID NO. 1 sets forth a partial nucleic acid sequence of the nonactin biosynthesis gene cluster including both nonJ and nonK genes.

In certain embodiments, the invention provides methods including steps of contacting a biological molecule which is a substrate for a polypeptide selected from the group consisting of: (a) a polypeptide comprised by an amino acid sequence set forth in SEQ ID NO. 3; (b) a polypeptide encoded by a nucleic acid comprising nucleotide sequence set forth in SEQ ID NO. 2; and (c) a polypeptide encoded by a nucleic acid that specifically hybridizes under stringent conditions to SEQ ID NO. 2 and capable of C—O bond formation; with the polypeptide. The polypeptide then modifies the biological molecule by formation of a C—O bond.

In preferred embodiments, a method according to the invention includes the further step of contacting the biological molecule modified by the polypeptide described in the preceding paragraph with a second polypeptide selected from the group consisting of: (a) a polypeptide comprised by an amino acid sequence set forth in SEQ ID NO. 5; (b) a polypeptide encoded by a nucleic acid comprising nucleotide sequence set forth in SEQ ID NO. 4; and (c) a polypeptide encoded by a nucleic acid that specifically hybridizes under stringent conditions to SEQ ID NO. 4 and capable of C—O bond formation. The second polypeptide further modifies the biological molecule by formation of a C—O bond.

In particularly preferred embodiments, methods according to the invention facilitate C—O bond formation between the biological molecule and a second biological molecule, the second biological molecule also suitable as a substrate for the polypeptide.

In certain embodiments, the methods described and claimed herein are carried out in vivo, through the use of a host cell. Suitable host cells include bacterium as well as eukaryotic cells such as mammalian cells, yeast cells, plant cells, fungal cells, and insect cells. In alternate embodiments, the present invention may be practiced ex vivo. In yet other embodiments, at least one of the biological molecules utilized as substrate is exogenously supplied. As well, methods according to the invention preferably result in the production of a macrotetralide or a macrotetralide analogue.

In various embodiments, the invention encompasses yet additional methods of catalyzing a C—O bond between biological molecules. Such methods include steps of contacting biological molecules which are substrates for at least one polypeptide capable of catalyzing C—O bond formation between the biological molecules and encoded by a nucleic acid set forth in SEQ ID NO. 1 or a nucleic acid hybridizing under stringent conditions thereto, with the polypeptide. The polypeptide then catalyzes C—O bond formation between the biological molecules.

In preferred embodiments, the invention provides methods of producing a macrotetralide or a macrotetralide analogue. These methods include steps of contacting biological molecules that are substrates for at least one polypeptide selected from the group consisting of: (a) a polypeptide encoded by an amino acid sequence set forth in SEQ ID NO. 3 or 5; (b) a polypeptide encoded by a nucleic acid comprising a nucleotide sequence set forth in SEQ ID NO. 2 or 4; and (c) a polypeptide encoded by a nucleic acid that specifically hybridizes under stringent conditions to SEQ ID NO. 2 or 4 and capable of C—O bond formation; with the polypeptide under conditions such that the polypeptide catalyzes a C—O bond between the biological molecules. A macrotetralide or macrotetralide analogue is thereby synthesized and the macrotetralide or macrotetralide analogue is subsequently recovered.

In other embodiments, the invention is directed to methods of preparing a hybrid enzyme. Such methods include the step of positioning in a hybrid enzyme at least one catalytic domain capable of catalyzing C—O bond formation between biological molecules. The catalytic domain is encoded by a polypeptide selected from the group consisting of: (a) a polypeptide encoded by an amino acid sequence set forth in SEQ ID NO. 3 or 5; (b) a polypeptide encoded by a nucleic acid comprising nucleotide sequence set forth in SEQ ID NO. 2 or 4; (c) a polypeptide encoded by a nucleic acid that specifically hybridizes under stringent conditions to SEQ ID NO. 2 or 4 and capable of C—O bond formation.

In yet other embodiments, the invention provides methods of preparing a megasynthetase. These methods include the step of positioning in a megasynthetase at least one module including a polypeptide capable of catalyzing C—O bond formation between biological molecules. The polypeptide is selected from the group consisting of: (a) a polypeptide encoded by an amino acid sequence set forth in SEQ ID NO. 3 or 5; (b) a polypeptide encoded by a nucleic acid comprising nucleotide sequence set forth in SEQ ID NO. 2 or 4; and (c) a polypeptide encoded by a nucleic acid that specifically hybridizes under stringent conditions to SEQ ID NO. 2 or 4 and capable of C—O bond formation.

The present invention also includes methods of catalyzing C—O bond formation between biological molecules by NonJ and polypeptides derived there from. Methods according to the invention include steps of contacting biological molecules that are substrates for a polypeptide selected from the group consisting of: (a) a polypeptide comprised by an amino acid sequence set forth in SEQ ID NO. 3; (b) a polypeptide encoded by a nucleic acid comprising nucleotide sequence set forth in SEQ ID NO. 2; and (c) a polypeptide encoded by a nucleic acid that specifically hybridizes under stringent conditions to SEQ ID NO. 2 and capable of C—O bond formation; with the polypeptide whereby the polypeptide catalyzes C—O bond formation between the biological molecules.

In particular embodiments according to the invention, methods are provided for catalyzing C—O bond formation between biological molecules by NonK and polypeptides derived there from. Such methods include steps of contacting biological molecules that are substrates for a polypeptide selected from the group consisting of: (a) a polypeptide comprised by an amino acid sequence set forth in SEQ ID NO. 5; (b) a polypeptide encoded by a nucleic acid comprising nucleotide sequence set forth in SEQ ID NO. 4; and (c) a polypeptide encoded by a nucleic acid that specifically hybridizes under stringent conditions to SEQ ID NO. 4 and capable of C—O bond formation; with the polypeptide. The polypeptide then catalyzes C—O bond formation between the biological molecules.

In yet another embodiment, the present invention provides methods of chemically modifying a biological molecule by C—O bond formation. Generally, the method includes contacting a biological molecule that is a substrate for a polypeptide selected from the group consisting of: a polypeptide encoded by an amino acid sequence set forth in SEQ ID NO. 3 or 5; a polypeptide encoded by a nucleic acid comprising nucleotide sequence identical to or isolated from SEQ ID NO. 1, 2 or 4; a polypeptide encoded by a nucleic acid encoding an amino acid sequence set forth in SEQ ID NO. 3 or 5; and a polypeptide encoded by a nucleic acid that specifically hybridizes under stringent conditions to SEQ ID NO. 1, 2 or 4. The particular polypeptide chemically modifies the biological molecule by formation of a C—O bond. In another embodiment of the invention, the foregoing method effectuates a condensation between the biological molecule and a second biological molecule.

These and other applications and advantages of the present invention will become apparent from the detailed description accompanying the drawings.

BRIEF DESCRIPTION OF THE DRAWINGS

FIG. 6. (A) The macrotetrolide biosynthesis gene cluster with the five nonJKPQU KS genes shown in medium shading and the nonL CoA ligase gene shown in black. (B) Biotransformation of (±)-3 into 1 by *S. lividans* strains harboring various non gene expression cassettes. (Shown in black are genes cassettes constructed in pSET152 and shown in blue are gene cassettes constructed in pWHM3). Black rectangles with arrow indicate orientation of the actI promoters. Each entry represents an *S. lividans* strain transformed with either the pSET152 or pWHM3-based cassette or both and its biotransformation yield of 1 from 5 mg of (±)-3. The nonK C161G and nonJ C169G mutants are shown in. (C) Examples of HPLC chromatograms of biotransformation of (±)-3 into 1 by various *S. lividans* recombinant strains: I, authentic 1 standard (♦); II, *S. lividans* (pBS2014/pBS2015); V, *S. lividans* (pBS2017); VIII, *S. lividans* (pBS2019/pBS2018); IX, *S. lividans* (pBS2020/pBS2018).

FIG. 8. Alignments of the conserved catalytic residues of NonJK with KSs from FAS, type I and -II PKS and type III PKS. The conserved Cys residue for C—C or C—O bond formation and His-His or His-Asn residues for decarboxylation are highlighted. Protein accession numbers are given after the protein names: FabB, P14926; FabF, P39435; DEBS1, Q03131; PikAIV, AAC69332; Act KSα, CAC44200; Tcm KSα, AAA67515; CHS2, P30074; RppA, BAA33495; NonJ, AAD37451; and NonK, AAD37450.

DETAILED DESCRIPTION OF THE INVENTION

I. In General

Figure 1:
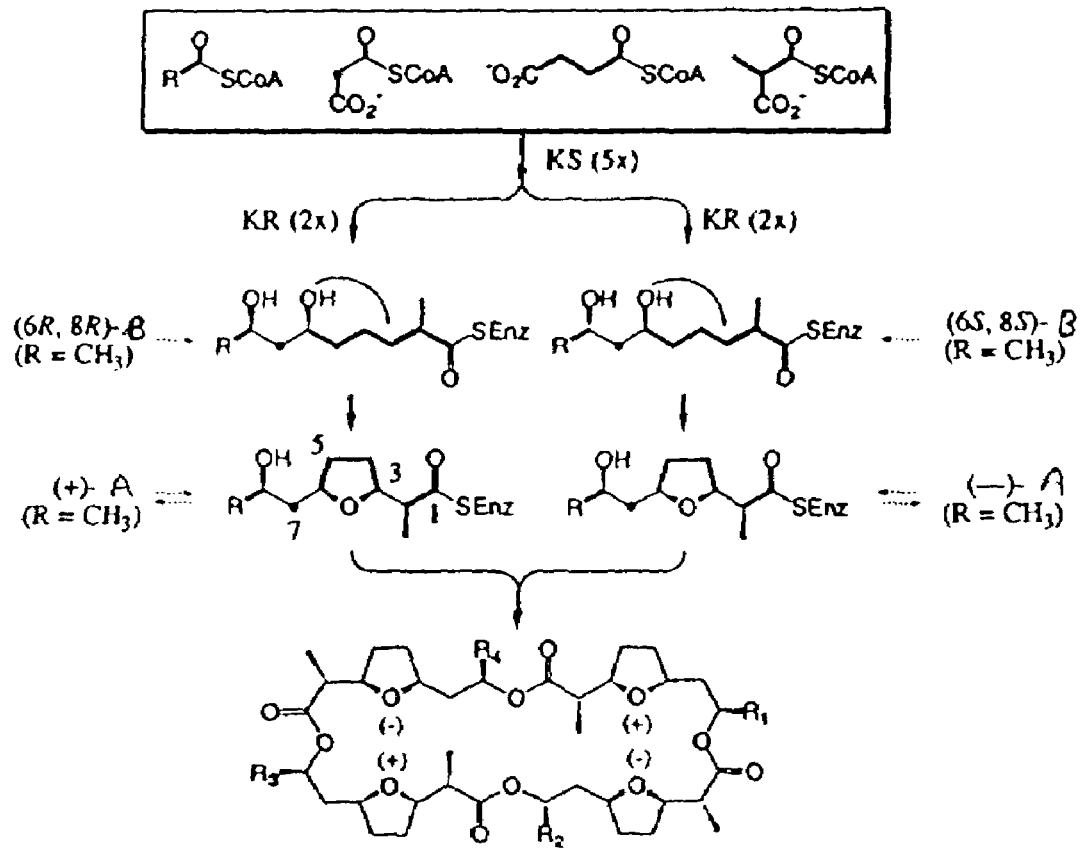
FIG. 1. Early proposed pathway for macrotetrolide biosynthesis in *S. griseus*.

Before the present materials methods are described, it is understood that this invention is not limited to the particular methodology, protocols, cell lines, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The practice of the present invention will employ, unless otherwise indicated, conventional techniques of molecular biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press:

1989); DNA Cloning, Volumes I and II (D. N. Glover ed., 1985); Oligonucleotide Synthesis (M. J. Gait ed., 1984); Mullis et al. U.S. Pat. No: 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986).

II. Definitions

The terms "nonJ, nonK, nonL, nonJK, or nonJKL open reading frame", and "nonJ, nonK, nonL, nonJK or nonJKL ORF" refer to an open reading frame in the nonactin biosynthesis gene cluster as isolated from *Streptomyces griseus*. The term also embraces the same open reading frames as present in other macrotetrolide-synthesizing organisms (e.g. other strains and/or species of *Streptomyces*, and the like). The term encompasses allelic variants and single nucleotide polymorphisms (SNPs). In certain instances the defined terms are used synonymously with the encoded polypeptide may include conservative amino acid substitutions. The term "open reading frame" shall also include subsets of nucleotides as exemplified by those encoding domains encompassing a particular catalytic site of an enzyme. The particular usage will be clear from context.

The terms "isolated" "purified" or "biologically pure" refer to material which is substantially or essentially free from components which normally accompany it as found in its native state. With respect to nucleic acids and/or polypeptides the term can refer to nucleic acids or polypeptides that are no longer flanked by the sequences typically flanking them in nature. A "purifed" polypeptide shall also refer to a polypeptide recombinantly expressed in a host cell and utilized according to the present invention in the in vivo setting.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The term also includes variants on the traditional peptide linkage joining the amino acids making up the polypeptide.

The terms "nucleic acid" or "oligonucleotide" or grammatical equivalents herein refer to at least two nucleotides covalently linked together. A nucleic acid of the present invention is preferably single-stranded or double stranded and will generally contain phosphodiester bonds, although in some cases, as outlined below, nucleic acid analogs are included that may have alternate backbones, comprising, for example, phosphoramide (Beaucage et al. (1993) *Tetrahedron* 49:1925) and references therein; Letsinger (1970) *J. Org. Chem.* 35:3800; Sprinzl et al. (1977) *Eur. J. Biochem.* 81: 579; Letsinger et al. (1986) *Nucl. Acids Res.* 14: 3487; Sawai et al. (1984) *Chem. Lett.* 805, Letsinger et al. (1988) *J. Am. Chem. Soc.* 110: 4470; and Pauwels et al. (1986) *Chemica Scripta* 26: 141 9), phosphorothioate (Mag et al. (1991) *Nucleic Acids Res.* 19:1437; and U.S. Pat. No. 5,644, 048), phosphorodithioate (Briu et al. (1989) *J. Am. Chem. Soc.* 111 :2321, O-methylphophoroamidite linkages (see Eckstein, *Oligonucleotides and Analogues: A Practical Approach*, Oxford University Press), and peptide nucleic acid backbones and linkages (see Egholm (1992) *J. Am. Chem. Soc.* 114:1895; Meier et al. (1992) *Chem. Int. Ed. Engl.* 31: 1008; Nielsen (1993) *Nature*, 365: 566; Carlsson et al. (1996) *Nature* 380: 207). Other analog nucleic acids include those with positive backbones (Denpcy et al. (1995) *Proc. Natl. Acad. Sci. USA* 92: 6097; non-ionic backbones (U.S. Pat. Nos. 5,386,023, 5,637,684, 5,602,240, 5,216,141 and 4,469, 863; Angew. (1991) *Chem. Intl. Ed. English* 30: 423; Letsinger et al. (1988) *J. Am. Chem. Soc.* 110:4470; Letsinger et al. (1994) *Nucleoside & Nucleotide* 13:1597; Chapters 2 and 3, ASC Symposium Series 580, "Carbohydrate Modifications in Antisense Research", Ed. Y. S. Sanghui and P. Dan Cook; Mesmaeker et al. (1994), *Bioorganic & Medicinal Chem. Lett.* 4: 395; Jeffs et al. (1994) *J. Biomolecular NMR* 34:17; *Tetrahedron Lett.* 37:743 (1996) and non-ribose backbones, including those described in U.S. Pat. Nos. 5,235,033 and 5,034,506, and Chapters 6 and 7, ASC Symposium Series 580, *Carbohydrate Modifications in Antisense Research*, Ed. Y. S. Sanghui and P. Dan Cook. Nucleic acids containing one or more carbocyclic sugars are also included within the definition of nucleic acids (see Jenkins et al. (1995), *Chem. Soc. Rev.* pp 169-176). Several nucleic acid analogs are described in Rawls, C & E News Jun. 2, 1997 page 35. These modifications of the ribose-phosphate backbone may be done to facilitate the addition of additional moieties such as labels, or to increase the stability and half-life of such molecules in physiological environments.

The term "heterologous" as it relates to nucleic acid sequences such as coding sequences and control sequences, denotes sequences that are not normally associated with a region of a recombinant construct, and/or are not normally associated with a particular cell. Thus, a "heterologous" region of a nucleic acid construct is an identifiable segment of nucleic acid within or attached to another nucleic acid molecule that is not found in association with the other molecule in nature. For example, a heterologous region of a construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a host cell transformed with a construct which is not normally present in the host cell would be considered heterologous for purposes of this invention.

A "coding sequence" or a sequence which "encodes" a particular polypeptide (e.g. a PKS, etc.), is a nucleic acid sequence which is ultimately transcribed and/or translated into that polypeptide in vitro and/or in vivo when placed under the control of appropriate regulatory sequences. In certain embodiments, the boundaries of the coding sequence are determined by a start codon at the 5' (amino) terminus and a translation stop codon at the 3' (carboxy) terminus. A coding sequence can include, but is not limited to, cDNA from procaryotic or eucaryotic mRNA, genomic DNA sequences from procaryotic or eucaryotic DNA, and even synthetic DNA sequences. In preferred embodiments, a transcription termination sequence will usually be located 3' to the coding sequence.

Expression "control sequences" refers collectively to promoter sequences, ribosome binding sites, polyadenylation signals, transcription termination sequences, upstream regulatory domains, enhancers, and the like, which collectively provide for the transcription and translation of a coding sequence in a host cell. Not all of these control sequences need always be present in a recombinant vector so long as the desired gene is capable of being transcribed and translated.

"Recombination" refers to the reassortment of sections of DNA or RNA sequences between two DNA or RNA molecules. "Homologous recombination" occurs between two DNA molecules which hybridize by virtue of homologous or complementary nucleotide sequences present in each DNA molecule.

The terms "stringent conditions" or "hybridization under stringent conditions" refers to conditions under which a probe will hybridize preferentially to its target subsequence, and to a lesser extent to, or not at all to, other sequences. "Stringent hybridization" and "stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993) *Laboratory Techniques in Biochemistry and Molecular Biology—Hybridization with Nucleic Acid Probes part I chapter 2 Overview of principles of hybridization and the strategy of nucleic acid probe assays*, Elsevier, N.Y. Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe.

An example of stringent hybridization conditions for hybridization of complementary nucleic acids which have more than 100 complementary residues on a filter in a Southern or northern blot is 50% formnamide with 1 mg of heparin at 42° C., with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see, Sambrook et al. (1989) *Molecular Cloning—A Laboratory Manual* (2nd ed.) Vol. 1-3, Cold Spring Harbor Laboratory, Cold Spring Harbor Press, NY, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. In general, a signal to noise ratio of 2× (or higher) than that observed for an unrelated probe in the particular hybridization assay indicates detection of a specific hybridization. Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

"Expression vectors" are defined herein as nucleic acid sequences that are direct the transcription of cloned copies of genes/cDNAs and/or the translation of their mRNAs in an appropriate host. Such vectors can be used to express genes or cDNAs in a variety of hosts such as bacteria, bluegreen algae, plant cells, insect cells and animal cells. Expression vectors include, but are not limited to, cloning vectors, modified cloning vectors, specifically designed plasmids or viruses. Specifically designed vectors allow the shuttling of DNA between hosts, such as bacteria-yeast or bacteria-animal cells. An appropriately constructed expression vector preferably contains: an origin of replication for autonomous replication in a host cell, a selectable marker, optionally one or more restriction enzyme sites, optionally one or more constitutive or inducible promoters. In preferred embodiments, an expression vector is a replicable DNA construct in which a DNA sequence encoding a one or more PKS and/or NRPS domains and/or modules is operably linked to suitable control sequences capable of effecting the expression of the products of these synthase and/or synthetases in a suitable host. Control sequences include a transcriptional promoter, an optional operator sequence to control transcription and sequences which control the termination of transcription and translation, and so forth.

The term "conservative substitution" is used in reference to proteins or peptides to reflect amino acid substitutions that do not substantially alter the activity (specificity or binding affinity) of the molecule. Typically conservative amino acid substitutions involve substitution one amino acid for another amino acid with similar chemical properties (e.g. charge or hydrophobicity). The following six groups each contain amino acids that are typical conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W).

A "biological molecule that is a substrate for a polypeptide(s)" refers to a molecule that is chemically modified by one or more polypeptides encoded by the specified nucleotide sequence or amino acid. The "substrate" may be a native molecule that typically participates in the biosynthesis of a macrotetrolide, or can be any other molecule that can be similarly acted upon by the specified polypeptide(s) (e.g., a synthetic analog determined to be a substrate).

A "polymorphism" is a variation in the DNA sequence of some members of a species. A polymorphism is thus said to be "allelic," in that, due to the existence of the polymorphism, some members of a species may have the unmutated sequence (i.e. the original "allele") whereas other members may have a mutated sequence (i.e. the variant or mutant "allele"). In the simplest case, only one mutated sequence may exist, and the polymorphism is said to be diallelic. In the case of diallelic diploid organisms, three genotypes are possible. They can be homozygous for one allele, homozygous for the other allele or heterozygous. In the case of diallelic haploid organisms, they can have one allele or the other, thus only two genotypes are possible. The occurrence of alternative mutations can give rise to trialleleic, etc. polymorphisms. An allele may be referred to by the nucleotide(s) that comprise the mutation.

"Single nucleotide polymorphism" or "SNPs are defined by their characteristic attributes. A central attribute of such a polymorphism is that it contains a polymorphic site, "X," most preferably occupied by a single nucleotide, which is the site of the polymorphism's variation (Goelet and Knapp U.S. patent application Ser. No. 08/145,145). Methods of identifying SNPs are well known to those of skill in the art (see, e.g., U.S. Pat. No. 5,952,174).

Abbreviations used herein include LB, Luria-Bertani; nt, nucleotide; ORF, open reading frame; PCR, polmerase chain reaction; PEG, polyethyleneglycol; PKS, polyketide synthase; RBS, ribosomal binding site; Apr, apramycin; R, resistant; Th, thiostrepton; WT, wild-type; and TS, temperature sensitive.

III. Cloning and General Characterization of the Nonactin Biosynthesis Gene Cluster The macrotetrolides are a family of cyclic polyethers composed of four molecules of enantiomeric nonactic acid or its homologues in a (+)(−)(+)(−)-ester linkage and exhibit a broad spectrum of biological activities, ranging from antibacterial, antifungal, antitumor, to immunosuppressive activity. Studies of macrotetrolide biosynthesis in *Streptomyces griseus* have unambiguously established that they are of polyketide origin. Of special interest is the proposal that macrotetrolide biosynthesis involves a pair of enantiospecific polyketide pathways (FIG. 1). This proposal is supported by (a) the efficient incorporation of (6R,8R)- or (6S,8S)-2-methyl-6,8-dihydroxynon-2E-enoic acid B and (±)-A into nonactin (C), (b) the isolation of both (+)- and (−)-A and their dimers from *S. griseus* fermentation, and (c) the genetic and biochemical characterization of NonS that catalyzes formation of (−)-A and its homologues from (−)-B and its homologs. An intriguing corollary of this proposal is the synthesis of a set of enantiomeric polyketides, such as B, presumably by a pair of polyketide synthases (PKSs). To make B from the carboxylic acid precursors, the latter PKSs were originally believed to have invoked (a) the rare use of succinate as an intact four-carbon fragment (C3-C6) and (b) the derivation of a three-carbon unit (C7-C9) from two molecules of acetate. As an initial step in testing this hypothesis, the present inventors initially cloned and heterologously expressed the macrotetrolide biosynthetic gene cluster, revealing a novel type of PKS for polyketide biosynthesis that consists of type II ketoacyl synthases (KSs) and ketoreductases (KRs) but lacks acyl carrier protein (ACP). Kwon et al., *J. Am. Chem. Soc.* 123, 3385 (2001); Smith et al., *Antimicrob Agents Chemother.* 2000, 44, 1809.

A 55-kb contiguous DNA region was cloned from *S. griseus* DSM40695 using the previously characterized nonR resistance gene as a probe. Inactivation of nonS, a gene adjacent to nonR, completely abolished macrotetrolide production, confirming that the cloned DNA encodes macrotetrolide biosynthesis. Nucleotide sequence analysis of a 30-kb fragment of the cloned region revealed 32 open reading frames. In addition to nonR and nonS, as well as other biosynthesis, resistance, and regulatory genes, the sequenced gene cluster consisted of 5 KSs and 4 KRs but apparently lacked an ACP (shown at FIG. 2A). Smith et al., *Anti-microb Agents Chemother.* 2000, 44, 1809.

Figure 2:
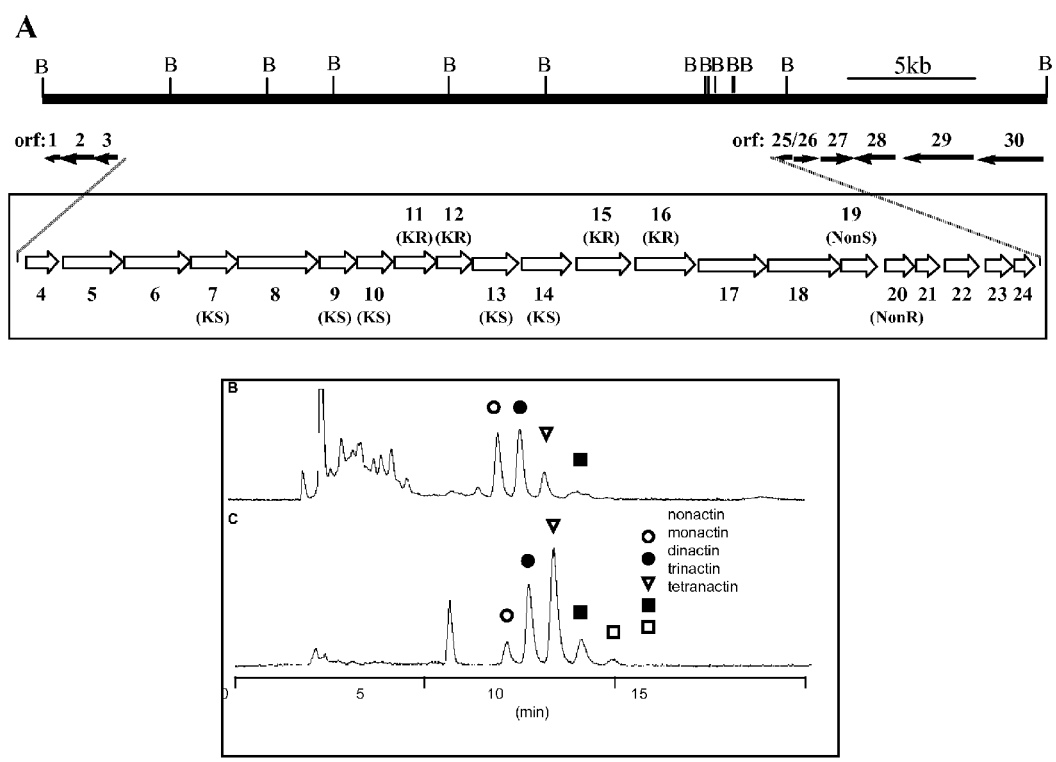
FIG. 2. The macrotetrolide biosynthetic gene cluster from *S. griseus* DSM40695 (A) and HPLC analysis of macrotetrolide production in *S. lividans* (pBS2013) (B) and *S. griseus* DSM40695 (C). The region contained in pBS2013 is boxed.
Figure 3:
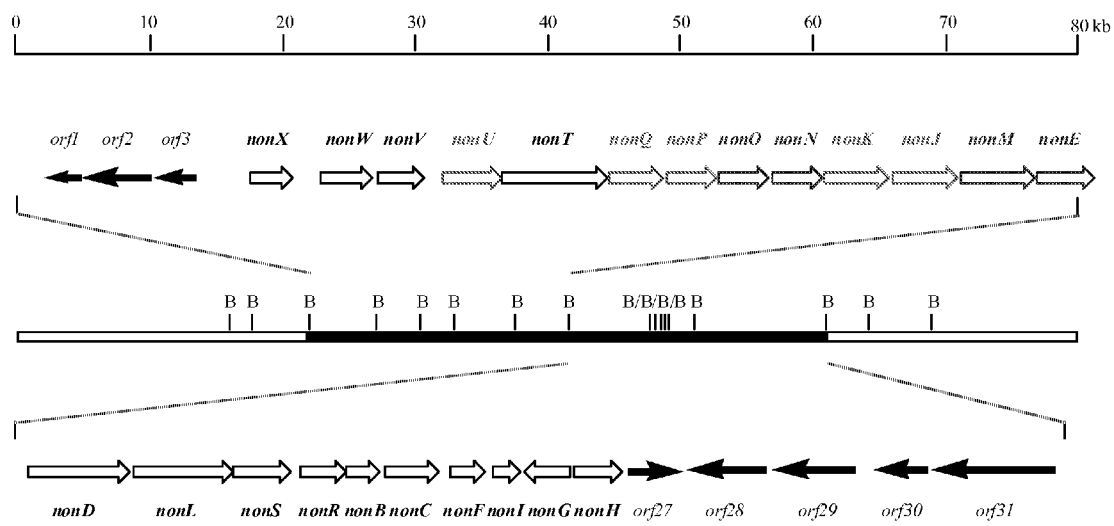
FIG. 3. A restriction map of a 55 Kb contiguous DNA region from *S. griseus* DSM40695 showing general organization of the macrotetrolide biosynthetic gene cluster.

Traditionally, PKSs have been classified as one of three types. Type I PKSs are multifunctional enzymes that are organized into modules and type II PKSs are multienzyme complexes consisting of discrete, largely monofunctional proteins, both of which are found so far only in microorganisms. Despite the structural difference, type I and II PKSs share a high degree of amino acid sequence similarity and both types of PKSs use ACP to activate substrates and to channel the growing polyketide intermediates. Chalcone synthase and its homologues, also known as type III PKSs, are distributed mainly in plants and found very recently in microorganisms as well. They are different structurally and mechanistically from the former and are essentially condensing enzymes that have no apparent amino acid sequence similarity to KSs of both type I and II PKSs. Type III PKSs lack ACP and act directly on the coenzyme A (CoA) ester of simple carboxylic acids. The 5 KSs identified within the macrotetrolide gene cluster and schematically shown in FIG. 2A are discrete proteins, three of which, orf7, orf13 and orf14, are highly homologous to KS of type II PKSs and 2 of which, orf9 and orf10, resemble KS of type II fatty acid synthases. The present inventors observed that if the sequenced region encompasses all the genes for macrotetrolide biosynthesis, the 5 KSs and 4 KRs must catalyze the assembly of (+)- and (−)-B from the carboxylic acid precursors in the absence of ACP, representing a novel type of PKS for polyketide biosynthesis.

To exclude the possibility that the ACP could reside outside the sequenced region, the inventors carried out a series of inactivation of orfs that flank the genes known to be essential for macrotetrolide biosynthesis, including the KSs and KRs as well as the nonS and nonR genes. Since genes encoding antibiotic production in microorganisms are often clustered, the inventors reasoned that sequential inactivation of orfs until the resultant mutants no longer exhibit macrotetrolide non-producing phenotype should allow the localization of the boundaries of the macrotetrolide biosynthetic gene cluster. Thus, inactivation of orf2, orf3, orf27, orf28, or orf30 generated *S. griseus* mutants that show no difference in macrotetrolide production as compared to the wild type *S. griseus* strain. In contrast, macrotetrolide production is severely impaired or totally abolished in *S. griseus* mutants whose orf4, orf6, orf7, orf9, orf10, orf11, orf12, orf13, orf14, orf15, orf16, orf19 (nonS), or orf22 was inactivated. These results suggested that the boundaries of the macrotetrolide biosynthetic gene cluster lie at orf3 to orf4 and orf22 to orf25, respectively (FIG. 2A).

To ascertain that the macrotetrolide PKS does not recruit an ACP residing at another position within the *S. griseus* chromosome and that the identified gene cluster is sufficient for macrotetrolide biosynthesis, the inventors demonstrated the production of macrotetrolides in a heterologous host. They chose *Streptomyces lividans* 1326 as a host because vector systems for the expression of PKS gene clusters in this organism have been well developed and used to produce various natural products. Thus, a 25-kb fragment harboring orf4 to orf26 was cloned under the actI promoter on an apramycin-resistant pSET152 derivative, yielding pBS2013. Introduction of pBS2013 into *S. lividans* 1326 afforded apramycin-resistant *S. lividans* 1326 (pBS2013) transformants that were cultured in AP medium. As shown in FIGS. 2B-C, macrotetrolide production in *S. lividans* 1326 (pBS2013) was evident upon high performance liquid chromatography (HPLC) analysis of the resultant fermentation, as compared to that of the wild type *S. griseus* DSM40695 strain; these metabolites were absent from fermentation of the *S. lividans* 1326 (pSET152) negative control. The identity of the macrotetrolides produced were verified by electrospray mass spectroscopy analysis, yielding the characteristic molecular ions (m/e for [M+Na]$^+$) of 759.4241 for C ($C_{40}H_{64}O_{12}$+Na, calcd. 759.4297), 773.4230 for monactin (D) ($C_{41}H_{68}O_{12}$+Na, calcd. 773.4453), 787.4333 for dinactin (E) ($C_{42}H_{72}O_{12}$+Na, calcd. 787.4610), and 801.4930 for trinactin (F) ($C_{43}H_{76}O_{12}$+Na, calcd. 801.4767). It is noteworthy that *S. griseus* DSM40695 accumulates the macrotetrolides predominantly in mycelia (~40 mg/l). In contrast, *S. lividans* 1326 (pBS2013) preferentially secretes the macrotetrolides into medium (~10 mg/l) with only very small quantity accumulated in mycelia (~0.5 mg/l). The latter observation was consistent with findings from the genome sequencing project of *Streptomyces coelicolor*, a very close cousin of *S. lividans*, that these organisms have an unusually high number of efflux pump proteins that efficiently export secondary metabolites out of the cells.

Macrotetrolide production in *S. lividans* 1326 (pBS2013) unambiguously demonstrated that the 23 orfs on pBS2013 are sufficient to support macrotetrolide biosynthesis from the carboxylic acid precursors, excluding the participation of other *S. griseus* gene products in macrotetrolide biosynthesis. It should be noted that this data fell short of excluding completely the possibility that the macrotetrolide PKS recruits an ACP from the hosts' fatty acid biosynthetic machinery. It is known that malonyl CoA-ACP transacylase from fatty acid biosynthetic pathway is an essential component of type II PKS. However, there is no evidence for crosstalk between fatty acid synthase ACP and PKS. Both type I or II PKSs known to date all include an ACP, either as a domain or a discrete protein, without which the PKSs are not functional. Therefore, the finding that the macrotetrolide PKS consists of discrete KS and KR but lacks ACP uncovered an ACP-independent type II PKS for polyketide biosynthesis.

IV. Identification of C—O Bond Formation by a Polyketide Synthase

A. Materials and Methods

Materials and methods related to the characterization of the nonJKL genes described in this section are presented below.

Standard Molecular Biology Techniques. Examples of such techniques and instructions sufficient to direct persons of skill through many cloning exercises described herein are found in Berger and Kimmel (1989) *Guide to Molecular Cloning Techniques, Methods in Enzymology* 152 Academic Press, Inc., San Diego, Calif. (Berger); Sambrook et al. (1989) *Molecular Cloning—A Laboratory Manual* (2nd ed.) Vol. 1-3, Cold Spring Harbor Laboratory, Cold Spring Harbor Press, NY; Ausubel (19 1994) *Current Protocols in Molecular Biology*, Current Protocols, a joint venture between Greene Publishing Associates, Inc. and John Wiley & Sons, Inc., U.S. Pat. No. 5,017,478; and European Patent No. 0,246,864.

Gene inactivation and mutant complementation. Inactivation of nonJKU in *S. griseus* and nonPQ in *S. lividans* (pBS2013) by gene replacement, complementation of the resultant mutants by either expression of the inactivated gene in trans or fermentation in the presence of exogenous (±)-3, and production of 1 by both the wild-type and recombinant *S. griseus* and *S. lividans* strains were carried out as reported previously for nonS (1) and the entire macrotetrolide biosynthesis gene cluster.

Figure 9:
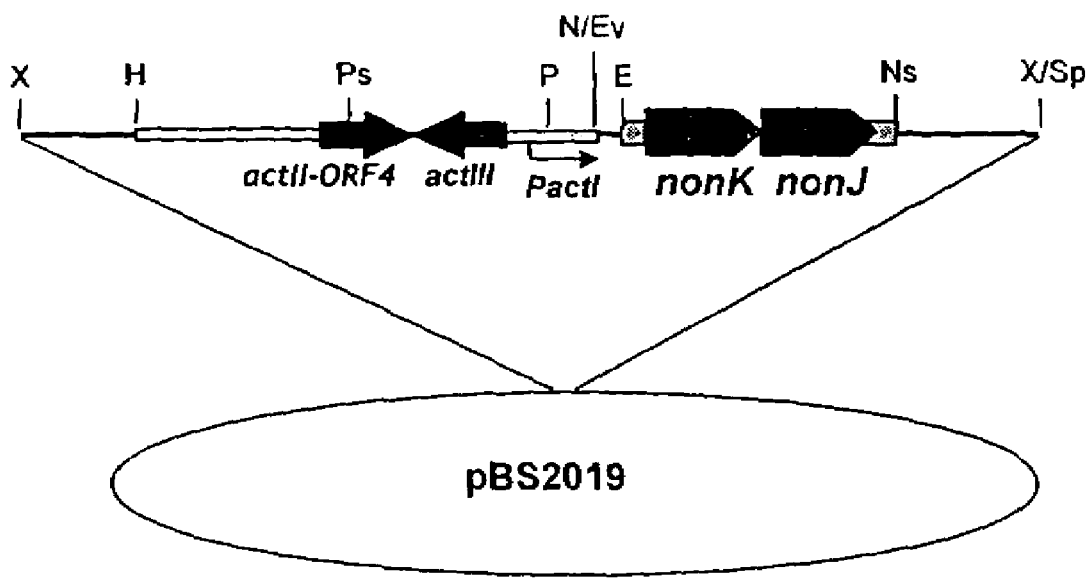
FIG. 9. A map of non gene expression cassettes as exemplified by pBS2019 for nonJK under the actI promoter. The actI promoter as a HindIII-NdeI fragment and the nonJK genes as an EcoRI-NsiI fragment were cloned into pSET152. Restriction sites: E, EcoRI; Ev, EcoRV; H, HindIII; N, NdeI; Ns, NsiI; P, PacI; Ps, PstI, Sp, SpeI; X, XbaI.

Construction of non gene expression cassettes pBS2014 to pBS2021 and biotransforamtion of (±)-3 into 1 in *S. lividans* 1326. In general, the actI promoter was first combined with the desired non gene(s) in the *E. coli* vector, Lithmus 28 (NEB, Beverly, Mass.), and the resultant actI/non gene fragment was then transferred into *Streptomyces* shuttle vectors, pSET152 or pWHM3 (FIG. 9). The actI promoter was retrieved from pCK12 as a 3.2-kb of NdeI-HindIII fragment and ligated into the EcoRV and HindIII sites of Litmus 28 to yield pBS2022. The non genes were first subcloned into an *E. coli* vector and then moved as EcoRI-NsiI fragment into the same sites of pBS2022. The resultant actI/non gene fragment was finally moved as a XbaI-SpeI fragment and cloned into the XbaI site of pSET152 or pWHM3 to afford the final expression cassettes. As summarized in FIG. 6B, the non cluster (schematically illustrated in FIG. 6A) is dissected into two halves. Genes from the upstream half were cloned into pSET152, and genes from the downstream half were cloned into pWHM3, yielding the corresponding expression constructs pBS2014 to pBS2019. Expression of non genes in both pSET152 and pWHM3-based cassettes were under the control of the actI promoter. For nonL expression, both the actI promoter and snpA promoter from pANT865 were used. Constructs with either promoter give similar biotransformation result.

These plasmids were introduced into *S. lividans* either pairwise or individually and selected with apramycin (for pSET152-based plasmids) and/or thistrepton (for pWHM3-based plasmids). The resultant *S. lividans* recombinant strains were fermented (50 ml) in the presence of exogenously added (±)-3 (5 mg). Isolation and HPLC and ESI-MS analyses of 1 were carried out as previously described (1,2). The bulk of (±)-3 was recovered in the fermentation broth due to its poor cell permeability, reducing the overall yield of 1 produced from these experiments.

Construction of the nonJ and nonK mutant expression cassettes pBS2020 and pBS2021. The NonK Cys161Gly and NonJ Cys169Gly mutants were generated by site-directed mutagenesis with the following pairs of primers 5'-CGGT-GAGCTGCGC<u>GGC</u>GCCTCCTCCTCGGTGC-3'(SEQ ID NO: 8)/3'-GCCACTCGACGCCG<u>CCG</u>CGGAGGAGGAGCCACG-5' (SEQ ID NO: 9) (for nonK) and 5'-GCGTGGCGGGCTCC<u>GGC</u>AATGTGGCGCTGCGG-3'(SEQ ID NO: 10)/3'-p-5' (SEQ ID NO: 11) (for nonJ) (the Gly codons are underlined), respectively, using the QuickChange kit from Stratagene (La Jolla, Calif.) according to the manufacture's instruction. The resultant nonJK mutants were cloned into pSET152 to yield pBS2020 and pBS2021, in which nonJK expression is under the control of the actI promoter. pBS2020 or pBS2021 was co-transformed with pBS2018 into *S. lividans*, and the resultant *S. lividans* recombinant strains were tested for biotransformation of (±)-3 into 1 as described above.

Figure 10:
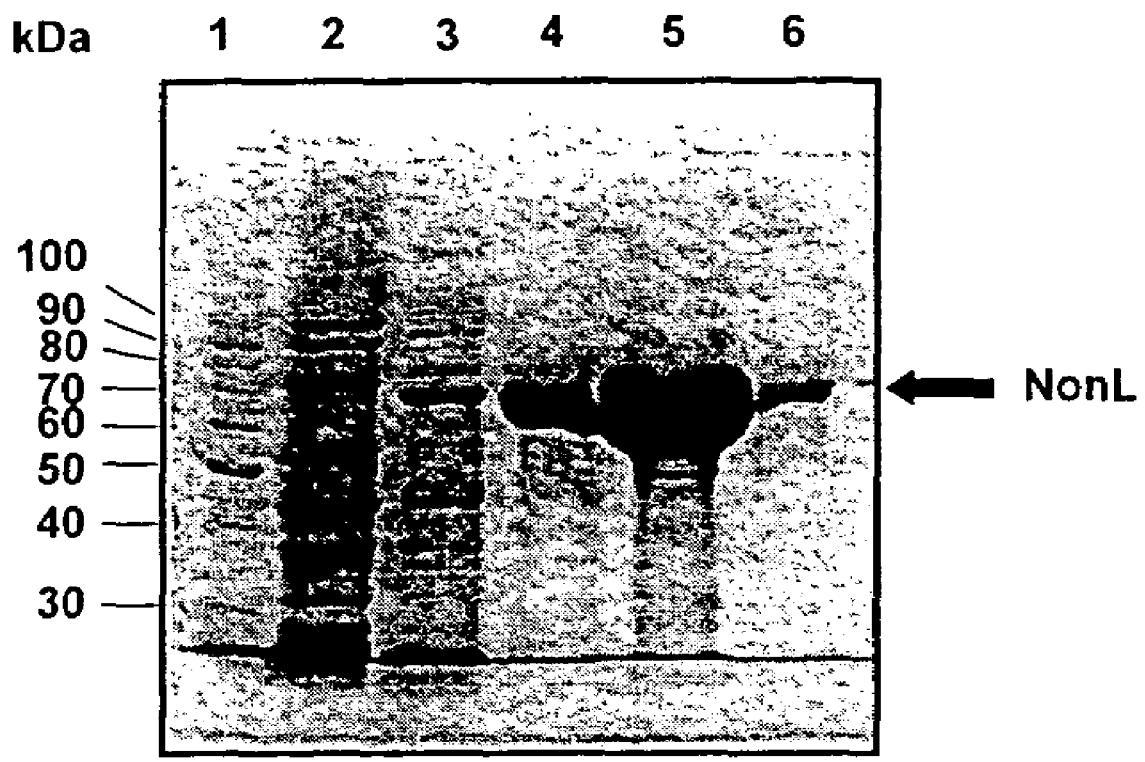
FIG. 10. SDS-PAGE analysis of nonL expression and NonL purification from BL21 (DE3) (pBS2023). NonL was purified by affinity chromatography on Ni-NTA resin according to the manufacturer's procedure (Novagen). Lanes: 1, molecular weight marker; 2, total lysate before IPTG induction; 3, total lysate after IPTG induction; 4-6, NonL eluted from Ni-NTA resin with 250 mM imidazole.

Expression of nonL and characterization of NonL as a CoA ligase. The nonL gene was amplified from pBS2013 by PCR with forward primer of 5'-CGCCGGGGAGAC<u>CATATG</u>ATCGACGATGTGCTC-3' (SEQ ID NO:12) (the NdeI site is underlined) and reverse primer of 3'-GCATACT-TGGTCCTT<u>CTTAAG</u>GCCCGCCCGGTC-5' (SEQ ID NO:13)(the EcoRI site is underlined) and cloned as a 1.7-kb NdeI-EcoRI fragment into the same sites of pET28a (Novagen, Madison, Wis.) to yield pBS2023. The expression of nonL in *E. coli* BL-21 (DE-3) (pBS2023) and purification of the resulting NonL protein by affinity chromatography on Ni-NTA resin were carried out under the standard conditions recommended by Novagen (FIG. 10). The incubation temperature was lowered to 15° C. to improve the solubility.

For in vitro assay of NonL as a CoA ligase, the complete assay solution (50 μl) consisted of 2 mM ATP, 2 mM CoA, 2 mM (±)-3, 10 mM KCl, 2 mM DTT, 5 mM MgCl$_2$, 50 to 800 nM NonL in 10 mM Tris-HCl, pH 8.0. The reaction mixture was incubated at 30° C. for 2 hr and analyzed by HPLC on an Alltima C$_{18}$ column (4.6×250 mm, 5μ, 100 Å, Alltech, Deerfield, Ill.). The column was first eluted in 20 mM NH$_4$Ac, pH 5.8, for 5 min, followed by linear gradient from 0% to 50% CH$_3$CN in 20 mM NH$_4$Ac, pH 5.8 for 10 min, and maintained at 50% CH$_3$CN in 20 mM NH$_4$Ac for an additional 10 min, with flow rate of 0.8 ml/min and detection at 260 nm.

B. Bond Formation by Polyketide Synthases

As generally described in a previous section, PKSs have been classified according to their enzyme architecture, and three types of bacterial PKSs are known to date (FIGS. 4A-C and 5A, B). Type I PKSs are multifunctional proteins that harbor sets of noniteratively used distinct active sites, termed modules, each of which is responsible for the catalysis of one cycle of polyketide chain elongation. (Bacterial type I PKS that acts iteratively is also known but very rare and, therefore, is not included here.) A typical module consists minimally of an acyltransferase (AT) domain for extender unit selection and transfer, an ACP domain for extender unit loading, a ketoacyl synthase (KS) domain for decarboxylative condensation between the aligned acyl thioesters to elongate the growing polyketide chain (FIG. 4A). Additional domains have also been identified for the modification of the initial β-keto group, such as a ketoreductase (KR) domain for a β-hydroxyl group, a dehydratase (DH) domain for an alkene moiety, an enoyl reductase (ER) domain for an alkane moiety, or an methyl transferase (macrotetrolide) domain for the introduction of a methyl branch into the α-position of the growing polyketide chain, contributing additional structural diversities into polyketide biosynthesis. The modular structure of type I PKS and the co-linear relation between the order of domains and modules on each PKS and the functional groups in the resultant polyketide product have greatly facilitated the rational engineering of PKSs for combinatorial biosynthesis. Numerous polyketides with predicted structural alterations have been produced by targeted domain or module substitution, deletion, addition, reposition, or by introduction of other mutations into PKSs, as well as by exploiting intermodular communication to facilitate the transfer of biosynthetic intermediates between unnaturally linked PKS modules.

As best illustrated in FIG. 4B, Type II PKSs are multienzyme complexes that carry a single set of iteratively used activities and consist minimally of the KSα, KSβ, and ACP subunits. (The KSβ subunit lacks the conserved cysteine (Cys) residue essential for the KS activity and is also known as chain length factor or chain initiation factor.) Although self-malonylation of the ACP subunit has been observed in vitro, it is generally accepted that the minimal type II PKS requires the malonyl CoA:ACP transferase (MAT) from the host's fatty acid biosynthetic machinery to synthesize polyketide from malonyl CoA in vivo. MAT catalyzes the transfer of the malonyl group from malony CoA to the ACP subunit to form malonyl-ACP. To initiate polyketide biosynthesis, malonyl-ACP is decarboxylated by KSβ to afford the starter unit acetyl-ACP that is subsequently transferred to KSα. Sequential decarboxylative condensations between the aligned acyl thioesters yield the linear poly-β-ketoacyl-ACP intermediate (FIG. 4B). Additional subunits have also been identified for the modification of the poly-β-ketoacyl-ACP intermediate, such as specific KRs, cyclases, and aromatases, furnishing the characteristic polycyclic aromatic products. Although the molecular logic of how type II PKSs control structural diversity in polyketide biosynthesis remains poorly understood, numerous novel aromatic polyketides have been produced by combinatorial biosynthesis via engineered type II PKSs. However, most of these experiments were governed mainly by intuition and serendipity. The so-called "design rules", while with enough predictive power for the rational production of novel aromatic polyketides by the appropriate mixing and matching of the subunits, were formulated exclusively from empirical observations rather than mechanistic understanding of the type II PKS complex. Despite their structural difference, type I and type II PKSs share a high degree of amino acid sequence similarity, and both types of PKSs use ACP to activate the acyl CoA substrates and to channel the growing polyketide intermediates.

Now referring to FIG. 4C and FIG. 5B, Type III PKSs, also known as chalcone synthases-like PKSs, are distributed predominantly in plants and have been found in microorganisms only very recently. They are different from the former two types of PKSs both in structure and mechanism. Type III PKSs are essentially condensing enzymes. Although they possess a highly conserved Cys residue that is essential for the PKS activity, the amino acid sequences of this Cys motif have no apparent similarity to that of the KSs of both type I and type II PKSs. Type III PKSs lack ACP and act directly on the acyl CoA substrates. They utilize the Cys active site iteratively by first selecting an acyl CoA starter unit and then catalyzing sequential decarboxylative condensation with malonyl CoA directly to synthesize a linear poly-β-ketoacyl CoA intermediate that is subsequently cyclized into aromatic products (FIG. 4C). Although other subunits have been found for plant type III PKS, such as KR and methyl malonyl CoA-specific subunit, contributing additional structural diversity for plant polyketide biosynthesis, such subunit has not been identified for bacterial type III PKSs. Combinatorial biosynthesis with engineered type III PKSs were limited to plant enzymes so far. In contrast to type I and type II PKSs, the relative simplicity of the type III PKSs has greatly facilitated their structural characterization. The crystal structures of two members of the type III PKS family, a chalcone synthase from *Medicago sativa* (alfalfa) and a 2-pyrone synthase from *Gerbera hybrida* (daisy), have been recently determined, revealing a common three-dimensional fold, a set of conserved catalytic residues, similar CoA binding sites, but variable size of the active site cavity. The latter results imply that type III PKSs may control starter unit selectivity and limit the chain length of polyketide products by varying the size of the active site cavity. Changing the volume of the active site cavity through site-directed mutagenesis indeed has allowed alterations of both the choice of the starter unit and the final length of the resultant polyketide products, providing a structural basis for engineering type III PKSs for structural diversity C. Novel C—O Bond Formation by a Polyketide Synthase In the present invention, the inventors have identified two KSs, NonJK, that catalyze C—O bond formation in nonactin (1) biosynthesis, as illustrated in FIG. 5C. In general, the NonJK KSs act on (±)-nonactyl CoA (2), catalyze tetramerization of (+)- and (−)-2 in a stereospecific (+)(−)(+)(−)-fashion into 1, and require the Cys residue conserved among all KSs for this reaction (FIG. 5C).

As described above, nonactin belongs to the macrotetrolide family of cyclic polyethers that exhibit a broad spectrum of biological activities, including antibacterial, antifungal, antitumor, and immunosuppressive activity. Referring to FIG. 5C, 1 is structurally composed of four molecules of (+)- and (−)-nonactic acid (3) in a (+)(−)(+)(−)-macrotetrolide linkage, an intriguing molecular topology not seen in other natural products. The biosynthesis of 1 has been studied by feeding experiments with various isotope-labeled precursors and by cloning and characterizing the biosynthesis gene cluster from *Streptomyces griseus* DSM40695 (previously described herein). These studies established that (±)-3 is synthesized by a PKS that lacks an ACP. The idea that (+)- and (−)-3 are intermediates in nonactin biosynthesis was supported by their efficient incorporation into 1 and the isolation of both (+)- and (−)-3 as well as their dimers from *S. griseus* fermentation.

There are five KS genes within the cluster, nonJKPQU, which have deduced products that are highly homologous to KSs of the type II PKS (FIGS. 2A and 6A). Inactivation of any one of them either completely abolishes (nonJKPQ) or significantly impaires (nonU) 1 production, and expression of any one of them in trans in the corresponding mutants restores 1 production, confirming that all five KS genes are involved in 1 biosynthesis. Since KSs are only known to catalyze C—C bond forming steps in polyketide biosynthesis, the inventors reasoned that all KS mutants would retain the enzymatic functions for the C—O bond-forming tetramerization steps involved in (±)-3 to 1 and, thereby, nonactin production could be restored to all KS mutants by fermenting them in the presence of exogenously added (±)-3. That was indeed the case for the nonPQU mutants but not for the nonJK mutants, suggesting that the NonJK KSs might play a role in the C—O bond-forming steps in nonactin biosynthesis.

To identify the minimal genes required for the C—O bond-forming tetramerization steps, the inventors combined plasmid-based expression of the non genes in *Streptomyces lividans* schematically illustrated in FIGS. 6A-B with biotransformation of (±)-3 to 1 in the resultant recombinant strains. The inventors reasoned that the minimal genes required for the tetramerization step could be identified by successive deletion of genes included in the expression cassettes. Thus, *S. lividans* strains harboring various non gene expression cassettes were fermented in the presence of exogenously added (±)-3. The production of 1 was monitored by high performance liquid chromatography (HPLC) and confirmed by electrospray ionization-mass spectrometry (ESI-MS) analysis, yielding a characteristic $(M+Na)^+$ ion at m/z=759.4, consistent with the molecular formula of $C_{40}H_{64}O_{12}$ for 1. As summarized in FIGS. 6B and 6C, all recombinant strains expressing nonJKL genes are effective in biotransformation of (±)-3 into 1 (entries II, VI, VII, and VIII) and deletion of nonJK, or nonL from the expression cassettes completely abolishes their biotransformation ability (entries III, IV, and V), suggesting nonJKL are essential for this activity. Finally, it was established that nonJKL are sufficient for the tetramerization steps by expressing only the nonJKL genes; the resultant recombinant strain is as effective in biotransformation of (±)-3 into 1 (entry VIII) as those strains harboring other non genes in addition to nonJKL. The analysis demonstrates that a substantial portion of the nonactin gene cluster may be absent while the biotransformation of (±)-3 to 1 is still carried out. The nucleotide sequences for the nonJ, nonK and nonL open reading frames are provided herein as SEQ ID NOS. 2, 4 and 6, respectively. The translated polypeptides for nonJ, nonK and nonL are likewise provided as SEQ ID NOS. 3, 5 and 7. SEQ ID NO. 1 is approximately 15 Kb of genomic DNA from the nonactin biosynthesis gene cluster which contains the open reading frames set forth in SEQ ID NOS. 2, 4 and 6. SEQ ID NO. 1 has been deposited with GenBank under Accession No. AF074603. The entire nonactin biosynthesis gene cluster has been deposited with GenBank under Accession Nos. AF263011 and AF263012, along with the deposit of Accession No. AF074603. Cloning of the nonactin biosynthesis gene cluster has previously been described in Smith, W.; Xiang, L.; Shen, B. *Antimicrob. Agents Chemother.* 2000, 44, 1809-1817 and Kwon, H. J., Smith, W. C.; Longkuan X., and Shen, B., *J. Am. Chem. Soc.* 2001, 123, 3385-3386 which are incorporated herein by reference in their entirety for all purposes.

Figure 7:
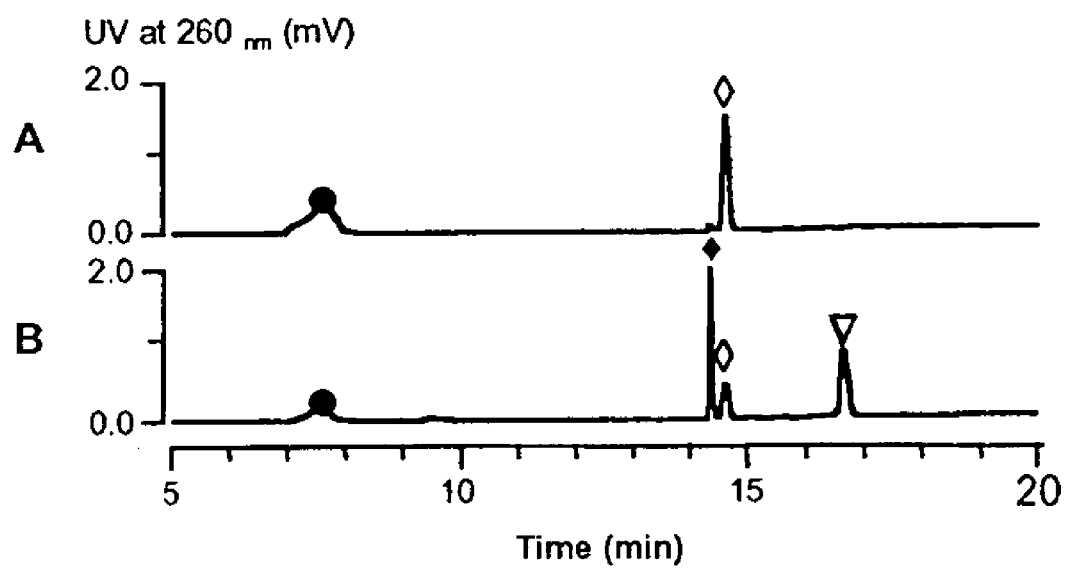
FIG. 7. In vitro synthesis of (±)-2 from (±)-3 catalyzed by NonL, requiring ATP and CoA. (A) Negative control in the absence of NonL and (B) complete assay with 800 nM NonL. ATP, (•); AMP, (♦); CoA, (◊); (±)-2, (▽).

On the basis of its high sequence homology to a family of CoA ligases, the inventors reasoned that NonL, rather than directly contributing to the C—O bond-forming steps, instead activates (±)-3 into CoA esters (±)-2 that are then tetramerized into 1 by the NonJK KSs. To validate this hypothesis, the inventors expressed nonL in *E. coli*, purified NonL as a $His_6$-tagged fusion protein (FIG. 10), and characterized NonL as a CoA ligase. The inventors monitored the in vitro assay of NonL by HPLC analysis: NonL catalyzes the conversion of (±)-3 to (±)-2, requiring CoA and ATP as co-substrates. Under the condition examined, 80% of (±)-3 was converted to (±)-2 in 2 hrs, confirming that NonL recognizes both (+)- and (−)-3 as substrates (FIG. 7). The identity of (±)-2 was verified by ESI-MS, yielding a characteristic $(M-2H)^{2-}$ ion at m/z=474.7, consistent with the molecular formula of $C_{31}H_{52}N_7O_{19}P_3S$.

Since NonJKL are sufficient to biotransform (±)-3 to 1 (FIGS. 6B and 6C, entry VIII), the characterization of NonL as a CoA ligase, catalyzing the conversion of both (+)- and (−)-3 into their CoA esters, indicates that NonJK are responsible for the C—O bond-forming tetramerization steps, acting directly on the CoA ester substrates of (+)- and (−)-2. KSs known to date catalyze only C—C bond formation, although the CoA substrates can be utilized either directly (by type III PKS) or indirectly via acyl-ACPs (by both type I and -II PKS). Thus, as depicted in FIG. 5C, NonJK, in a mechanistic analogy to type III PKS, it was suggested that NonJK first catalyze the transfer of the nonactyl group from (±)-2 to the Cys residue of NonJK to form the nonactyl-S-KS species (FIG. 5C, step a). Unlike KSs that catalyze decarboxylative condensation between the carbon anion nucleophile and acyl-S-KS to form the C—C bond (FIG. 5B), the NonJK KSs catalyze the condensation between the oxygen nucleophile of the —OH group of 2 and nonactyl-S-KS to form the C—O bond, yielding the dimers in the form of CoA esters (FIG. 5C, steps b and c). The latter have been isolated as free acids from *S. griseus* fermentation, supporting the proposed pathway. Iterations of steps a and b or steps a and c eventually lead to the KS-bound linear tetramers that undergo intramolecular condensation between the —OH group of the distal nonactyl unit and the acyl-S-KS carbonyl group to afford 1 (FIG. 5C, step d).

To gain insight into the mechanism of the condensation reaction, the inventors further compared the NonJK sequences with those of other KSs of both fatty acid synthases (FASs) and PKSs. All previously characterized KSs contain a Cys-His-His (for type I and -II FAS and PKS) or Cys-His-Asn (for type III PKS) catalytic triad (FIG. 8). The His-His or His-Asn residues are essential for malonyl-ACP or malonyl CoA decarboxylation to generate the corresponding carbon anion, and the Cys residue catalyzes condensation between the resultant carbon anion and acyl-S-KS to form the C—C bond (FIGS. 5A and 5B). Strikingly, NonJK are characterized with a mutated catalytic triad—Cys-Tyr-His for NonJ or Cys-Gly-His for NonK, suggesting that NonJK lack the decarboxylation activity (FIG. 8). This is consistent with the proposal that NonJK catalyze C—O bond formation by using the —OH as the nucleophile directly.

Finally, to confirm that Cys plays a catalytic role in the C—O bond-forming step, the inventors replaced the conserved Cys residue in NonJ or NonK, respectively, with Gly by site-directed mutagenesis. The resultant mutants completely lose their ability to biotransform (±)-3 into 1 (FIGS. 6B and 6C, entries IX and X). Thus, the NonJK KSs catalyze the C—O bond-forming step in nonactin biosynthesis, acting directly on (±)-2 and using the same active site residue Cys that is used in KS catalysis of C—C bond formation.

In summary, nucleotide sequence analysis of a 30-kb of the macrotetrolide biosynthetic gene cluster revealed thirty two open reading frames (orfs) composed of five discrete ketosynthases (KSs) and four ketoreductases (KRs) but lacks an ACP. The GenBank accession numbers for the macrotetrolide biosynthetic gene cluster are AF263011, AF263012, and AF074603 A 25-kb DNA region encompassing 24 orfs conferred macrotetrolide production to *S. lividans* 1326, which substantiated that macrotetrolide-PKS is a ACP-independent type II PKS composed of five KSs and four KRs. A gene of nonY was recently identified just upstream to nonX. The insert of pBS2013 covers for nonY. Subsequently, two of five KS genes, nonJK were characterized to encode for the conversion of (±)-6-CoA to 1. (See FIG. 11). NonJK was identified as novel KSs catalyzing C—O bond formations between (±)-6-CoA to yield 1 and NonL as an enzyme converting (±)-6 into (±)-6-CoA. The chemistry of NonJK-catalysis was further defined by the inventors revealing stereoselective C—O bond formations performed in sequential order of NonJ-NonK, as described below.

Close examination of nonK predicted two plausible translational starting sites. Frame plot analysis predicted nonK encodes a 462-aa protein (VSKEH-NonK) starting from a GTG-starting codon and translationally-coupled (4-bp) with nonN, the upstream KR-gene. At 111-nucleotide downstream from this GTG-starting codon, the other starting codon of ATG was found and the product deduced from this ATG-codon (MGFCL-NonK) showed head-to-tail homology to the known KSs from type II polyketide synthase (PKS) and fatty acid synthase (FAS). Through polymerase chain reaction (PCR), nonK was amplified, from both starting sites, along with nonJ that is translationally-coupled with nonK (11-bp) and subcloned into Lithmus28 to be combined with nonL generating pBS2043 and pBS2044, respectively (see supporting information for plasmid constructions). Firstly, the inserts (NonK, NonJ, and NonL) were rescued as NdeI-BglII fragments and ligated with NdeI-BamHI digested pIJ4123 to be located downstream to the thiostrepton inducible promoter (tipAp), ribosomal binding site/translational starting codon, and 6×histidine-tag. The ligation mixtures (pBS043/pIJ4123 and pBS2044/pIJ4123, respectively for VSKEH-NonK and MGFCL-NonK) were used to transform *S. lividans* TK-24 and the transformant was selected by kanamycin resistance and later by loss of red pigment production, due to loss of redD, on the regeneration agar. Through plasmid isolation and restriction digestion, *S. lividans* (pBS2045) was identified to harbor pBS2044/pIJ4123 (two out of twelve tested in the liquid cultures, two of five not showing red pigment production even after the thiostrepton-supplementation) but no transformant was found with pBS2043/pIJ4123. Tests for the in vivo conversion-activity of *S. lividans* (pBS2045) clearly indicated that *S. lividans* (pBS2045) could not convert (±)-6 into 1. The inventors also subcloned the inserts of pBS2043 and pBS2044 into pET28a to generate pBS2046 and pBS2047. *E. coli*BL21 (pBS2046) accumulated low level of 1 when supplemented by (±)-6 after IPTG (isopropyl-β-D-thiogalatopyranoside)-induction. Consistent with the result observed with *S. lividans* (pBS2045), no conversion activity was observed from *E. coli* BL21 (pBS2047). SDS (sodium dodecyl sulfate)-PAGE (polyacrylamide gel electrophoresis) analysis revealed that both versions of NonKs were well expressed but almost insoluble and trial to resolve 6×histidine-tagged NonK or any relevant activities through the nickel affinity chromatography have been unsuccessful.

Figure 12:
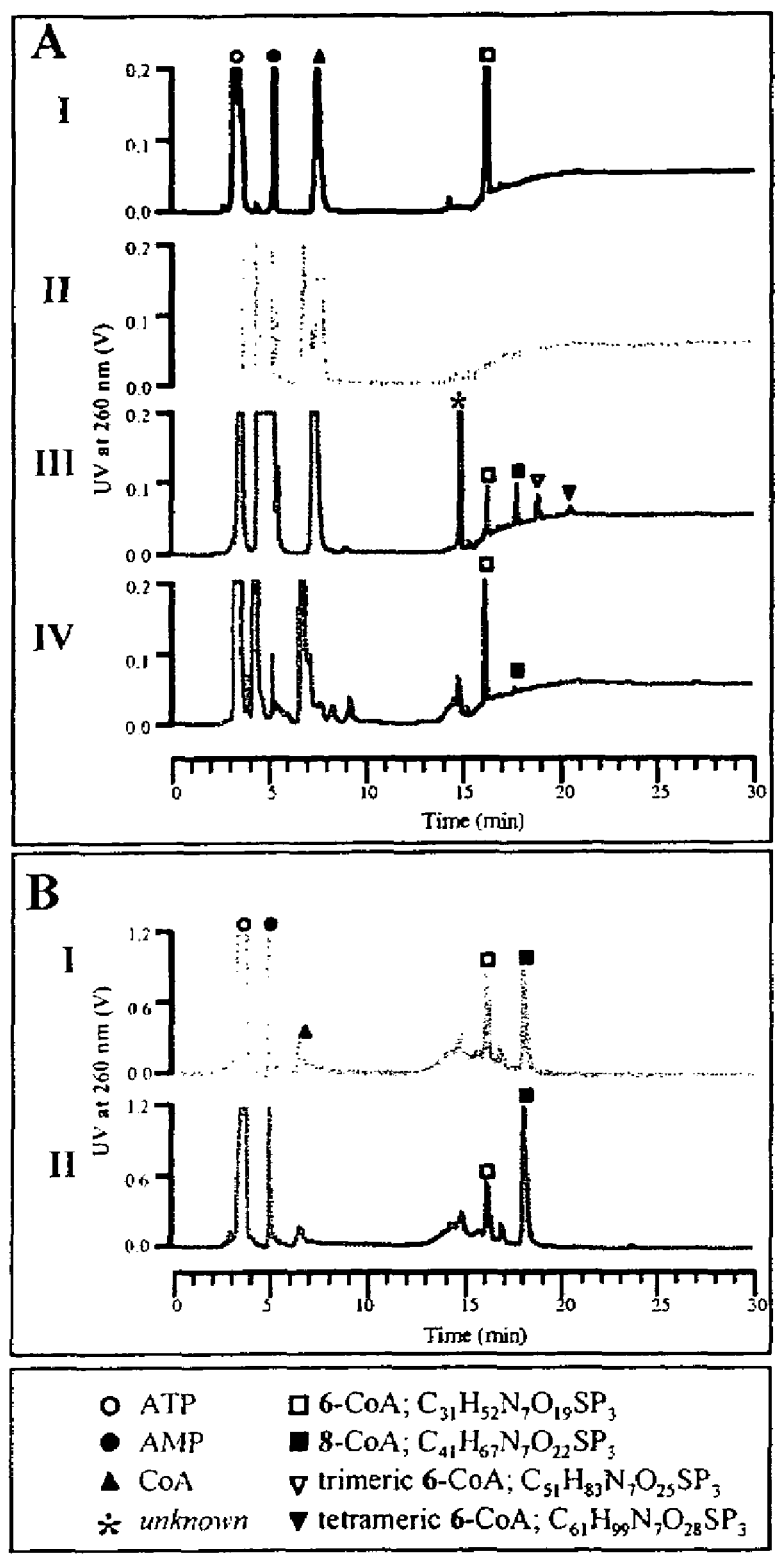
FIG. 12. (A) In vitro synthesis of 6-CoA and its derivatives from 6 by NonL (I), *S. lividans* (pBS2045)-CFE, negative control in the absence of 6 (II), *S. lividans* (pBS2045)-CFE (III), and *E. coli* BL21 (pBS2046)-CFE (IV). The purified NonL or CFEs were incubated with 2 mM ATP, 0.5 mM CoA, and 1 mM 6 for 1 h at 30° C. (B) In vitro synthesis of 6-CoA and 8-CoA by *S. lividans* (pBS2045)-CFE obtained from the nickel affinity chromatography (see the text). The CFE was incubated with 2 mM ATP, 0.5 mM CoA, and 1 mM 6 for 1 h (I) and 2 hs (II) at 30° C.

At this point, the inventors proceeded with cell-free extract (CFE)-based activity assay. CFE of *S lividans* (pBS2045) and *E. coli*BL21 (pBS2046) were incubated with ATP, CoA, and (±)-6 (see supporting information for CFE-preparation and chemical analysis). *S. lividans* (pBS2045)-CFE showed no conversion to 1, as expected from in vivo results, but instead yielded comparable levels of 6-CoA, 8-CoA, trimeric 6-CoA and tetrameric 6-CoA as evidenced by MS analysis that revealed, respectively, molecular ion (m/e for [M–H]⁻) of 950.207 ($C_{31}H_{51}N_7O_{19}SP_3$, calcd 950.217), 1134.336 ($C_{41}H_{67}N_7O_{22}SP_3$, calcd 1134.327), 1318.430 ($C_{51}H_{83}N_7O_{25}SP_3$, calcd 1318.437), and 1502.564 ($C_{61}H_{99}N_7O_{28}SP_3$, calcd 1502.547) (FIG. 12A-III). Production of these series of compounds was dependent on 6 (FIG. 12A-II) and ATP. However, *E. coli* BL21 (pBS2046)-CFE also failed to produce 1 but yielded 6-CoA and a trace level of 8-CoA (FIG. 12A-IV). The results indicated that NonL was well expressed in *E. coli* BL21 (pBS2046) but an enzyme for 8-CoA formation was limitedly expressed, which might be the reason for absence of the in vitro conversion activity to 1. The result from *S. lividans* (pBS2045)-CFE (FIG. 12A-III) suggested that oligomerization of 6-CoA occurs step-by-step with the intermediacy of trimeric 6-CoA and MGFCL-NonK can support oligomerization but not intramolecular cyclization that necessitate full-length of NonK of VSKEH-NonK. From *S. lividans* (pBS2045)-CFE, neither relevant activity nor protein(s) could be resolved with the nickel affinity chromatography. However, surprisingly, the flow-through fraction from the nickel affinity chromatography showed efficient conversion of 6-CoA to 8-CoA in addition to NonL activity (FIG. 12B). It was assumed that removal of association of MGFCL-NonK from NonJ, somehow during nickel affinity chromatography, refined NonJ for it catalysis, the dimerization. This result made the inventors propose that NonJ independently catalyzes dimerization of 6-CoA. The absence of in vitro conversion ability in *E. coli* BL21 (pBS2046) was interpreted as due to lack of NonJ whose translation is dependent on its native sequence of *Streptomyces* ribosomal binding site.

Figure 13:
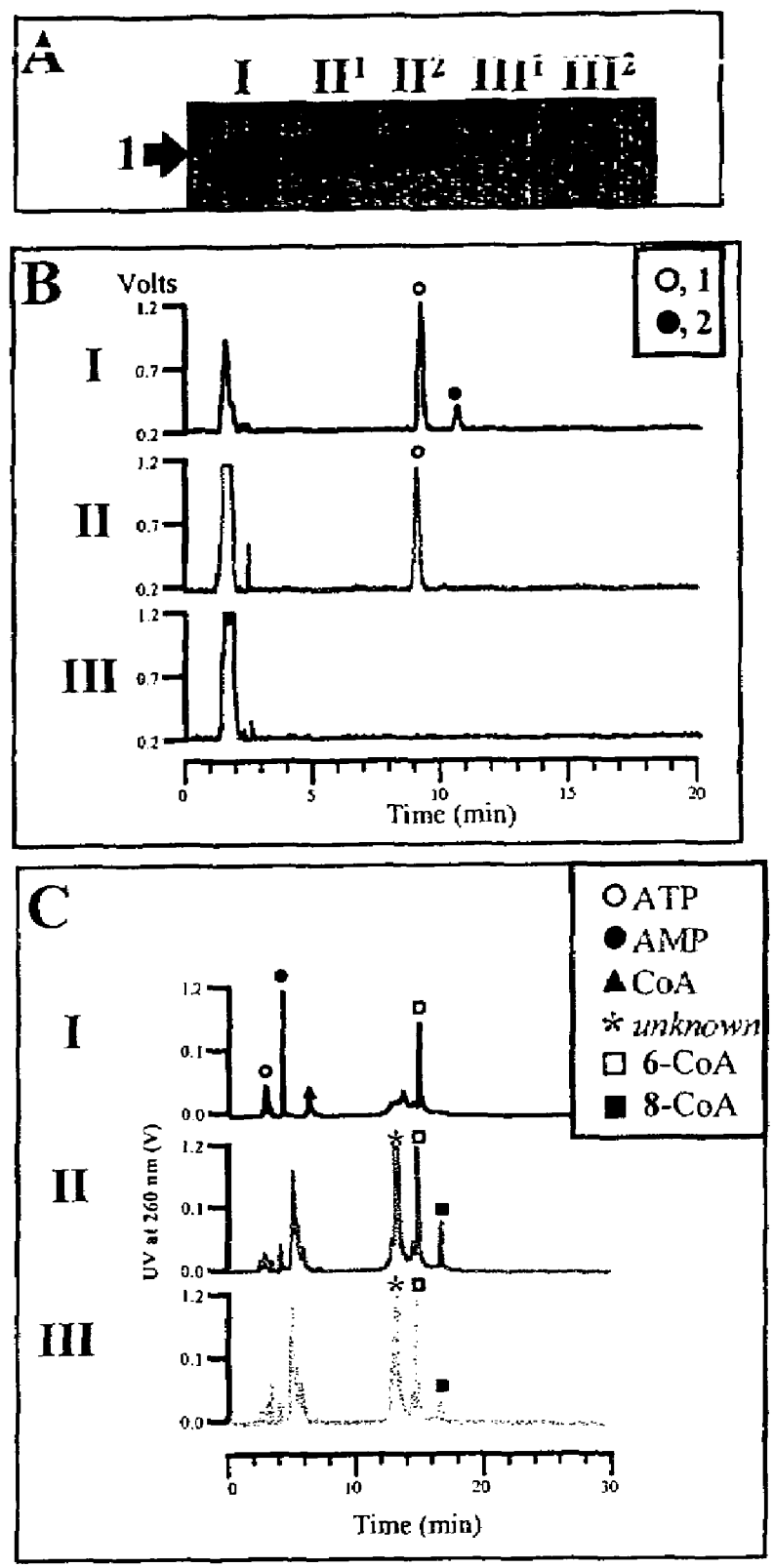
FIG. 13. Production of 1 from 6 assayed by TLC (A) and Evaporative Light-Scattering Detector (ELSD)-HPLC analysis (B) with authentic 1 and 6-CoA and 8-CoA (C) by NonL (C-I), *S. lividans* (pBS2048)-CFE (II), and *S. lividans* (pBS2049)-CFE (III), respectively. For A, II and III were conducted as duplicates. The CFEs were incubated with 2 mM each of ATP, CoA, and 6 for 1 h at 30° C.

To further evaluate this mechanism, it was decided to establish an in vitro conversion system that can readily convert (±)-6 into 1. For this purpose, ActIIORF4-activated actI/actIII promoter system was adopted to achieve concerted expression of the components, NonKJ. The NonKJL-expression plasmids were therefore constructed on pWHM467 and introduced into *S. lividans* for in vivo and in vitro assays; pBS2048 and pBS2049 were prepared for NonJ, NonL, and respectively for VSKEH-NonK and MGFCL-NonK for in vivo conversion experiments. While *S. lividans* (pBS2048) efficiently converted (±)-6 into 1, *S. lividans* (pBS2049) could not, defining that NonK is, at least as the catalyst supporting conversion of (±)-6 to 1, 462-aa protein with unusual N-teminal extension. Consistent with the in vivo feeding experiment, 1 was evident in the ethyl acetate extract of *S. lividans* (pBS2048)-CFE but not found from *S. lividans* (pBS2049)-CFE (FIG. 13AB). With *S. lividans* (pBS2048)-CFE, a 10% of yield was achieved for conversion of (±)-6 to 1 within 1 h. From both of *S. lividans* (pBS2047)-CFE and *S. lividans* (pBS2048)-CFE, 6-CoA and 8-CoA were found and a large excess of 6-CoA was accumulated compared to 8-CoA (FIG. 13C). The difference between results from *S. lividans* (pBS2045) (FIG. 12A-III) and *S. lividans* (pBS2048) (FIG. 13C-IV) was attributed to difference in the engineered transcriptional systems and whereby, the engineered actinorhodin promoters were viewed as rendering the concerted transcription of nonKJ. To further substantiate the roles of 6-CoA and 8-CoA in the nonactin biosynthesis, each compound was purified and incubated with *S. lividans*(pBS2048)-CFE and *S. lividans*(pBS2049)-CFE. 6-CoA and 8-CoA were collected from HPLC, freeze-dried and roughly quantified by using the known extinction coefficient of free coenzyme A (16,800 at 259.5 nm). When 6-CoA was incubated with *S. lividans* (pBS2048)-CFE, a small portion of 6-CoA could be seen intact, without any detectable level of 8-CoA, with accumulation of 1. Contrarily, in *S. lividans* (pBS2049)-CFE supplemented with 6-CoA, the comparable levels of 6-CoA and 8-CoA were found but 1 was not found. *S. lividans* (pBS2048)-CFE achieved quantitative conversion (≧50%) of either of 6-CoA (60 µM) or 8-CoA (40 µM) into 1 within 1 h. The efficient conversion of 8-CoA into 1 eventually disproved the intermediacy of trimeric 6-CoA but indicated 8-CoA is dimerized and subsequently cyclized to 1, by VSKEH-NonK.

Figure 14:
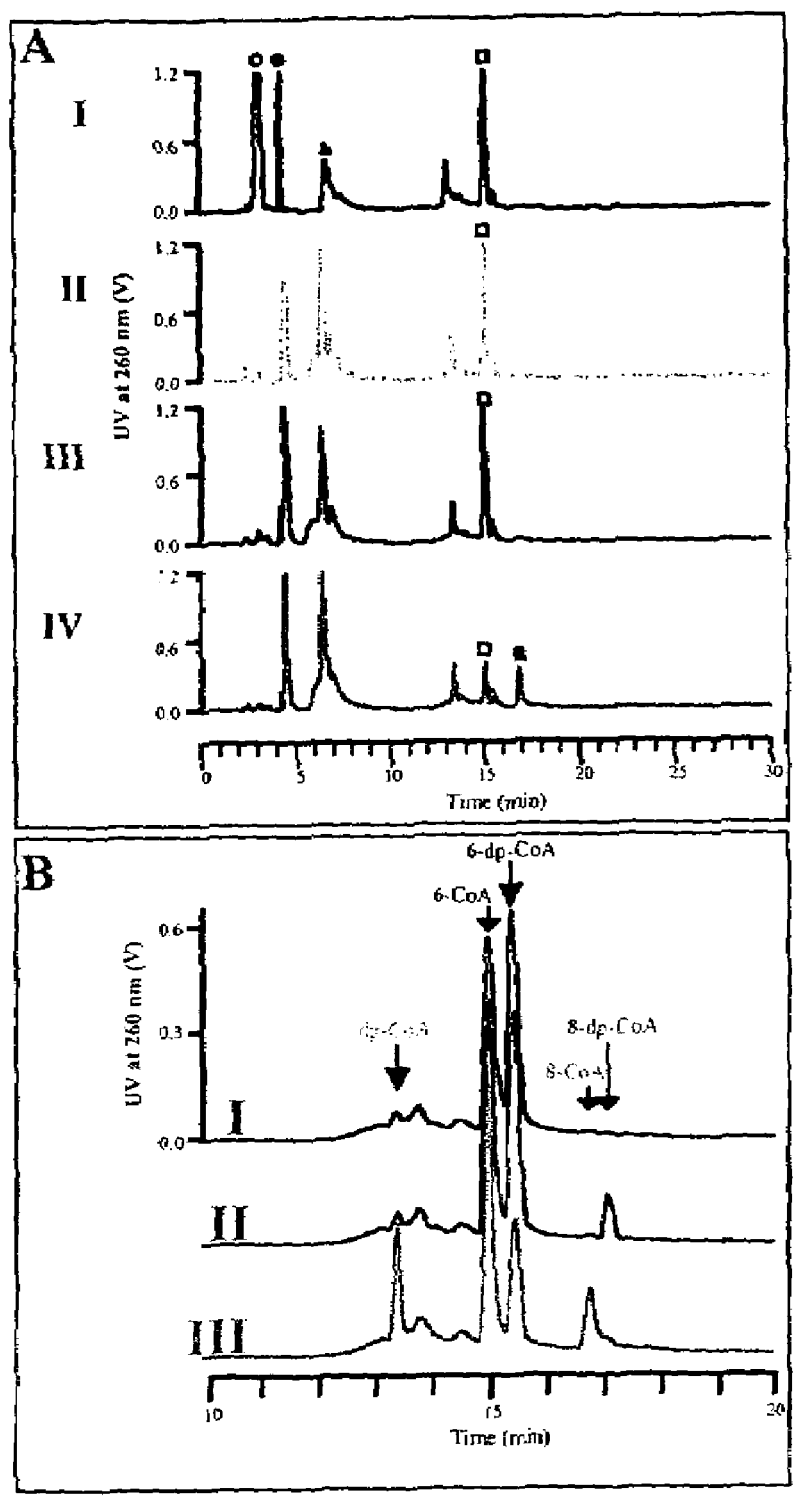
FIG. 14. (A) In vitro synthesis of 6-CoA (▣) and 8-CoA (▨) by *S. lividans* (pBS2054). NonL reaction prepared by 1 mM each of ATP, CoA, and 6 for 1 h at 30° C. (I) and supplemented with the CFEs of *S. lividans* (pWHM3) (II), *S. lividans* (pBS2053) (III), and *S. lividans* (pBS2054) (IV) and then maintained for additional 1 h at 30° C. (B) Formation of 6-CoA or 6-dp-CoA by *S. lividans* (pBS2054)-CFE incubated with 100 μM each of (−)-6-CoA and (−)-6-dp-CoA (I), (−)-6-CoA and (+)-6-dp-CoA (II), (+)-6-CoA and (−)-6-dp-CoA (III), for 1 h at 30° C.

To exclude any possibility that truncated NonK (MGFCL-NonK) or NonL charperoned NonJ-catalysis, nonJ alone was expressed in *S. lividans* and the resulting transformant was tested for the ability to convert 6-CoA to 8-CoA. Through PCR-amplication, nonK and nonJ were separately amplified and subcloned into pWHM3 downstream to ermE promoter generating pBS2053 and pBS2054, respectively. NonL was incubated with ATP, CoA, and 6 and then boiled for enzyme inactivation. When this NonL-reaction mixture was used, production of 8-CoA was evident with *S. lividans* (pBS2054)-CFE but not with *S. lividans* (pBS2053)-CFE (FIG. 14A). It should be noted that two molecules of 6-CoA are consumed to form one molecule of 8-CoA, assuring that NonJ is enough to convert 6-CoA to 8-CoA and NonK and NonL has no relevant role in this conversion process. The production of 1 can be achieved by incubating 8-CoA with *S. lividans*(pBS2053)-CFE, which further assured the sequential catalysis of NonJ and NonK. However, the activity of *S. lividans*(pBS2053)-CFE was significantly compromised compared to *S. lividans* (pBS2048), which provided the possibility of NonJ-chaperoning on NonK catalysis. The CFE of *E. coli* BL21 (pBS2047) showed efficient NonK activity comparable to that of *S. lividans* (pBS2048) although it possesses just a trace level of NonJ activity (FIG. 12A-IV). As a purely genetic concept, the inventors could conceive that the integrity of nonK required nonJ sequence on its downstream for its proper expression to NonK, for which there is apparently no clear explanation in the biochemical level, however. Alternatively, and more plausibly, a catalytic role of NonJ in NonK-catalysis can be envisioned; that is, NonJ takes up again 8 from 8-CoA and directs transfer of 8 onto the nucleophile of NonK similar to what has been proposed in aflatoxin biosynthesis.

Figure 11:
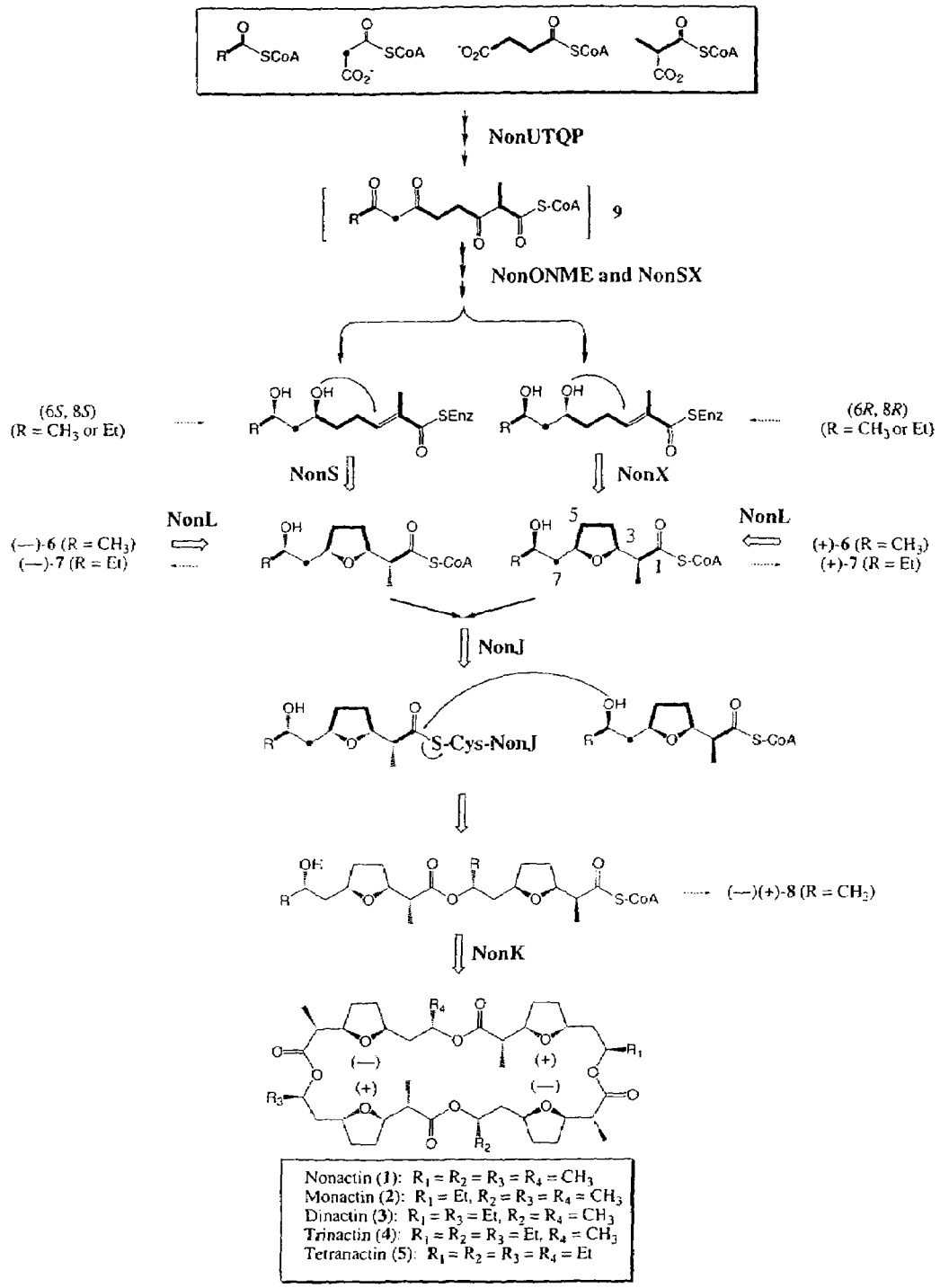
FIG. 11. Biosynthetic pathway of macrotetrolides in *S. griseus*. Arrows with broken lines indicate intermediates that have been isolated or confirmed by feeding experiments. The macrotetramerization process is catalyzed by NonL, NonJ, and NonK.

The inventors then addressed the question of what is NonJ's stereospecificity toward the substrates, (−)-6-CoA and (+)-6-CoA. (+)-6-CoA or (−)-6-CoA was readily generated from cognate enantiomeric 6 by NonL with the same efficiency in the overall turn-over, which verified that NonL operates in the nonstereospecific manner as aforementioned. The deduced mechanism for NonJ catalysis is as follows: one enantiomeric 6-CoA donates a 6-moiety to the cysteine nucleophile of NonJ and a terminal hydroxyl group from the other enantiomeric 6-CoA replaces the active site nucleophile to generate 8-CoA. That is, the thioesteric linkage of one enantiomeric 6-CoA acts as a leaving group and the CoA-moiety of the other enantimeric 6-CoA is maintained in 8-CoA(FIG. 11). Therefore, to differentiate fates of (−)-6-CoA and (+)-6-CoA, the investors labeled CoA-moieties of (−)-6-CoA and (+)-6-CoA differentially, by employing enantiopure 6 in a NonL reaction. To achieve this, the inventors reviewed the known CoA biosynthetic pathway and found that the ultimate intermediate to CoA is 3'-dephospho-CoA (dp CoA), which is commercially available. The formation of 6-dp-CoA and 6-dp-CoA was carried out by employing purified NonL and the CFE containing NonJ. It was then demonstrated that dp-CoA can be converted into 6-dp-CoA by NonL with efficiency comparable to that with CoA and *S. lividans* (pBS2054)-CFE also converted 6-dp-CoA into 8-dp-CoA whose identity was verified by detecting molecular ion (m/e for [M−H]⁻) of 1054.368 ($C_{41}H_{66}N_7O_{19}SP_2$, calcd 1054.361). With dp-CoA to replace CoA in NonL and NonJ catalysis, (−)-6-dp-CoA, (+)-6-dp-CoA, (−)-6-CoA, and (+)-6-CoA were separately prepared and incubated (100 μM each) with *S. lividans* (pBS2054)-CFE. HPLC analysis revealed that incubation of (−)-dp-6-CoA with (+)-6-CoA resulted in 8-CoA, whereas (−)-6-CoA with (+)-dp-6-CoA resulted in 8-dp-CoA (FIG. 13B). A notable feature found in the (−)-dp-6-CoA/(+)-6-CoA-incubation was that (−)-dp-6-CoA was consumed remarkably higher than (+)-6-CoA, which was attributed to hydrolysis of (−)-dp-6-CoA activated by the presence of (+)-6-CoA but uncoupled with formation of 8-CoA. The NonJ-catalysis was defined as stereoselective, in which (−)-6 was loaded onto the active site nucleophile that is replaced by terminal hydroxyl group of (+)-6-CoA to generated (−)-6-(+)-6-CoA. This experiment showed that (+)-6-(+)-6-CoA also can be generated by NonJ with four fold less efficiency of that of (−)-6-(+)-6-CoA, whereas no trace of (−)-6-(−)-6-CoA can be generated. The (+)-6-(+)-6-CoA apparently can not lead to 1 as evident from the established structure of 1 and other CFE-conversion experiments. It seems therefore evident that NonK discriminates (+)-6-(+)-6-CoA in the oligotetramerization/cyclization process.

NonJK are unique KSs that catalyze C—O bond formation. By exploiting the in vitro assay system, and CoA-derivatives, 6-CoA and 8-CoA were defined as direct substrates for NonJ and NonK catalysis, respectively. This feature was originally suggested by the absence of ACP in the macrotetrolide gene cluster and here verified by efficient conversion of 6-CoA into 8-CoA which then lead to 1 in vitro. So far, KSs directly accepting directly acyl-CoAs are known to have a primary structure clearly distinguishable from ACP-dependent ones. NonJK definitely belong to ACP-dependent KSs in the primary sequence analysis but here they are established as ACP-independent ones, demonstrating that catalytic mechanism (ACP-dependent or -independent) is surprisingly not related to the observed primary sequence features. Furthermore, the nucleophiles in condensations of NonJ and NonK are complex acyl group (6 and 8) other than malonyl group that is the general nucleophile in type II PKS and FAS and type III PKS (in the case of type III PKS, incoporation of methylmalonyl group occurs exceptionally). Furthermore, the inventors have demonstrated that NonJ and NonK work in a processive manner instead of in an iterative manner as that known for their homologues in type II and type III PKSs.

Materials and methods related to the characterization of nonJKL genes described in the foregoing section are presented below:

Plasmid preparation: The relevant NonKJ sequences were amplified from pBS2019 by Vent polymerase (NEB, Beverly, Mass.) with forward primer 5'-TGGACGCGGGGC<u>CATATG</u>AGCAAGAG-3' (SEQ ID NO:14) (the NdeI site is underlined) for VSKEH-NonK or 5'-CGCGCTGGTCACC<u>CATATG</u>GGGTTCTGC-3' (SEQ ID NO:15) (the NdeI site is underlined) for MGFCL-NonK and reverse primer of 5'-GC-CGCGTCGCC<u>ATGCATT</u>GAACGTGGGT-3' (SEQ ID NO:16) (the NsiI site is underlined) and cloned as a 2.7-kb or 2.6-kb NdeI-NsiI fragment into the same of pGEM-5zf (Promega, Madison, Wis.) generating pBS2041 and pBS2042. The nonLS was subcloned from pBS2003 as a 4.2-kb KpnI-HincII fragment into the sames of pUC18. From the resulting plasmid, the insert was rescued as EcoRI-HindIII fragment and subcloned into the sames of Lithmus 28 generating pHJK-3-45D. The inserts of pBS2041 and pBS2042 were rescued as SpeI-NsiI fragment and subcloned into sames of pHJK-3-45D to generate pBS2043 and pBS2044, respectively. The insert of pBS2044 was rescued as NdeI-BglII fragment and ligated into NdeI-BamHI sites of pIJ4123 to generate pBS2045.

The NdeI-BglII fragments including nonKJL were rescued from pBS2043 and pBS2044, respectively, and subcloned into NdeI and BamHI sites of pET28a (Novagen, Madison, Wis.) generating pBS2046 and pBS2047. The inserts of pBS2046 and pBS2047 were recovered as XbaI-NsiI fragments and subcloned into pHJK-3-97A, a pWHM467 derivative to which the unique BglII site was engineered downstream to PacI site to generate pHJK-4-07E and pHJK-4-07F, respectively. The nonDL sequence was rescued as PacI-BglII fragment from pBS2016 and subcloned into sames of pHJK-4-07E and pHJK-4-07F, respectively, to generate pBS2048 (pHJK-4-10A) and pBS2049 (pHJK-4-10B).

The nonK sequence was amplified from pBS2019 by Vent polymerase with forward primer of 5'-CCTCAGGC<u>CCATGG</u>TC<u>TAGA</u>GCACCATCCTGCGGCGCCTG-3' (SEQ ID NO:17) (the NcoI and XbaI sites are underlined) and reverse primer of 5'-GCAGAGGCAGATCTGCAGA-CATCGCCACCTCCCA-3' (SEQ ID NO:18) (the BglII site is underlined). The nonJ was amplified from pBS2019 by Vent polymerase with forward primer of 5'-GACCCCGT CCATGGTCTAGACATTCGACCCGGTCCCCGGC-3' (SEQ ID NO:19) (the NcoI and XbaI sites are underlined) and reverse primer of 5'-GTGAACGT AGATCTTGGCAAGTCGCCGCCTTCGT-3' (SEQ ID NO:20) (the BglII site is underlined). The PCR products were purified as NcoI-BglII fragment and subcloned into the sames of pQE60 generating pBS2050 (pHJK-4-16C) (nonK) and pBS2051 (pHJK-4-16D) (nonJ).

The ermE promoter DNA (EMBL accession number X02392 for ermE) was recovered as a 300-bp KpnI-BamHI fragment from pIJ2925 and subcloned into pUC18 generating pBS2052 (pHJK-4-15A). The insert of pBS2050 (nonK) or pBS2051 (nonJ) was recovered as XbaI-HindIII fragments and the ermE promoter was rescued as an EcoRI-XbaI fragment from pBS2052, both of which were ligated into EcoRI and HindIII sites of pWHM3 to generate pBS2053 and pBS2054, respectively for nonK and nonJ expression.

Nickel affinity chromatography: SDS (sodium dodecyl sulfate)-PAGE (polyacrylamide gel electrophoresis) analysis of *S. lividans* (pBS2045)-cell extract showed, in insoluble fraction, a strong protein band around 45-kDa that was absent from controls such as that of *S. lividans*(pIJ4123) with thiostrepton-supplementation or *S. lividans* (pBS2045) before thiostrepton-supplementation. It was conceived that the highly expressed insoluble protein was MGFCL-NonK based on the size of 6×histidine-tagged-MGFCL-NonK as seen in *E. coli*BL21 (pBS2047). In the soluble fraction was observed protein-enrichment, unresolved, around 45 to 50-kDa. Neither relevant activities (such as formation of 6-CoA and its oligomerization) nor protein(s) around 45 to 50-kDa was retained on the nickel affinity chromatography even in the modified condition.

The inserts of pBS2043 and pBS2044 were also subcloned into pET28a to generated pBS2046 and pBS2047. The expression experiment in *E.coli* showed that both versions of NonK were well expressed, without any relevant protein bands for NonJ or NonL, but largely insoluble and somehow, not compatible to the nickel affinity chromatography. It could not be determined whether the failure was simply due to inability of 6×histidine-tagged-NonKs to interact with nickel or their intrinsic instability during the chromatographic procedure.

Cell-free extract (CFE) preparation: *S. lividans* (pBS2045) were grown on Yeast Extract-Malt Extract (YEME, 34% sucrose) media supplemented with kanamycin (50 µg/ml), at 30° C. and 300 rpm for 1 d and added with thiostrepton (5 µg/ml). The thiostrepton-treated culture was maintained in the same condition for 1 d and then harvested by centrifugation (13,600 g, 20 min, 4° C.). Cell were lysed in 30 ml of 100 mM sodium phosphate buffer (pH, 8.0)-1 mM EDTA-50 mM KCl-10% glycerol with lysozyme (2 mg/ml) for 30 min at 4° C., sonicated for thirty 10-sec bursts at 300 W with a 30-sec cooling period between each burst. Centrifugation (27,500 g, 20 min, 4° C.) yield a clear supernant that was further brought to 70% saturation of $(NH_4)_2SO_4$ and centrifuged as above to the collect pellet. The pellet was dissolved in 20 mM Tris-Cl (pH, 8.0)-10 mM $MgCl_2$-2 mM DTT-10 mM KCl-10% glycerol and desalted on Sephadex G-25 column to yield the cell-free preparation (7 to 10 mg/ml proteins). The CFEs of *S. lividans*(pBS2047) and *S. lividans* (pBS2048) were prepared at the same procedure except that they were grown on 25 ml-AP media, supplemented with thiostrepton (5 µg/ml), at 30° C. and 300 rpm for 3 ds. Similarly, the CFEs of *S. lividans* (pBS2053) and *S. lividans* (pBS2054) were prepared by using mycelium from YEME (34% sucrose) cultures.

Conditions for CFE-assay and chemical analysis: The assay solution consisted of 1 to 2 mM each of (±)-6, CoA, and ATP and 0.8 mg/ml of protein in 10 mM Tris-Cl (pH, 8.0)-10 mM KCl-2 mM DTT-5 mM $MgCl_2$, and incubated at 30° C. for 1 h to 3 hs. The incubation was terminated by ethyl acetate extraction. The organic layer was analyzed for 1 by Thin-Layer Chromatography (TLC), Evaporative Light-Scattering Detector (ELSD)-High Performance Liquid Chromatography (HPLC), and positive Matrix-Assisted Laser Desorption Ionization (MALDI)-Mass Spectrometry (MS) analysis as previously described.[5d] The aqueous layer was analyzed by HPLC with UV-detection, from which relevant peaks were collected and subjected to negative MALDI-MS analysis. HPLC with UV-detection was performed on an Alltima C18 column (4.6×250 mm, 5µ, 100 Å, Alltech, Deerfield, Ill.). The column was first eluted in 5% $CH_3CN$ in 20 mM $NH_4Ac$, pH 5.8 (buffer A) for 7 min, followed by linear gradients from 100% buffer A to 50:50 of (buffer A:$CH_3CN$) for 8 min, from 50:50 of (buffer A:$CH_3CN$) to 10:90 of (buffer A:$CH_3CN$) and then maintained for additional 10 min, except for the result in FIG. 12A for which the elution was maintained after reach to 50% $CH_3CN$, with flow rate of 1.0 ml/min at 260 nm. MALDI-MS analysis was performed on a HiResMALDI FT-Mass Spectrometer with 7 tesla superconducting magnet (IonSpec Corp., Irvine, Calif.) at the Analytical Instrumentation Facility of School of Pharmacy, University of Wisconsin, Madison.

Non-strereoselective features in NonJ catalysis: The eluent from 8-CoA and 8-dp-CoA was collected from HPLC and analyzed by MS analysis, which confirmed their identities. The finding from mass spectra is that 8-dp-CoA molecular ion was found as a 25% rel. int. of 8-CoA in (−)-dp-6-CoA/(+)-6-CoA and vice versa, 8-CoA found as a 5% rel. int. of 8-dp-CoA in (+)-dp-6-CoA/(−)-6-CoA. Roughly, 8-dp-CoA is two times sensitive as 8-CoA in the MS analysis, which projected that about 10% of 8-CoA has the stereochemistry [(+)-(−)-CoA] opposite to that of major product, (−)-6-(+)-6-CoA. However, it should be also questioned whether the intensities on mass spectra do linearly correlate to the actual concentration of the specific molecule.

NonJ also can form (+)-6-(+)-6-CoA. NonJ accumulated significant level of 8-CoA or 8-dp-CoA from (+)-6 incubation with ATP and CoA/dp-CoA in *S. lividans* (pBS2045) and (+)-6-CoA and/or (+)-6-dp-CoA in *S. lividans*(pBS2048). Although the kinetic values for (−)-6-(+)-6-CoA and (+)-6-(+)-6-CoA were not determined, the formation of (−)-6-(+)-6-CoA or (−)-6-(+)-6-dp-CoA was observed to be two to four fold higher than that of (+)-6-(+)-6-CoA or (+)-6-(+)-6-dp-CoA in the overall turnover.

D. Creation of Chemical Diversity by Utilizing NonJK in Directed Biosynthesis.

Elements (e.g., open reading frames) of the nonactin biosynthetic gene cluster, namely, nonJ, nonK, nonJK or nonJKL or variants thereof, can be used in a wide variety of "directed" biosynthetic processes (where the process is designed to modify and/or synthesize one or more particular preselected target molecule(s). Variants may include complete or partial open reading frames such as those encompassing active catalytic sites, and the like. In particular, the nonJKL open reading frames can be used to synthesize a macrotetrolide or a macrotetrolide analogue. The combination of nonJKL open reading frames can be used to direct the synthesis of various macrotetrolides from starting products exemplified by 3 in FIG. 5C.

In addition, polypeptides from nonJ or nonK open reading frames, taken individually, can be used to perform chemical modifications on particular substrates and/or to synthesize various metabolites. Thus, for example, polypeptides of nonJ or nonK can be used to catalyze a C—O bond in a biological molecule appropriate as a substrate for the particular polypeptide whereby a C—O bond is catalyzed in intermolecular or intramolecular fashion within the biological molecule or between the biological molecule and a second biological molecule. One of skill in the art, utilizing the information provided here, can perform literally countless chemical modifications and/or syntheses using either "native" macrotetrolide biosynthesis metabolites as the substrate molecule, or other molecules capable of acting as substrates for the particular polypeptide. Other substrates can be identified by routine screening. Methods of screening enzymes for specific activity against particular substrates are well known to those of skill in the art.

The biosyntheses can be performed in vivo, e.g. by providing a host cell comprising the desired nonJKL open reading frames (taken individually or in combination) or in vitro, e.g., by providing the polypeptides encoded by the selected nonJKL ORFs and the appropriate substrates and/or cofactors. One of skill in the art may also combine the catalytic domains of NonJK, individually or in combination, with other different catalytic domains so as to form a hybrid enzyme or megasynthetase possessing various catalytic domains useful in synthesizing predicted structures.

In one embodiment, this invention provides for the synthesis of macrotetrolides and/or macrotetrolide analogues or derivatives. In a preferred embodiment, this is accomplished by providing a cell comprising purified nonJKL ORFs and culturing the cell under conditions whereby the desired macrotetrolide or macrotetrolide analogue is synthesized. The cell can be a cell that does not normally synthesize a macrotetrolide and nonJKL ORFs can be transfected into the cell (i.e., a heterologous host). Alternatively, a cell that typically synthesizes macrotetrolides can be utilized and all or part of the nonJKL ORFs can be introduced into the cell. Macrotetrolide derivatives/analogues can be produced by changing the host cell (e.g. to a eukaryotic cell that glycosylates the biosynthetic product), and/or by providing altered metabolites.

The use of standard techniques of molecular biology (gene disruption, gene replacement, gene supplement) can be used to modulate and/or otherwise alter macrotetrolide and/or other metabolite production in an organism that naturally synthesizes a macrotetrolide or an organism that is modified to synthesize a macrotetrolide.

Alternatively, control sequences that alter the expression of various open reading frames can be introduced that alter the amount and/or timing of macrotetrolide production. Thus, for example, by placing particular nonJKL open reading frames under control of a constitutive promoters known in the field, macrotetrolide production may be increased.

Figure 4:
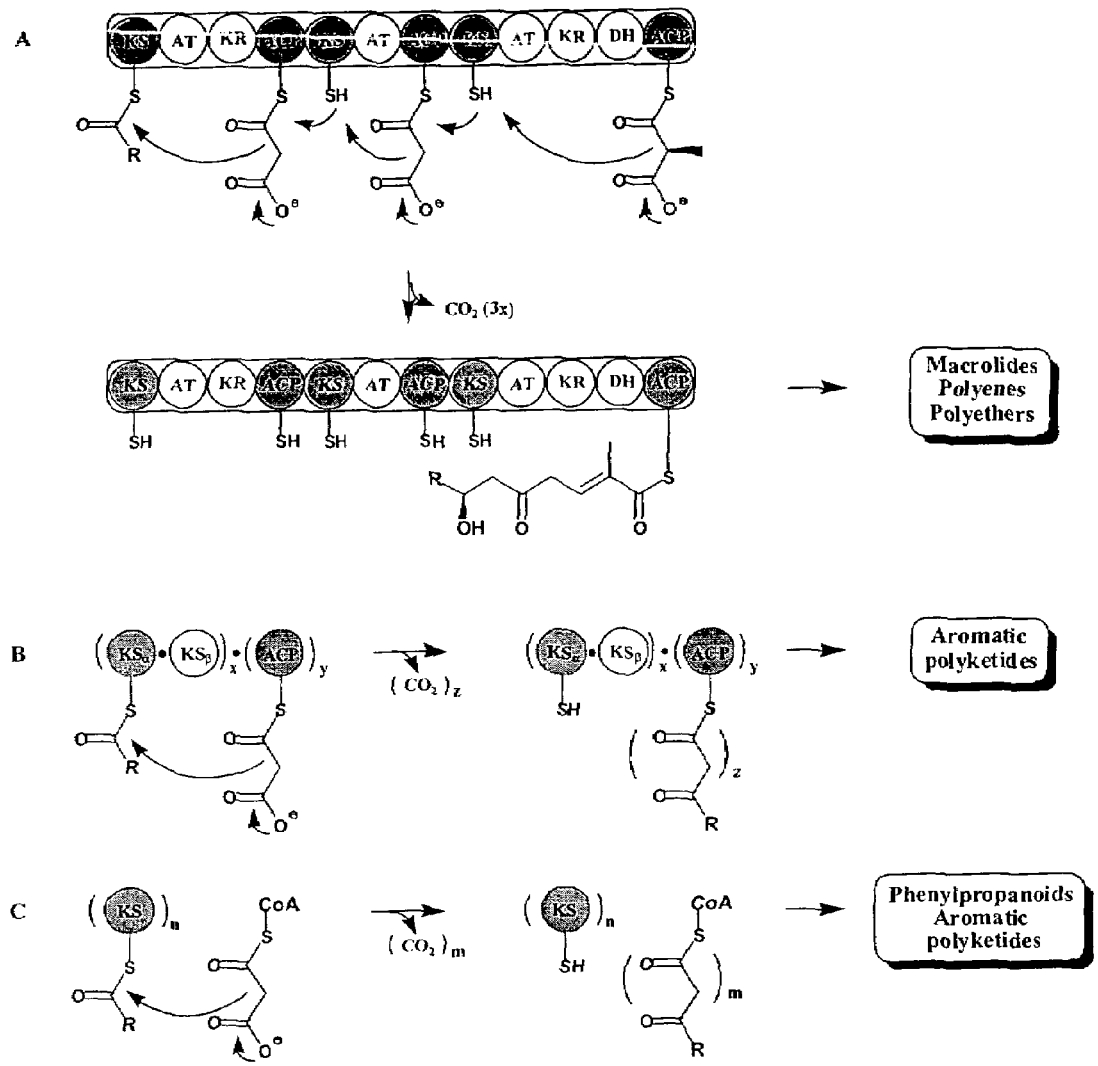
FIG. 4. Structures and mechanisms of bacterial polyketide synthases. (A) Type I PKS consists of noniteratively acting domains, (B) type II PKS consists of iteratively acting subunits, and both types utilize ACP to activate substrates and channel intermediates. (C) Type III PKS consists of iteratively acting single subunit and utilizes acyl CoA directly as substrates. Domains or subunits shown are hypothetic. "x", "y", and "n" emphasize the stoichiometry of subunits. The KSα and KSβ subunits in solution exist as a $\alpha_2\beta_2$ heterotetramer for the actinorhodin PKS and as a αβ heterodimer for the tetracenomycin PKS. The stoichiometric relationship between KSα/KSβ and ACP subunits is unknown. The stoichiometry for type III PKS of bacterial origin is unknown although two type III PKS from plants have been determined to be homodimers. "z" and "m" indicates the number of cycles the starter unit is elongated by the extender units to afford the full-length polyketide products. ACP, acyl carrier protein; AT, acyl transferase; DH, dehydratase; ER, enoyl reductase; KR, ketoreductase; KS, ketoacyl synthase.
Figure 5:
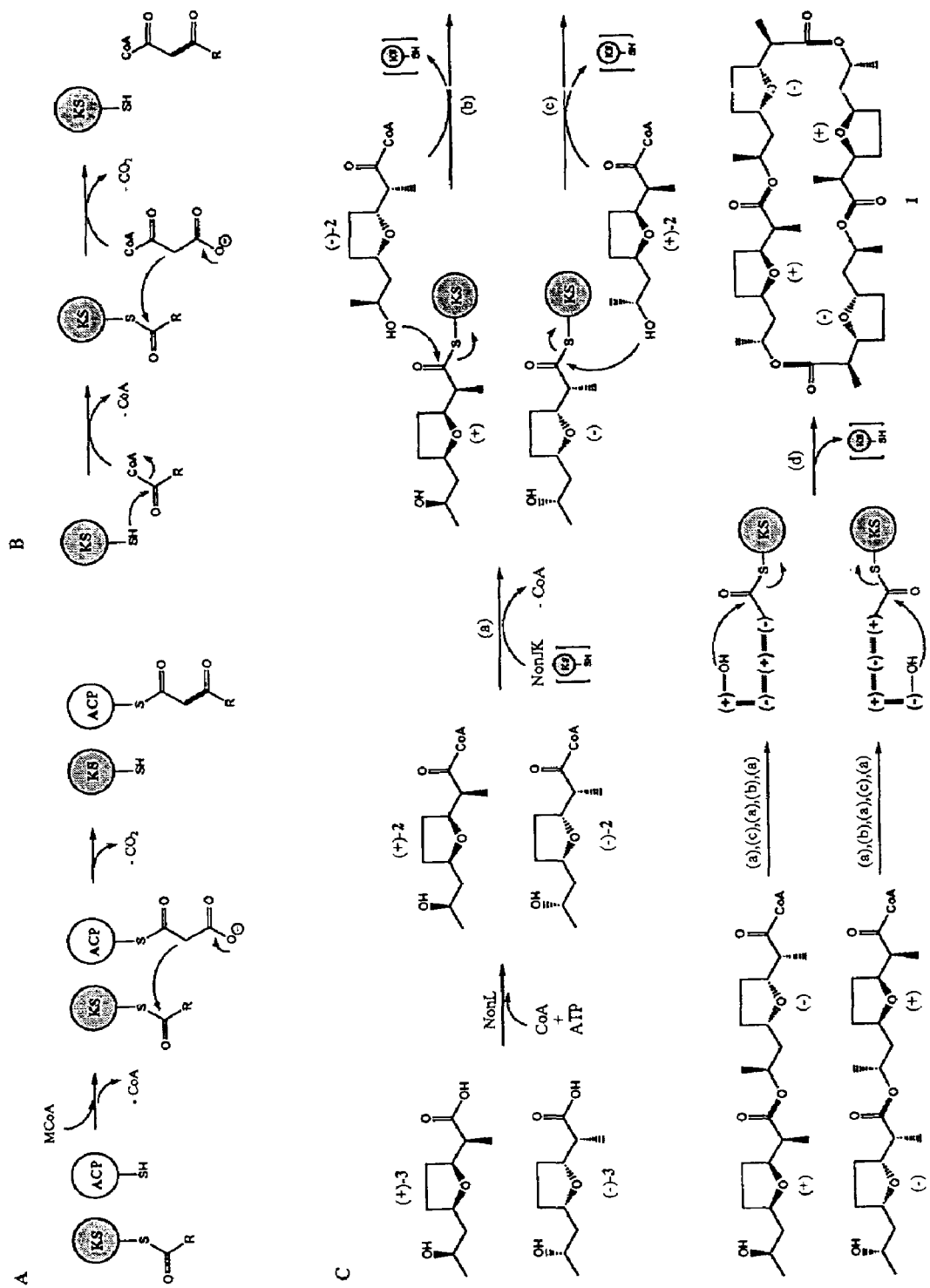
FIG. 5. C—C bond-forming step catalyzed by (A) type I and -II PKSs and (B) type III PKSs and (C) C—O bond-forming steps generally catalyzed by the NonJK KSs. KS, β-ketoacyl synthase; ACP, acyl carrier protein; CoA, coenzyme A; MCoA, malonyl CoA.

In addition to the directed modification and/or biosynthesis of various metabolites as described above, the nonJKL open reading frames can be utilized, individually or as a module, in combination with other biosynthetic modules (e.g. nonriboromal polypeptide sythetases (NRPS) and/or PKS modules and/or enzymatic domains of other PKS and/or NRPS systems) to produce a wide variety of compounds including, but not limited to various macrotetrolides, macrotetrolide derivatives, polyketides, polypeptide derivatives, or polyketide/polypeptide hybrids. General information on modular constructs may be found in Cane et al., Chemistry & Biology, 1999, Vol. 8, No. 12, pps 319-325 and Cane et al., Science, Vol. 282, pps 63-68. The preceding two cited articles are incorporated by reference in their entirety for all purposes. In the present context, the term "module" or "modularity," refers to coordinated groups of active sites in large, multifunctional proteins in which each coordinated group, or module, is responsible for a particular catalysis step as exemplified by a polypeptide chain elongation as illustrated in FIGS. 4-5. Well known modular genetic methodology may be used to alter the number, content, and order of such modules and, in doing so, alter rationally the structure of the resultant products. Entirely unnatural products may thusly be generated.

Target products can be produced, in vivo or in vitro, by catalytic biosynthesis using combinations of modules from PKSs, NRPSs, and hybrid PKS/NRPS systems, commonly termed megasynthetases. In a preferred embodiment large combinatorial libraries of cells harboring various megasynthetases can be produced by random or directed modification with subsequent selection for the production of a target molecule or molecules of interest. It will be appreciated that, in certain embodiments, such libraries of megasynthetases, can be used to generate large, complex combinatorial libraries of compounds which themselves can be screened for a desired activity.

In numerous embodiments of this invention, novel molecules, may be created by modifying the nonJKL ORFs so as to introduce variations into metabolites synthesized by the enzymatically-active polypeptides. Such variations may be introduced by design, for example to modify a known molecule in a specific way, e.g. by replacing a single monomeric unit within a polymer with another, thereby creating a derivative molecule of predicted structure. Such variations can also be made by adding one or more modules or enzymatic domains to a known PKS, or by removing one or more module from a known PKS.

Furthermore, it is possible to introduce variant nonJKL domains or modules into a megasynthetase. Mutations can be made to the native nonJKL subunit sequences and such mutants used in place of the native sequence, so long as the mutants are able to function with other subunits (domains or modules) in the synthetic pathway. Such mutations can be made to the native sequences using conventional techniques such as by preparing synthetic oligonucleotides including the mutations and inserting the mutated sequence into the gene encoding a subunit using restriction endonuclease digestion. (see, e.g., Kunkel, (1985) *Proc. Natl. Acad. Sci. USA* 82: 448; Geisselsoder et al. (1987) *BioTechniques* 5: 786). Alternatively, the mutations can be effected using a mismatched primer (generally 10-20 nucleotides in length) which hybridizes to the native nucleotide sequence (generally cDNA corresponding to the RNA sequence), at a temperature below the melting temperature of the mismatched duplex. The primer can be made specific by keeping primer length and base composition within relatively narrow limits and by keeping the mutant base centrally located (Zoller and Smith (1983) *Meth, Enzymol.* 100: 468). Primer extension is effected using DNA polymerase, the product cloned and clones containing the mutated DNA, derived by segregation of the primer extended strand, selected. Selection can be accomplished using the mutant primer as a hybridization probe. The technique is also applicable for generating multiple point mutations (see, e.g., Dalbie-McFarland et al. (1982) *Proc. Natl. Acad. Sci USA* 79:6409). PCR mutagenesis will also find use for effecting the desired mutations.

In another embodiment, variations can be made randomly, for example by making a library of molecular variants by randomly mutating one or more elements of the nonJKL genes or by randomly replacing one or more open reading frames of nonJKL genes with one or more of alternative open reading frames.

As can be realized from the foregoing, the various open reading frames can be combined into a single multi-modular megasynthetase thereby dramatically increasing the number of possible combinations obtained using these methods. These combinations can be made using standard recombinant or nucleic acid amplification methods, for example by shuffling nucleic acid sequences encoding various modules or enzymatic domains to create novel arrangements of the sequences, analogous to DNA shuffling methods described in Crameri et al. (1998) *Nature* 391: 288-291, and in U.S. Pat. No. 5,605,793 and in U.S. Pat. No. 5,837,458. In addition, novel combinations can be made in vitro, for example by combinatorial synthetic methods. Novel molecules or molecule libraries, can be screened for any specific activity using standard methods.

Random mutagenesis of the nucleotide sequences obtained as described above can be accomplished by several different techniques known in the art, such as by altering sequences within restriction endonuclease sites, inserting an oligonucleotide linker randomly into a plasmid, by irradiation with X-rays or ultraviolet light, by incorporating incorrect nucleotides during in vitro DNA synthesis, by error-prone PCR mutagenesis, by preparing synthetic mutants or by damaging plasmid DNA in vitro with chemicals. Chemical mutagens include, for example, sodium bisulfite, nitrous acid, hydroxylamine, agents which damage or remove bases thereby preventing normal base-pairing such as hydrazine or formic acid, analogues of nucleotide precursors such as nitrosoguanidine, 5-bromouracil, 2-aminopurine, or acridine intercalating agents such as proflavine, acriflavine, quinacrine, and the like. Generally, plasmid DNA or DNA fragments are treated with chemicals, transformed into *E. coli* and propagated as a pool or library of mutant plasmids.

Large populations of random enzyme variants can be constructed in vivo using "recombination-enhanced mutagenesis." This method employs two or more pools of, for example, $10^6$ mutants each of the wild-type encoding nucleotide sequence that are generated using any convenient mutagenesis technique, described more fully above, and then inserted into cloning vectors.

In either the directed or random approaches, nucleic acids encoding novel combinations of genes are introduced into a cell. In one embodiment of the present invention, nucleic acids encoding the nonJ, nonK, nonJK or nonJKL open reading frames are introduced into a cell so as to replace one or more open reading frames of an endogenous gene cluster within a cell. Endogenous gene replacement can be accomplished using standard methods, such as homologous recombination. In a preferred embodiment, such nucleic acids are introduced into the cell optionally along with a number of additional genes, together called a 'modified gene cluster,' that influence the expression of the genes, survival of the expressing cells, etc. In a particularly preferred embodiment, such cells do not have any other macrotetrolide and/or PKS encoding genes or gene clusters, thereby allowing the straightforward isolation of the molecule(s) synthesized by the genes introduced into the cell.

Furthermore, the recombinant vector(s) can include genes from a single nonactin gene cluster, or may comprise hybrid replacement PKS gene clusters with, e.g., a gene for one cluster replaced by the corresponding gene from another polyketide gene cluster. For example, it has been found that ACPs are readily interchangeable among different synthases without an effect on product structure. Furthermore, a given KR can recognize and reduce polyketide chains of different chain lengths. Accordingly, these genes are freely interchangeable in the constructs described herein. Thus, the replacement clusters of the present invention can be derived from any combination of PKS and gene sets that ultimately function to produce an identifiable polyketide.

Examples of hybrid replacement clusters include, but are not limited to, clusters with genes derived from two or more of the act gene cluster, the whiE gene cluster, frenolicin (fren), granaticin (gra), tetracenomycin (tcm), 6-methylsalicylic acid (6-msas), oxytetracycline (otc), tetracycline (tet), erythromycin (ery), griseusin (gris), nanaomycin, medermycin, daunorubicin, tylosin, carbomycin, spiramycin, avermectin, monensin, nonactin, curamycin, rifamycin and candicidin synthase gene clusters, among others. (For a discussion of various PKSs, see, e.g., Hopwood and Sherman (1990) *Ann. Rev. Genet.* 24: 37-66; O'Hagan (1991) The Polyketide Metabolites, Ellis Horwood Limited.

A number of hybrid gene clusters have been constructed, having components derived from the act, fren, tcm, gris and gra gene clusters (see, e.g., U.S. Pat. No. 5,712,146). Other hybrid gene clusters, as described above, can easily be produced and screened using the disclosure herein, for the production of identifiable polyketides, polypeptides.

Host cells (e.g. *Streptomyces*) can be transformed with one or more vectors, collectively encoding a functional PKS system, or a cocktail comprising a random assortment of polyketide-related ORFs genes, modules, active sites, or portions thereof. The vector(s) can include native or hybrid combinations of such molecules, or mutants thereof. As explained above, the gene cluster need not correspond to a complete native gene cluster but need only encode the necessary PKS system components to catalyze the production of the desired product(s).

In addition to varying the nucleic acids comprising the subject gene cluster, variations in the products produced by the gene cluster(s) can be obtained by varying the the host cell, the starter units and/or the extender units. Thus, for example different starter units can be utilized in the synthetic pathway resulting in different polyketide or target molecule variants. Similarly different intermediate metabolites can be provided (e.g. endogenously produced by the host cell, or produced by an introduced herterologous construct, and/or supplied from an exogenous source (e.g. the culture media)). Similarly, varying the host cell can vary the resulting product(s). For example, a gene cassette carrying the nonJKL biosynthesis genes can be introduced into a deoxysugar-synthesizing host for the production of glycosylated polyketide metabolites.

Before describing an example of the production of unnatural macrotetralides according to the invention, the inventors' foregoing results will be summaried. In brief, the macrotetrolide biosynthetic gene cluster from *Streptomyces griseus* DSM40695 was characterized to encode type II polyketide synthase (PKS) composed of five β-ketoacyl synthases (KSs), four ketoreductase (KRs), two enoyl-coenzyme A(CoA) hydratase (ECH) homologs, and a CoA transferase. The most characteristic feature of the macrotetrolide biosynthetic cluster was the absence of an ACP, which introduced a new type II PKS system working directly on acyl-CoA intermediates. A series of gene inactivation experiments confirmed that all the key components aforementioned play critical roles in the macrotetrolide biosynthesis. The heterologous expression study in *S. lividans* identified a genetic locus responsible for macrotetrolide production, in which two KSs of NonJK catalyze macrotetralization of (±)-6-CoA and NonL, a CoA ligase converts (±)-6 into (±)-6-CoA. A cell-free extract (CFE) study further guided the inventors to define NonJK-catalysis to include NonJ converting 6' into (−)-6-(+)-6-CoA (6") that is subsequently oligomerized and cyclized into 1 by NonK.

The targeted gene inactivation and in vivo (±)-6 feeding experiment demonstrated that an ECH, NonS, is specifically involved in the (−)-pathway. The enantiospecific role of NonS was evidenced by accumulation of 2 and 3 in addition to 1 from (±)-6-fed SB2003 (nonS-inactivation mutant) that no longer produce macrotetrolide, which indicated that the biosynthesis of (+)-7 (the monomeric component of 2 and 3) does not require NonS and whereby, NonS participates specifically in biosynthesis of (−)-6 and (−)-7.

Figure 15:
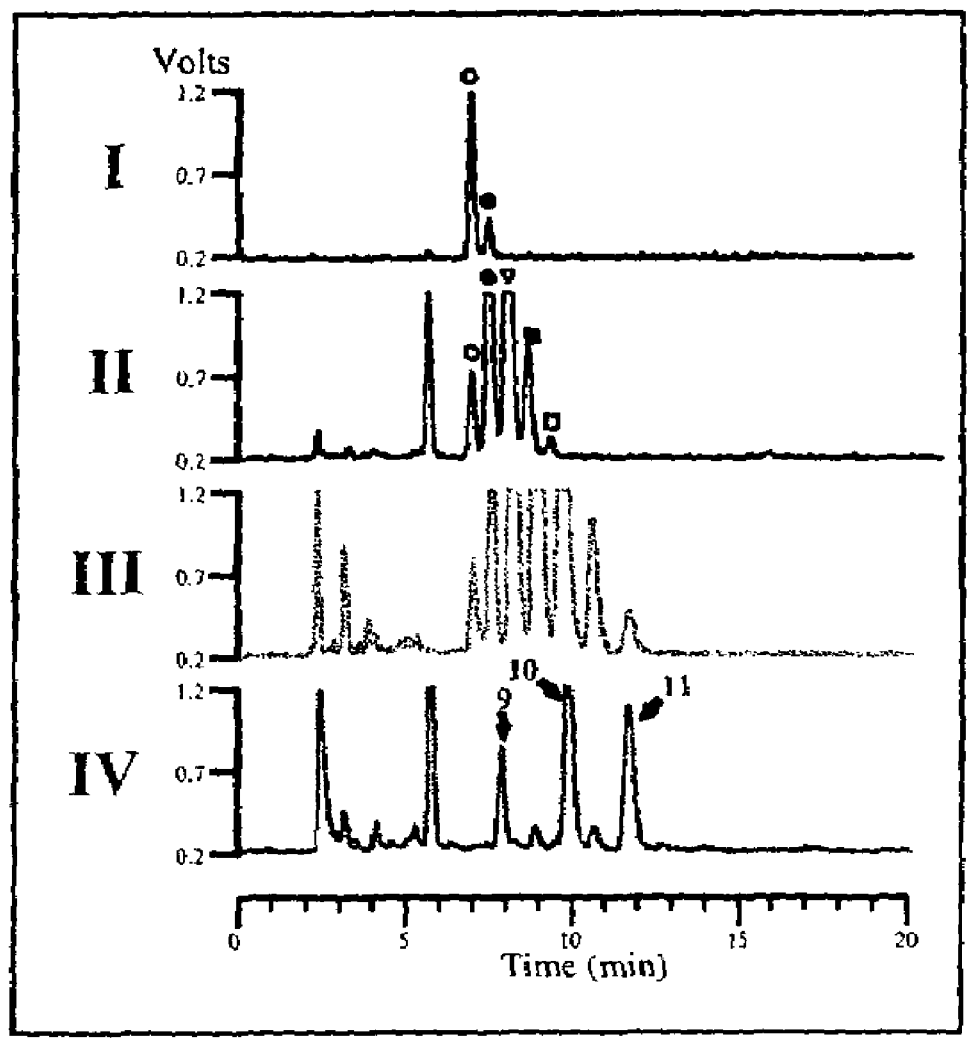
FIG. 15. Evaporative Light-Scattering Detector (ELSD)-High Performance Liquid Chromatography (HPLC) analysis of authentic nonactin (I), macrotetrolides isolated from *S. griseus* DSM40695 without (II) or with the supplementation of 8 (III), *S. griseus* SB2003 with the supplementation of 8 (IV).

Efficient in vivo incorporation of exogenous (±)-6 into 1 and the established synthetic method for 6-derivative had presented an opportunity to generate unnatural macrotetrolides though precursor-directed biosynthesis employing a synthetic 6-analogue. To practice this approach, the inventors prepared (±)-8-n-propyl nonactate (8) that was fed to SB2003 to seek new macrotetrolides derived from this synthetic building block. The feeding, extraction, and chemical procedure was described in Walczak, R. J.; Woo, A. J.; Strohl, W. R.; Priestley, N. D. *FEMS Microbiol. Lett.* 2000, 183, 171. (d) Smith, W.; Xiang, L.; Shen, B. *Antimicrob. Agents Chemother.* 2000, 44, 1809. When 8 was fed to *S. griseus* wild-type, production of new macrotetrolides was evident in HPLC analysis but their identifications and separations were severely compromised by the high abundance of natural macrotetrolides (FIG. 16AB). On the contrary, SB2003 provided a clean background due to natural macrotetrolide, by which accumulations of three 8-incorporated macrotetrolides were readily recognizable in HPLC spectrum (FIG. 16CD). The yield of new compounds from the 8-fed SB2003 was measured roughly by using authentic 1 (Sigma, St. Louis, Mo.) as the external standard and it was found that 1 mg of new macrotetrolides was generated from supplementation of 10 mg of 8 into a 50-ml-fermentation. The extract was further analyzed by thin layer chromatography (TLC), in which the compounds were readily separated. Each compound was then isolated and analyzed by HPLC (to correlate TLC to the cognate peak in HPLC) and mass spectroscophy (MS) analysis. As annotated in FIG. 15, the three compounds showed molecular masses of 875.63 (m/e for $C_{47}H_{80}O_{13}Na$, calcd 875.55; 9), 815.54 (m/e for $C_{44}H_{72}O_{12}Na$, calcd 815.49; 10), and 843.57 (m/e for $C_{46}H_{76}O_{12}Na$, calcd 843.52; 11), respectively, by which 10 and 11 were determined as macrotetrolides composed of two each of 6 and 8 and one 6 and three of 8, respectively (FIG. 11). The monomer compositions of 10 and 11 were confirmed by MS/MS and $MS^r$ analysis that generated daughter molecular ions resulted from the loss of monomeric 6 (m.w. 184) or monomeric 8 (m.w. 212); fragmentation of 10 resulted in m/e 631 and 603 as trimeric structures and m/e 419 as dimeric structure. Notably, the heterodimer of 6 and 8 (m/e 419) was solely detected as dimeric structure, which was consistent with the expected absence of dimeric 6 (the free acid form of 6") in SB2003 due to lack of (−)-6. Similarly, 11 was fragmented into m/e 659, 631, 447, and 419, verifying the inclusion of 6 and 8. The molecular ion mass of 9 corresponds to the linear tetramer composed of one 7 and three molecules of 8. The compound 9 may be a hydrolyzed product but more plausibly is an intermediate derailed from cyclization. The compound 11 was detected as the most slowly eluted compound in both HPLC and TLC, indicating that formation of other larger macrotetrolides such as 12 (virtual cyclized product of 9) and 13 (homogenous macrotetrolide composed of four molecules of 8) was not permitted by the given specificity of NonK (the dimerization of 8 by NonL/NonJ seemed readily occur as seen in 11).

In the in vivo experiment with SB2003, the inventors demonstrated that recruiting endogenous enantiomeric 6 with the exogenous synthetic 6-analogue (8) could generate unnatural macrotetrolides. However, the inventors encountered a limitation in macrotetrolide biosynthetic machinery; that is, 12 and 13 could not be generated. As aforementioned, the inventors established a cell-free system by expressing NonLJK in *S. lividans*. Harnessing this in vitro system and the acquired information, previously described, on distinctive roles of NonL, NonJ, and NonK, 8 was further challenged for formation of unnatural macrotetrolides in vitro.

In this particular experiment, the inventors expanded the category of synthetic 8 derivatives to determine the degree of flexibilities of each process in macrotetrolide biosynthesis. With minor modifications in the previously described method, (±)-8-n-propyl-nonactate (8), (±)-epi-8-n-propyl-nonactate (A), (±)-2-n-propyl-nonactate (B), and (±)-epi-2-n-propyl-nonactate (C) were prepared. These four compounds were tested for the CoA-activated by using purified NonL. Whereas 8 and A were efficiently converted into their CoA derivatives (8' and A', respectively) by NonL, no conversion was evident with B and C, implicating that introduction of bulky alkyl group near carboxylic group hindered its fitting into substrate pocket of NonL. The dimer formation was further tested with 8 and A by using CFE obtained from *S. lividans* harboring nonL and nonJ-expression construct [*S. lividans* (pBS2045)], in which 8 was converted the dimeric 8-CoA (8") but no dimeric A-CoA was found with A, indicating that the correct stereochemistry of hydroxyl nucleophilc C-8 is critical for C—O bond formation. The chromosomal DNA fragment encompassing nonJ and nonL from *S. griseus* DSM40695 was subcloned into pIJ4123 under the control of thiostrepton inducible promoter (tipAp) to generate pBS2045 that was introduced into *S. lividans* TK-24. For pIJ4123, see the reference; Takano, E.; White, J.; Thompson, C. J.; Bibb, M. J. *Gene* 1995, 160, 133.

Compared to the natural substrate such as 6', the dimerization process with 8' was significantly slow but a quantitative conversion was achieved by prolonged incubation (12 h). Identities of 8' and 8" were verified by MS analysis by detecting characteristic molecular ions (m/e for [M−H]⁻) of 978.222 ($C_{33}H_{56}N_7O_{19}P_3S$, calcd 978.249) and 1190.363 ($C_{45}H_{75}N_7O_{22}P_3S$, calcd 1190.390). After defining that 8 could be converted into 8" in vitro, generation of 13 was challenged by incubating 8 with NonLJK-containing CFE that was obtained from *S. lividans* (pBS2048). The pBS2048 was prepared by subcloining nonL, nonJ, and nonK into pWHM467 downstream to actIp and actIIIp. For pWHM467, see the reference; Wohlert, S. E.; Lomovskaya, N.; Kulowski, K.; Fonstein, L.; Occi, J. L.; Gewain, K. M.; MacNeil, D. J.; Hutchinson, C. R. *Chem. Biol.* 2001, 108, 1. The incubation failed to generated 13 even in prolonged incubation, however. The 8' and 8" were purified and incubated with *S. lividans* (pBS2048)-CFE but 13 could not yet be generated. Thereby, the inventors concluded that 13 can not be generated by NonK, proceeded by in vitro generation of 10 and 11. Although 13 was detected as the second major macrotetrolide in the 8-fed SB2118 (the nonO-mutant) and at the significant level in the SB2119 (the nonP-mutant) and SB2120 (the nonN-mutant), the negligible occurrence of 13 in SB2003 posed an reasonable doubt with the identity of 13 that has solely supported by the molecular ion (m/e 871.568) from MS analysis. It seemed possible that some alterations were imposed on stereochemical center(s) before 8 squeezed into 13. We already observed inter-conversions between (+)-6 and (−)-6 and even between 6 and 7 in SB2118 supplemented with (+)-6 or (−)-6. Furthermore, it was also observed that the same profiles of MTs were found from 8-fed and 8-epi-8-fed SB2118, which strongly urged us to consider alteration(s) of 8 to fit into 13.

Figure 16:
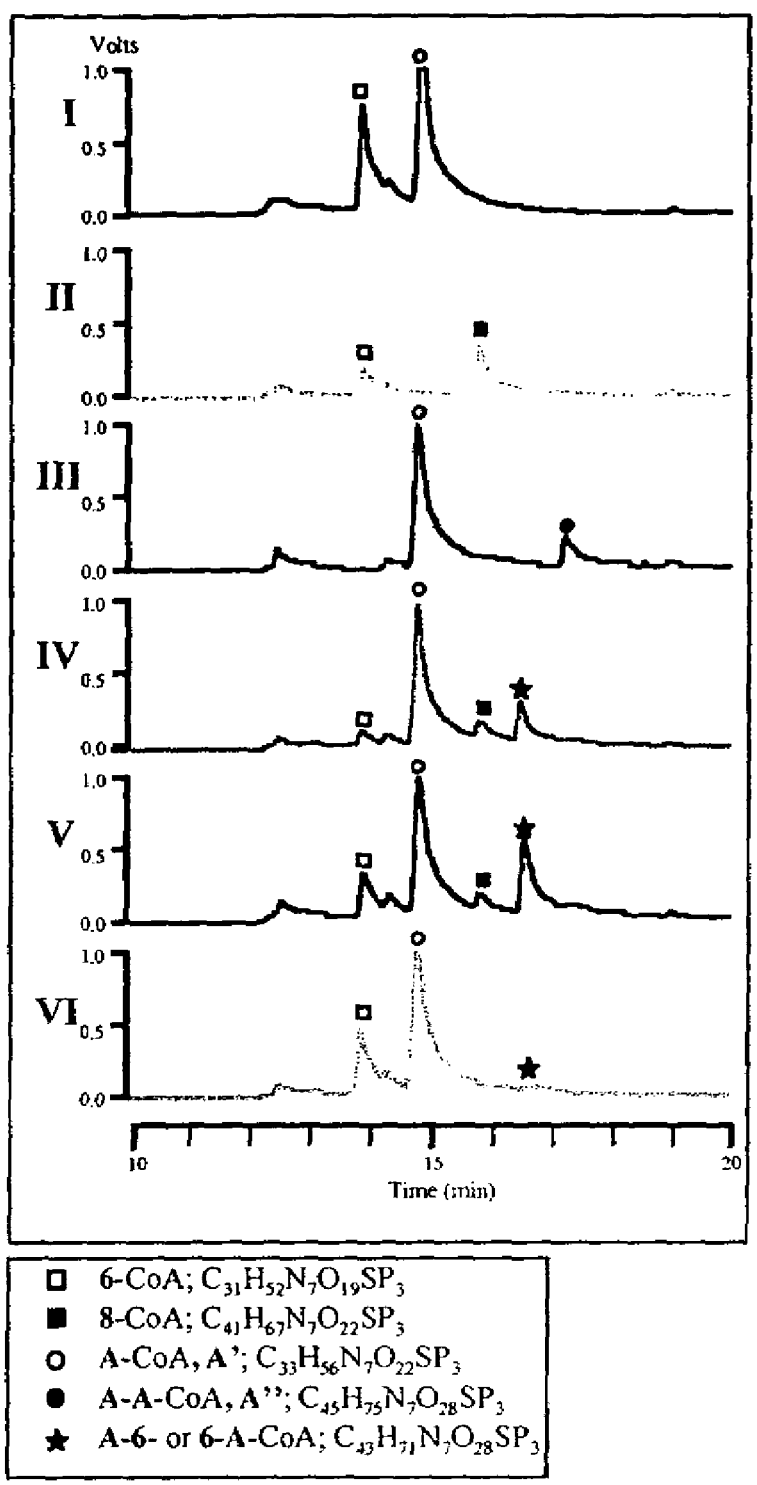
FIG. 16. In vitro assay of NonJ with (±)-6-CoA (II), (±)-8-CoA (III), (±)-6-CoA and (±)-8-CoA (IV), (+)-6-CoA and (±)-8-CoA (V), (−)-6-CoA and (±)-8-CoA (VI) and the control without NonJ (I). High Performance Liquid Chromatography (HPLC) analysis was performed on an Alltima C18 column (4.6×250 mm, 5μ, 100 Å, Alltech, Deerfield, Ill.). The column was first eluted in 5% $CH_3CN$ in 20 mM $NH_4Ac$, pH 5.8 (buffer A) for 7 min, followed by linear gradients from 100% buffer A to 50:50 of (buffer A:$CH_3CN$) for 8 min, from 50:50 of (buffer A:$CH_3CN$) to 10:90 of (buffer A:$CH_3CN$) and then maintained for additional 10 min at the flow rate of 1.0 ml/min with UV-detection at 260 nm.

When 6' and 8' were co-incubated with NonJ, a compound distinguishable from 6" and 8" was found as the major product with concomitant occurrence of 6" (FIG. 16-IV). This product was identified as the CoA-derivative of the dimer composed of 8 and 6 (14) by detecting the molecular ion (m/e for [M−H]⁻) of 1162.315 ($C_{43}H_{71}N_7O_{22}P_3S$, calcd 1162.358). With enantiomeric 6 in hand, (−)-6' and (+)-6' were prepared separately and incubated with (±)-8', which showed that (+)-6' was the preferred partner 8' for 14-CoA as (−)-8-(+)-6-CoA (FIG. 16-V). Even though significantly limited in the given condition, (−)-6 did generate 14'-CoA as evidenced by MS analysis (FIG. 16-VI). The 14'-CoA was supposed to be (−)-6-(+)-8-CoA. The preferred generation of 14-CoA to 6" suggested the co-incubation of 6' and 8' in *S. lividans* (pBS2048)-CFE. However, the co-incubation leaded exclusively to 1, which indicated that NonK highly preferred 6" to 14-CoA and it was apparently required to suppress generation of 6" to direct synthesis of 10 and 11, as in SB2003. Therefore, (+)-6' and (−)-6' were separately prepared and incubated with (±)-8' in *S. lividans* (pBS2048). Incubation of (+)-6' and (±)-8' resulted in generation of 10 and 11 as observed in MS analysis (Table 1A); it became evident that 1 and 15 were due to the incorporation of (−)-6' in the (+)-6'-preparation as an impurity (the chiral purity of enantiomeric 6 is 97%), which reflected that macrotetrolide to 10 and 11 were much slower than to 6"-derived macrotetrolides. Table 1 illustrates a matrix-assisted laser desorption ionization (MALDI)-mass spectroscopy (MS) analysis of ethyl acetate extract of *S. lividans* (pBS2048)-cell free extract (CFE) incubation with (+)-6 and (±)-8 (A) and (−)-6 and (±)-8 (B).

TABLE 1

| | m/e, [M + Na]⁺ | m/e, calcd | rel. int.* | structure** |
|---|---|---|---|---|
| A | 759.414 | $C_{40}H_{64}O_{12}Na$, 759.429 | 20 | 1, [4 × 6]$^C$ |
| | 787.442 | $C_{42}H_{68}O_{12}Na$, 787.464 | 100 | 15, [3 × 6 + 8]$^C$ |
| | 815.475 | $C_{44}H_{72}O_{12}Na$, 815.492 | 44 | 10, [2 × 6 + 2 × 8]$^C$ |
| | 833.489 | $C_{44}H_{74}O_{13}Na$, 833.502 | 14 | [2 × 6 + 2 × 8]$^L$ |
| | 843.508 | $C_{46}H_{76}O_{12}Na$, 843.523 | 10 | 11, [6 + 3 × 8]$^C$ |
| | 861.524 | $C_{46}H_{78}O_{13}Na$, 861.534 | 10 | [6 + 3 × 8]$^L$ |
| B | 759.391 | $C_{40}H_{64}O_{12}Na$, 759.429 | <5 | 1, [4 × 6]$^C$ |
| | 787.413 | $C_{42}H_{68}O_{12}Na$, 787.464 | 18 | 16, [3 × 6 + 8]$^C$ |
| | 815.441 | $C_{44}H_{72}O_{12}Na$, 815.492 | 100 | 17, [2 × 6 + 2 × 8]$^C$ |
| | 833.427 | $C_{44}H_{74}O_{13}Na$, 833.502 | <5 | [2 × 6 + 2 × 8]$^L$ |
| | | $C_{46}H_{76}O_{12}Na$, 843.523 | n.d.# | |
| | | $C_{46}H_{78}O_{13}Na$, 861.534 | n.d.# | |

*the relative intensities in the mass spectra
**the deduced monomeric compositions; $^C$cyclized form; $^L$linear form (see FIG. 11 for the structures)
not detected or detected but negligible The uncyclized (linear) form of 10 and 11 were detected as significant portions, reflecting they are derailed from NonK. Comparably, incubation of (−)-6' and (±)-8' lead to 17 (an enantiomer of 10) as a predominant macrotetrolide with negligible occurrence of the uncyclized form (Table 1B). The yield of 17 appeared as five times, at least, that of 10 as judged by macrotetrolide analysis but the yield itself might be affected and compromised by occurrence of 1 and/or 15; that is, high abundance of 1 and 15 might suppress the generation of 10. In the line of interpretation, it should also be reminded that 6"-formation from (+)-6'- and (−)-6'-preparation might be dramatically different due to obvious differences of their roles in 6"-formation. It was observed that a trace of 1 (inevitably, with the intermediacy of 6") occurred in the incubation with (+)-6'-preparation but not with (−)-6'-preparation, at least within the limit of detection method employed and when *S. lividans* (pBS2048)-CFE was used. The comparable level of 10 and 17, even with limitation in the generation of 14'-CoA (FIGS. 16-V and VI), and the relatively low level of uncyclized form of 17 assured that NonK-catalysis is the rate-limiting step.

Therefore, the inventors have demonstrated that biosynthesis of unnatural macrotetrolides can be achieved in vivo and in vitro by direct incorporation of a synthetic analogue. Generation of 10, 11, and 17 in vitro verified their identities originally characterized from in vivo conversion but was proved not the practical approach considering low conversion yield and a lot of labor in preparation of enantiomeric 6. Comparison of in vivo results with SB2003 and those in vitro showed that production of enantiomeric 6 by SB2003 was exclusive and in excellent yield.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

V. References

Ashworth, D. M.; Clark, C. A.; Robinson, J. A. *J. Chem. Soc. Perkin Trans.* 1 1989, 1461.

Ashworth, D. M.; Robinson, J. A. *J. Chem. Soc. Chem. Commun.* 1983, 1327.

Ashworth, D. M.; Robinson, J. A. *J. Chem. Soc. Perkin Trans.* 1 1988, 1719.

Ashworth, D. M.; Robinson, J. A.; Turner, D. L. *J. Chem. Soc. Chem. Commun.* 1982, 491.

Bao, W.; Sheldon, P. J.; Hutchinson, C. R. *Biochemistry* 1999, 38, 9752.

Bao, W.; Wendt-Pienkowski, E.; Hutchinson, C. R. *Biochemistry* 1998, 37, 8132.

Begley, T. P.; Kinsland, C.; Taylor, S.; Tandon, M.; Nicewonger, R.; Wu, M.; Chiu, H.-J.; Kelleher, N.; Campobasso, N; Zhang, Y. *Top. Curr. Chem.* 1998, 195, 93.

Bibb, M. J.; Findlay, P. R.; Johnson, M. W. *Gene* 1984, 30, 157.

Bibb, M. J.; White, J.; Ward, J. M.; Janssen, G. R. *Mol. Microbiol.* 1994, 14, 533.

Birch, A. W.; Robinson, J. A. In *Genetics and Biochemistry of Antibiotic Production*; Vining, L. C., Stuttard, C., Eds.; Butterworth-Heinemann: Boston, 1995; pp 443-476.

Borrel, M. N.; Pereira, E.; Fiallo, M.; Garnier-Suillerot, A. *Eur. J. Biochem.* 1994, 223, 125.

Callewaert, D. M.; Radcliff, G.; Tanouchi, T.; Shichi, H. *Immunopharmacology* 1988, 16, 25.

Carreras, C. W.; Kholsa, C. *Biochemistry* 1998, 37, 2084.

Choi, K. H.; Kremer, L.; Besra, G. S.; Rock, C. O. *J. Biol. Chem.* 2000, 275, 28201.

Clark, C. A.; Robinson, J. A. *J. Chem. Soc. Chem. Commun.* 1985, 1568.

Dreier, J.; Shah, A. N.; Khosla, C. *J. Biol. Chem.* 1999, 274, 25108.

Dutton, C. J.; Banks, B. J.; Cooper, C. B. *Nat. Prod. Rep.* 1995, 12, 165.

Ferrer, J. C; Jez, J. M.; Bowman, M. E.; Dixon, R. A.; Noel, J. P. *Nat. Struct. Biol.* 1999, 6, 775.

Fleck, W. F.; Ritzau, M.; Heinze, S.; Gräfe, U. *J. Basic Microbiol.* 1996, 36, 235.

Fleming, I.; Ghosh, S. K. In *Studies in Natural Products Chemistry*; Atta-ur-Rhaman, Ed.; Elsevier Science: New York, 1996; Vol. 18, pp 229-268.

Funa, N.; Ohnishi, Y.; Fujii, I.; Shibuya, M.; Ebizuka, Y.; Horinouchi, S. *Nature* 1999, 400, 897.

Hopwood, D. A. *Chem Rev.* 1997, 97, 2465.

Ishikawa, J.; Hotta, K. *FEMS Microbiol. Lett.* 1999, 174, 251.

Jez, J. M.; Bowman, M. E.; Dixon, R. A.; Noel, J. P. *Nat. Struct. Biol.* 2000, 7, 786.

Jez, J. M.; Bowman, M. E.; Noel, J. P. *Proc. Natl. Acad. Sci. USA* 2002, 99, 5319 and references therein.

Kilbourn, B. T.; Dunitz, J. D.; Pioda, A. R.; Simon, W. *J. Mol. Biol.* 1967, 30, 559.

Kwon, H. J.; Shen, B. unpublished.

Kwon, H. J.; Smith, W. C.; Scharon, A. J.; Hwang, S. H.; Kurth, M. J.; Shen, B. Science 2002, 297, 23.

Kwon, H. J.; Smith, W. C.; Xiang, L.; Shen, B. *J. Am. Chem. Soc.* 2001, 123, 3385;.

Meadows, E. S.; Khosla, C. *Biochemistry* 2001, 40, 14855.

Meiners, U.; Cramer, E.; Fröhlich, R.; Webbling, B.; Metz, P. *Eur. J. Org. Chem.* 1998, 2073.

Metz, P.; Meiner, U.; Cramer, E.; Fröhlich, R.; Wibbeling, G. *Chem. Commun.* 1996, 431.

Mishira, P. K.; Park, P. K.; Drueckhammer, D. G. *J. Bacteriol.* 2001, 183, 2774.

Mori, A.; Kaminuma, O.; Ogawa, K.; Nakata, A.; Egan, R. W.; Akiyama, K.; Okudaria, H. *J. Allergy Clin. Immunol.* 2000, 106, S58.

Mori, A.; Okudaria, H.; Kobayashi, N.; Akiyama, K. *Int. Arch. Allergy Immunol.* 2001, 124, 172.

Nelson, M. E.; Priestley, N. D *J. Am. Chem. Soc.* 2002, 124, 2894.

Nelson, M. E.; Priestley, N. D. *J. Am. Chem. Soc.* 2002, 124, 2894.

Pan, H.; Tsai, S.; Meadows, E. S.; Miercke, L. J.; Keatinge-Clay, A. T.; O'Connell, J.; Klosla, C.; Stroud, R. M. *Structure* 2002, 10, 1559.

Plater, R.; Robinson, J. A. *Gene* 1992, 112, 117.

Rawling, B. J. *Nat. Prod. Rep.* 2001, 18, 231.

Shen, B. *Top. Curr. Chem.* 2000, 209, 1.

Shen, B.; Kwon, H. J. *Chem. Rec.* in press.

Smith, W.; Xiang, L.; Shen, B. *Antimicrob. Agents Chemother.* 2000, 44, 1809.

Spavold, Z. M.; Robinson, J. A. *J. Chem. Soc. Chem. Commun.* 1988, 4.

Stahl, P.; Pape, H. *Arch. Mikrobiol.* 1972, 85, 239.

Staunton, J.; Wilkinson, B. *Top. Curr. Chem.* 1998, 195, 49.

Summers, R. G.; Ali, A.; Shen, B.; Wessel, W. A.; Hutchinson, C. R. *Biochemistry* 1995, 34, 9389.

Takano, E.; White, J.; Thompson, C. J.; Bibb, M. J. *Gene* 1995, 160, 133.

Tanouchi, Y.; Shichi, H. *Immunology* 1988, 63, 471.

Teunissen, M. B. M.; Pistoor, F. H. M.; Rongen, H. A. H.; Kapsenberg, M. L.; Bos, J. D. *Transplantation* 1992, 53, 875.

Tsai, S. C.; Miercke, L. J.; Krucinski, J.; Gokhale, R.; Chen, J. C.; Foster, P. G.; Cane, D. E.; Khosla, C.; Stroud, R. M. *Proc. Natl. Acad. Sci. USA* 2001, 18,14808.

Walczak, R. J.; Woo, A. J.; Strohl, W. R.; Priestley, N. D. *FEMS Microbiol. Lett.* 2000, 183, 171.

Wang, Y.; Metz, P. *Tetrahedron: Asymmetry* 2000, 11, 3995.

Watanabe, C. M. H.; Townsend, C. A. *Chem. Biol.* 2002, 9, 981.

Wohlert, S. E.; Lomovskaya, N.; Kulowski, K.; Fonstein, L.; Occi, J. L.; Gewain, K. M.; MacNeil, D. J.; Hutchinson, C. R. *Chem. Biol.* 2001, 108, 1.

Woo, A. J.; Strohl, W. R.; Priestley, N. D. *Antimicrob. Agents Chemother.* 1999, 43, 1662.

Zawada, R. J. X.; Khosla, C. *Chem. Biol.* 1999, 6, 607.

Zizka, Z. *Folia Microbiol.* (Prague) 1998, 43, 7.

What is claimed is:

1. A method of modifying a biological molecule by formation of a C—O bond comprising the step of contacting a biological molecule with a polypeptide selected from the group consisting of: (a) a polypeptide comprising the amino acid sequence set forth in SEQ ID NO: 3; (b) a polypeptide encoded by a nucleic acid comprising the nucleotide sequence set forth in SEQ ID NO: 2; and (c) a polypeptide encoded by a nucleic acid that specifically hybridizes to SEQ ID NO: 2 under wash conditions of at least as stringent as 0.2×SSC wash at 65° C. for 15 minutes and which catalyzes C—O bond formation; wherein said biological molecule is a substrate for said polypeptide, and whereby said polypeptide modifies the biological molecule by formation of a C—O bond.

2. The method according to claim 1, further comprising the step of contacting the biological molecule modified by the polypeptide recited in claim 1 with a second polypeptide selected from the group consisting of: (a) a polypeptide comprising the amino acid sequence set forth in SEQ ID NO: 5; (b) a polypeptide encoded by a nucleic acid comprising the nucleotide sequence set forth in SEQ ID NO: 4; and (c) a polypeptide encoded by a nucleic acid that specifically hybridizes to SEQ ID NO: 4 under wash conditions of at least as stringent as 0.2×SSC wash at 65° C. for 15 minutes and which catalyzes C—O bond formation; whereby said second polypeptide further modifies the biological molecule by formation of a C—O bond.

3. The method according to claim 1, wherein the C—O bond formed is between the biological molecule and a second biological molecule, said second biological molecule being also a substrate for the polypeptide.

4. The method according to claim 1, wherein said contacting occurs in a host cell.

5. The method according to claim 4, wherein said host cell is a bacterium.

6. The method according to claim 4, wherein the host cell is a eukaryotic cell selected from the group consisting of a mammalian cell, a yeast cell, a plant cell, a fungal cell, and an insect cell.

7. The method according to claim 4, wherein said biological molecule is an-exogenously supplied.

8. The method according to claim 1, wherein the contacting is ex vivo.

9. The method according to claim 1, wherein said biological molecule is an enantiomeric nonactic acid compound.

10. A method of catalyzing a C—O bond formation between biological molecules comprising the step of contacting biological molecules with at least one polypeptide encoded by a nucleic acid comprising the sequence set forth in SEQ ID NO: 1, or by a nucleic acid hybridizing to the nucleotide sequence of SEQ ID NO: 1 under wash conditions of at least as stringent as 0.2×SSC wash at 65° C. for 15 minutes, said biological molecules being substrates for said at least one polypeptide, whereby said at least one polypeptide catalyzes C—O bond formation between the biological molecules.

11. The method according to claim 10, wherein said contacting is in a host cell.

12. The method according to claim 11, wherein said host cell is a bacterium.

13. The method according to claim 11, wherein said host cell is a eukaryotic cell selected from the group consisting of a mammalian cell, a yeast cell, a plant cell, a fungal cell, and an insect cell.

14. The method according to claim 11, wherein at least one of said biological molecules is an exogenously supplied substrate.

15. The method according to claim 10, wherein the contacting is ex vivo.

16. The method according to claim 10, wherein said biological molecule is an enantiomeric nonactic acid compound.

17. A method of producing a macrotetralide or a macrotetralide analogue comprising the steps of (i) contacting enantiomeric nonactic acid compounds with at least one polypeptide selected from the group consisting of: (a) a polypeptide comprising the amino acid sequence set forth in SEQ ID NO: 3 or 5; (b) a polypeptide encoded by a nucleic acid comprising the nucleotide sequence set forth in SEQ ID NO: 2 or 4; and (c) a polypeptide encoded by a nucleic acid that specifically hybridizes to SEQ ID NO: 2 or 4 under wash conditions of at least as stringent as 0.2×SSC wash at 65° C. for 15 minutes and which catalyzes C—O bond formation; under conditions such that the polypeptide catalyzes C—O bond formation between the enantiomeric nonactic acid compounds, whereby a macrotetralide or macrotetralide analogue is thereby synthesized; and (ii) recovering said macrotetralide or macrotetralide analogue.

18. The method according to claim 17, wherein said method is carried out in a host cell and the enantiomeric nonactic acid compounds are exogenously supplied.

19. A method of catalyzing C—O bond formation between biological molecules comprising the step of contacting biological molecules with a polypeptide selected from the group consisting of: (a) a polypeptide comprising the amino acid sequence set forth in SEQ ID NO: 3; (b) a polypeptide encoded by a nucleic acid comprising the nucleotide sequence set forth in SEQ ID NO: 2; and (c) a polypeptide encoded by a nucleic acid that specifically hybridizes to SEQ ID NO: 2 under wash conditions of at least as stringent as 0.2×SSC wash at 65° C. for 15 minutes and which catalyzes C—O bond formation; wherein said biological molecules are substrates for said polypeptide, whereby said polypeptide catalyzes C—O bond formation between the biological molecules.

20. The method according to claim 19, wherein said method is performed in a host cell and at least one of the biological molecules is an exogenously supplied substrate.

21. A method of catalyzing C—O bond formation between biological molecules comprising the step of contacting biological molecules with a polypeptide selected from the group consisting of: (a) a polypeptide comprising the amino acid sequence set forth in SEQ ID NO: 5; (b) a polypeptide encoded by a nucleic acid comprising the nucleotide sequence set forth in SEQ ID NO: 4; and (c) a polypeptide encoded by a nucleic acid that specifically hybridizes to SEQ ID NO: 4 under wash conditions of at least as stringent as 0.2×SSC wash at 65° C. for 15 minutes and which catalyzes C—O bond formation; wherein said biological molecules are substrates for said polypeptide, whereby said polypeptide catalyzes C—O bond formation between the biological molecules.

22. The method according to claim 21, wherein said method is performed in a host cell and at least one of the biological molecules is an exogenously supplied substrate.

23. A method of modifying a biological molecule by formation of a C—O bond comprising contacting a biological molecule with a polypeptide selected from the group consisting of: (a) a polypeptide comprising the amino acid sequence set forth in SEQ ID NO: 3 or 5; (b) a polypeptide encoded by a nucleic acid comprising the nucleotide sequence consisting of SEQ ID NO: 2 or 4; and (c) a polypeptide encoded by a nucleic acid that specifically hybridizes to SEQ ID NO: 2 or 4 under wash conditions of at least as stringent as 0.2×SSC wash at 65° C. for 15 minutes and which catalyzes C—O bond formation; wherein said biological molecules is a substrate for said polypeptide, whereby said polypeptide modifies the biological molecule by formation of C—O bond.

* * * * *

UNITED STATES PATENT AND TRADEMARK OFFICE
CERTIFICATE OF CORRECTION

| | |
|---|---|
| PATENT NO. | : 7,416,870 B2 |
| APPLICATION NO. | : 10/646664 |
| DATED | : August 26, 2008 |
| INVENTOR(S) | : Ben Shen et al. |

Page 1 of 1

It is certified that error appears in the above-identified patent and that said Letters Patent is hereby corrected as shown below:

Title page, item (75) Inventors, line 2, please delete "Austin, WI" and insert --Austin, TX-- therefor.

In claim 7, column 59, line 57, delete "an-".

In claim 23, column 62, line 17, delete "of C—O" and insert --of a C—O-- therefor.

Signed and Sealed this

Eleventh Day of November, 2008

JON W. DUDAS
*Director of the United States Patent and Trademark Office*

SEQUENCE LISTING

```
<160> NUMBER OF SEQ ID NOS: 7

<210> SEQ ID NO 1
<211> LENGTH: 15559
<212> TYPE: DNA
<213> ORGANISM: Streptomyces griseus

<400> SEQUENCE: 1
ctcaggcgcg cggtcaacag caccatcctg cggcgcctgg tgcgccccga ggagatcgcc      60
gcccaggtcc tgttcctgct ctccgacctc tccggcggga tgaccggaca ggccgtcaac     120
gtggacgcgg gggctctgtg agcaaggagc acggcccggg gaagggcgaa ccgcccctgc     180
cggaacagct gctcgccccc gcggcgcgcc cctgggcccc cggcccccgg gacgcgctgg     240
tcaccgggat ggggttctgc ctgcccggtg cgggcgacga gccggtgcgc acggccgagc     300
aggtctgggc ggccgcctcc accggaccag tcatgtcga acgcgacggc ttccaccacg      360
ggaccgtacg cggtgcccgc gaggcgttcg gagagctgct gccggacata ccggcccgct     420
atctgcgcag ctacgccgac gtccacctct acgggctgat ctcgctggcc gaggcctgcc     480
gggacgccgg actcgattac gggaaaggcg agttgagagg ggcggacgtg ctgaccgccc     540
```

-continued

```
gggccggggt ggacagcaac tacgacagct accgcgcctg gcacgacgcc gatccggcga    600
cggtcactcc ctcggacgcc aagtccctct tcgtacggct cctggtggcg ggcacctcca    660
gcgacgtcgg ccccgtccag gccgcgctgc tcggttccac cggcgccaac tacacggtga    720
gctgcggctg cgcctcctcc tcggtgctgc tcggcatcgc ccgcatgatg atcgcctccg    780
gccagagcga cctggtcgtg gtcaccgggg tggaccgctt cgacaccgaa cgggtgctgc    840
acggacaccg gttgcgcgag gtcgtcgagc gcgagggcgt gacggtgcgg cacaacagcg    900
atccgccggc agcaccccgt cacgaccggc cgatgcgccc gtacgacgcg gcgggcgact    960
gcatgaacta cggcgacggg tcggtgaccc tgatcctgga gagccgcgaa cacgccgccg   1020
cgcggggcgc ccggacgcac ggggcggtcc tcggccaggc caccacgcgc ggggggcctga  1080
acagcgccgt cgccatcgac accggcgta cggggctggc cgaagcggcc cgccgcgccc   1140
tgggcgacca tacctcgctg gggcggatcc cctacgtcaa cgggggcggc gagggcgacg   1200
cgctgttcac ccggatcgag tccaacgccg tccgcgccct gtgggcgac cggtccgagc   1260
aggtgctggt gagttcgcag gaggcgtgct cgggcacag cggcgcgccg ctcggcaatc   1320
tgggcacggc gctgacgctg atgatgatgc gcgaggagag ggtctgcccc acggccaact   1380
gcgcgacccc gtcgcccgtc tgcacattcg accggtccc cggcaccagg acgcgtgcgc   1440
tgggcttcga ccgggccctg agcttcaact accaggtggg cggggtcaac agcgcactgc   1500
tgctgggagg tggcgatgtc tgctgagctg cctctgctgc ggctttccgg cgccgggttc   1560
gtcctgccgg ggccggacgg ccgcgcctgc accgacctgg acaccttctg gggtgtggtg   1620
cgcgacgggg cgagctgcct ctccccgtac gcccatcccg aactcccct ccgtatcgcc    1680
gggaccgtga acggctggga cccggagacc gaactcccgc tgtcggaacg gcagatacgc   1740
cgttcctcgc gcgccgggct gatggccacg ggtgcggtgc accgggcgct ggagcacgcc   1800
gggctgagcg cggacgacct cgatccgggg cgtaccgcgc tcgtcgcctg ctcgctccag   1860
ttcgcgttcc cggagaccga cgctactac gccctggccc gggacgaggg ggtcgccgcc    1920
ctcggcatgg agtactggct caacgggacc ccgcccagtg tggtgggcac cgtggcctcc   1980
ggcctccggc tgccctgcca gacgctgagc gtggcgggct cctgcaatgt ggcgctgcgg   2040
acgctccacc tcgtccagca gatgttccgg tgcggggaca tcgaccgcgc gatcgtcgtc   2100
ggcgtggaca ccacggtgga cccggtcttc gtggcaggca ccagccacac cggacgcagc   2160
ggctaccgcg cgtcctcgct ctccgacgac cccgccgacg tccggccgca cgacgagatc   2220
cagaccggca acgccaccgg ggagggcgcg ctcgccgtgg tgctgaaaaa cccggcggcg   2280
accggggacc gccgggggct gctgcaccgc gcgcatctgc gcacctcgcg ctccaacggc   2340
ccctccaccg tggccaccgg accgcccgcc aacgtggtgg cgacgtact ggccacgctg    2400
gcttcggccc ggcgcggcct gggcgatctg gcgttcgtca cgactacgc ggacggcaac    2460
cggttcgtcg aggaccacct gtgccaggcg ctcgccgggg tgaaggaggc ggcccgggtac   2520
ggcggggagc tgcggctcac caaccaggag gcggtcttcg ggcatgtcgc cggaaccggc   2580
ggcctggtca aactcctcgg cagcctcctc atgctgcgcc acggccatat cgccccagc    2640
gccaacaccc tggtcccgta cgcgggtctg ccgggcgacc cggtgctcgc gggcggcctg   2700
gcgaccggcg gagacagcgc gctggtgctc gcctccgggg cgggcggcga cgccacgagc   2760
atggtcatcg aatacgaagg cggcgacttg ccatgaccca cgttcacagc acggcgacgc   2820
ggcccgggac ggccgcggga ggggacccgt cgcgggcgcc ggtcagcacc cgcgtggtcg   2880
tcgacgccgc cgggggcgac ggtcctgccg ccggggccct ctccgacgcg ctcaccgcgc   2940
```

```
tcggcctcgc ccccgaggcc ccggacaccg aggccccgga caccggccgc gccgattccg    3000
gcgaccccgc cccggccgcc tactgcgctc tgctgctcgg cgaggaggcg tacggcgccg    3060
gacgctcggc gggcctggac cgctcacgcg tccgggccgc cgcgctggcg attgcgcgcg    3120
cgggccgggg acggctcgtc ctggtgaccg acgcgacggg cgagacccac gccggaaccg    3180
accccgaccg gtacgcgcgg ctcgccgccg accgggcctg gtggcagcac ctggtcaccg    3240
aggtggccgg gcgcggcgtc accggcaaca ccgtggtcac gggctactcc cccggcctgg    3300
gccaccggct gtccgccgag gccgaggccg ggctgctgcg ctgtctcgtg cagcgccggc    3360
ccaccacggc cgccgatgtc gcggccaccg tcgccttcct ggtctccgag gggtgttcgt    3420
acctggtcgg cgagactctg ccggtcgacg ggggcgcggg cctcggccag atcccgtccc    3480
tgcccgccgg cccgccgacg acggcccccg caccgcgccg cggtgctccg cgggagcagc    3540
cgccgccgga ccggtgagc ggtcaggacc tcctgggcca caaggtcctg gtggcgggcg    3600
cgagcagcgg catcggccgg gccgcggccc tgcacctggc cggacgcggg gccgacgtga    3660
tcctggccgc ccgccggacg caggcgctgg aggaggtggc cgccgagatc gaggcccggg    3720
gccggcaggc ctggaccctg cgctgcgacc tctccgacgc cgaggacgcc gcttctctgg    3780
gcgaacgggc ctggaaggcg gccgacggcg tcaccgccct gctgtacgcg gcggggcacc    3840
tgggcttcag cgcggtcggc ggcgaccccg cttccgccgc ccggaccttc gcggtgaacc    3900
tgcacagctt cgtcgccgtc accgagtacc tggcggcccg ctggcgggac gagaggatgc    3960
ccggagcggt ggtcggggtc tcctcggtca gctccacgct cagcccggtg gcgggcctgg    4020
agtactacgg ggcgagcaag gccgcgatgg cgcagtacat ccgctgtctc gcggtctcgg    4080
tgggccgcca cggcatccgc gccaactgcg tggctcccgg catcatcgag acgccgatgg    4140
gcgacgcggc ggggcccgac caccggcgcg gctggatcag ccggataccg gccgggcggg    4200
tcggcgaccg gcacgaggtg gcggcggtcc tcggctatct gctgagcggt tcggcctccc    4260
gggtgaccgg tgccgtgctg cgcgcggacg gcggcttcgg cctcggtgac gtggctccgc    4320
tgcggccggg ataccggag cgggccttcc ctgcaccggc gctcccggag cgggcggagg    4380
gggagaaccg atgaccgcca ccgcgcaagc aggccgccac ccggtcgccc tcgtcgccgg    4440
cgcctcctcc gggatcgggg ccgccgtcgc ccgccgactg gccgcgcgcg gcagcgccgt    4500
ggcgctggtc gggcggcggg agcccgagct gaaggaggtc gcggagtcga tccgcgcggc    4560
cggcggaacc gcgctgtcgc tcgccctgga cctggccggg ccgggtgccc ccgccgaggc    4620
ggtcgccgcc accgcggccg gactgggggcc ggtcggggctg ctggtgtgca gcgcgggcgc    4680
catccggctg gccgccgtcc acgagaccga ggagcggcac tgggaacggc agttgcgggt    4740
gaacctcacg gtgccgttcc tgctggcccg tgaggtgctg cccggcatgc gggagcgcgg    4800
cttcggctgg gtcgtgaaca tcggctccgg tgtgggctcg gaggtggtgc cgggcagcgg    4860
cggctacggc gtcagcaagc acaccgtgca ccggctcacc gagctgatcc acgaggagaa    4920
ccgcgacctc gggatccgcg cggtcaccgt cgccccgggc tgggtctcca cccggctcgc    4980
ggcccggccc gccgatctcg gggtgcccga ggaggaggtg ctggacgcgg aggacatcgc    5040
ggacaccgtc gcgtggctgc tggaccgtcc ggcccggatg agcgtcggcc cgctggtccg    5100
cgtcgagccc tcggcgagcc gggccgccgc cggtgacgcc atgacccgcc atctgacccg    5160
ttcccgcgcc gagggcgccg gaccggatgc tgaggagacc cgctgatggg caggaccacc    5220
ctcatcgagc acgacgtgcc ggtggagatg cgcgacggga cggtgctgcg ggccgatgtg    5280
```

```
tggcgcccng ccgaaggacc ggcctcgccc gccgtgctct tccgcacccc gtacggcaag    5340
tccccgctgg gtcttgccac cctgaccccg gcccagtgcg tggaccgggg gtacgcggcg    5400
gtcgtgcagg acacccgggg ccggttcggc tcggagggcg agtgggcgcc gctggactgg    5460
tcccaggagg ggcccgacgg gtacgacacc gtcgagtgga ccgccgaaca gccttggtgc    5520
gacgggaacg tggccatggc gggcacctcg taccaggcga tcgtccagtg gctggccgcc    5580
atggagaagc cgccgcacct gcgggccatc gcgcccacga tgtccacctc ggccccttc     5640 gacgccgagc agctcggcgg tttcctgcgg ctggaccacc tcacgagctg gctcggcctg    5700
accgcgctgg agtgggtgca gcgccgggcg gcggcgggcc atccggtgga cggggcggtc    5760
gtcgccgagg tcgtgcagct gctcaccgca cccgaagtgc cgctgcgccg ctggccgttg    5820
tcgaccatcc tcgacttcga gggtttccc ggccggctgc gggacatctt cgcggggcac    5880
gtggcgacgg tggccgacta ccacctcggg gaagtcgggg tgcccacctt ctcggtcggc    5940
ggctggtacg acgtgttctc ccacggcacg atcgagctgc accgcccgt gcgcgccctg     6000 gacccggtgg cgggacggca cgagctggtc gtcggaccct gggtgcactc gggtcaactg    6060
ccgcaggtgc agggcgaggt gaacacgggg ccctacggtt cggcgcaggg cgcacggctg    6120
gccgatctgc acctggactt cttcgaccgc catctacggc cggccggggg gacgacgggc    6180
cgggactccg gcggggacgt gcggtatttc ctcttcggcg atgacgcctg gcaccgggcc    6240
gcgagctggc cgccgcccga ggccgtcgac gcgccctggt acctggcggg tccggccgac    6300
ggcgaggagg gcggcaggct gctgcccgcc ccgccccggg aggccccggg ccacgacgcg    6360
ttcacctacg acccggagga cccggtgccc tcgcacggcg ggcgggtgct ccagctcggc    6420
aggctggcgg cgggccccgct caaccaggcg catctggagg acaggccgga cgtgctctgc    6480
tacacctccg agccgctcac cgagccgctg gacgccgtcg gccggcagcg gctgcggctc    6540
cgcttcggct cggacgcacc cgccaccgcc gtggtcgcca aactcaccga cgtacacccg    6600
gacgggcgtt cgctgctcgt ggccgaggcc agcctccggc tggaggccga ggggacggc    6660 ccgcgggacg agccgtacga cgccgatctg ctgctcgggg acaccgcgtg gcgcttcgcc    6720
cccgggcacc ggctgcgggt ccacgtcacc agcagcaact tcccccatct ggaccggcac    6780
cccaacatcc cgggcccggt cggcgaggcg gagcactgcc gcaccgcccg ccagtcggtc    6840
tggtacggcg gcccgtacga gagcgtgctg cggctgagca ccctgccgc gccgagcgcc     6900 ggggagaccg cgtgatcgac gatgtgctcg atccggcgtc cgccgccgtg cccacgcgg     6960 agcagtgcgt gctgggtccc ctgctcaggc gacgtgccgc cgcagcaccg gcggcgccgt    7020
acgcgttgat gccggacggt gacctctgga cgtacgcgcg caccctccgg gagaccgagg    7080
agacggccgc cgcgctccag gcgctgggag tcgtcccggg cgaactggtg ctgagctggc    7140
tgcccaacgg acccgacgcg ctgcgcgcct ggtacggggt caacctggcg ggcgcggtcc    7200
tggtgccgct caacatcgcc taccgggtg cgatcctgcg tcaggtgatc gccgacagcg      7260
gggccgaggt gctgatctgc cggccgtcgc tggcggcccg gctggaggat tcggacgacg    7320
cggtgggggc ggtgcgcacg gtggtcctgc tgccggggcc cgaggacgcg gcccaggacg    7380
tggaggcgct cgccgggcgg ctggccacgc gcttccgggt ggagaccgca ctgcgcgcgg    7440
accgggcgga gttcgcggag ccggtgcccg cccccggcc gtgggacccg cagaccgtca    7500
tctacacctc cgggacgacc ggtccgtcca agggcgtcgt ctcctcctac gcgcacctgt    7560
acagcagttg caccgccgcg ttccacggca tggccggacc ggaggaccgc tatctgctgc    7620
aactgccgct gttccacgcg ggcggcacga tcggcgcgta cgggatgctg gtgcacggcg    7680
```

```
gttcggtgac ggtcgtgccc gcgttcacca ccggggagtt ctggccgctg atccggcgga      7740
cggggacgac cctgtgcacg ctgctcggcg tgatggcgac ctatctgctc aagcagccgc      7800
cgctgccgca ggacaccgcg cacccgttgc gggcggccta cgtcatcccg ttcaccgagg      7860
gggcgacgga gttctccaag cggttcgggg tcccggtccg cgcgctgttc aacatgaccg      7920
aggtgtcgtg tccggtgctc tccgcgccgg accaccaccc gggcgtcccg atgcactgcg      7980
gggagccccg gccggggatc gccgcgcggg tcgtcgacga ccacgaccgg gaggtggcgg      8040
acggcgaggc gggcgaactg gtgctgcgcg cggaccgtcc gtggtcgttc ctgagcggct      8100
acctcggccg gcccgccgag acggccgccg tctggcgcaa cggctggttc cacaccgggg      8160
acaccttccg ccgggccccg gacgcgggc tggtcttcgt ggaccgcaag aaggacgcca      8220
tccgcaggcg cggcgagaac atctcctcct tcgaggtgga ggcgcaggcg gtggcccacc      8280
cgggggtgct ggaggcggcg gcggtggcgg tgcccggcga cgagggcgag gacgaggtgc      8340
tgctggtggt ggcggaccgc gaccccctcgg ccccggtcga cccggcggcg ctgctggagt      8400
tcctgcggga gcggctggcc cacttcatgc tgccgcgcta catccgggtg ctgcccgagc      8460
tcccgaagac tcccaccggc aagccgacca agcacacgct gcgcgccgag ggcgtggtgg      8520
cggggacgtg ggaccgcgag gccgcgggca tccggatacg cagggagaag atcgtatgaa      8580
ccaggaagca ttccgggcgg ccaggaacc cccggccgag tgggcggggg cggcgaccga      8640
gtcgttcgcg gacttcgccg accgggtgga cggcaaggag gtcgtaccgc tgcgggcctc      8700
gcttgcgggc ggggtcgcca ccctgacgct ggaccggccg caccgccgca acagcctcga      8760
cctgacgctc tcccgccatc tgctgctcgg cctgatgtgc gcgggcgacg accccggggt      8820
gcgtacggtc gtgatcaccg ggaacggcgg ggcgttctgc gcgggcgacg acgtcgggag      8880
cgtacggcgg tggcggctgg gcgaccgggc ggacaccccc ttcgaccgga tcacctcgga      8940
cgcccactac ctgcgggtct gcgaggcgat cctgcatctg ccgaagccgg tggtcgtggg      9000
gctgaccggg gcggcggcgg gcgccggggc ggagatcgcc tgcgccgccg acttccggct      9060
ggcggacacc cgtgcctcga tcggcagttg cctggccggg gtcggcatg tggggaacgt      9120
ggtcctgatg tcccggctga ccggtccggc gcggcgacg gagatctacc tcaccgggcg      9180
gatggtctcc ggggacgagg cggtgcgcct ggggctgttc gaccggctct gcgaaccgga      9240
ggatttcgac cgcgaactgg ccgatctggc gggccggttc gcggcactgc cgaccgcttc      9300
ggtgggggctg ttcaaggagt gcgggagcg gagctggggg cagccggccg agtacgggct      9360
gcggctccag gacacgtacc acctgaagac gcacgcgacg gtggccgacg cccgggaggg      9420
gatgccgcgt tcacggaga gcggccgcc ccgcttcacc ggcgcctgac cggtgccggg      9480
cggggtctcc gcccggcacc ggggtctccg tccggtgccg gcccccgtcc ggtgccgcga      9540
cccgtcgggg ccgcctccct ttgcggctgc gacggagaga gtattctgat tctgatgaac      9600
gaagcactcc ggcaccgccg cccggcggcc tcgccgcctc cgcctccgcc cctgtccgcg      9660
cccctgtccg cgttcaccgc cggccccgcc gaggaggccc cccgatgacc ggccccgacg      9720
gccgaaccgt caccggggcc cgcgtcgagg agacggcgca cagcatcgac gtctccggcg      9780
cccggctgca ctactggacc gccggagctg cggaccgccc ggggatcgcg ctgacccacg      9840
gcgccggggc cgaccaccgc atgttcgatc cgcagatccc ggcactggtc ggcgcgggct      9900
accgcaccct gcgctgggac gtgcgctacc acgggcgtc cgtctccggc acgggcagat      9960
tccgtacggt ctacgcggcg cgggacctgg cagcgctgct ggacgcggcc gggatgcccc     10020
```

```
ggcccgtggt gctgctgggc cagtcgatgg gcggcaacat cgcgcaggag tatctgcgcc    10080
gacggcccga cgaggtcgcc gcactcgtgg tgatcggctc cacctccaac accctgccca    10140
tcacccgggc cgagcggcgc ggcctggcgt tctcccgcgc cttcatgcgg ctgatgccct    10200
accgtcggct gacccggtcg atggccaggg cgtcggccga ggaccccggt gcgcggacgt    10260
atctgcgcga gaccttcctg gccaacggga ggcgctcctt cctcaccacc tgggacggca    10320
tgaccccgcg gatcgacccg tcccccgact accgggtcga gaagcccgaa cttctcctct    10380
gcggtgaaca cgacagcacg ggtaacatcc gctcggcgat ggaacggtgg agcgaacgcg    10440
atccccacag cgagttccat gtgatcccgg tgccggaca tgtcgccaat ctggaccgtc    10500
ccgacgaggt caaccggctg accgtcgcct tcctgaaggc ctgagacccc agcgagacca    10560
tgactgacca cgacatcacg cccgacgcgg gacccctccc gatgcccggc tccgacgggt    10620
tcagcgacgc ggaagccgcc ttcatcagcg agatgggttc gctgatggag cgctggggcc    10680
tcccgcaggc caccggccgc ctcttcggct acctcctgct gcgcaacaag ccggtggacc    10740
tcgacaccat gacccgcgaa ctcggccagg ccaagagcgg gctgagtgtg ccgcccgcc    10800 aactggaggc ctggtccctg gtgcggcgct cgaccagggc cggcagcagg cggatcgact    10860
acgaggcggt gggcgaccte cagcacctgc tgctggtgaa caacgcccat atgcgcaagt    10920
tcaccgagac gctgagctcg ggaatcccgg tggcgcgcgg cgaggcccgg gaccgactgg    10980
cctcgctcgc cggcctgttc aacgggtacg tggagcagac cgaggcgctg gtggccgcct    11040
gggaggcccg cgcgccgcc acctgagccc ggccgttccc ttctcccttc tgagcccggc    11100
cgttctcttc tccctccttc tccgcttcct cgtccttccc cttcctgctt ccgatggagt    11160
gaccgtgaac gtgtcgtccg tccccgcgcc gggcaacgga acaacggtgg ccaccgccgt    11220
ggcggaccct ggagtccgga tccgcccgcc ggtcatggac gcctgctcgc tggtgtacga    11280
cgacgcgggc tggcgggcgt acctgaaccg gctgggcgag aacgcccctg agtacctgga    11340
tgtcttctcc gcctcgttct gccggtactt cggcgcctcg cacaccgcgt accgcgacgc    11400
gctcgccgtc cgccggcagg acgcgatcga cgtgctcctg ccaccggacc ggccaccgtt    11460
cgatctggcc gggcatctcg cggaccggga acggcagggt gtgacgggcg agttcgccat    11520
gggctcggcg gaacggctgc cggacggccg tacggtcaac gagtggctgc tggagaccgt    11580
acgggacgtg cgcgaccgga tccacgtctg ggccgggatc tccctgcgcg accccgccgc    11640
cgcgctgcgg gagctggagc ggtcgctggc ggccggggcg accgggctgt gcgtcatccc    11700
cttcctggac ggcaccgacc cggccgaccc gaggttcgcc ccggtctggg acgccgcggc    11760
cgaggcgcgg ctgccggtct ggctgcacac cggccaccac ttcgcccgga gccacccag    11820 cggcctggc agctggcgta cggtcagac gctcgcgggc cgccaccgcg cgctgctgct    11880
cgtcgccggg cacgcgggct ggcccgatgt gcaggagatg ctgctcacgg ccgcccggca    11940
ccccggggtc ttcctggagt tctcctcgca ccggccccgg cacatgtcca agcccggctc    12000
gggctgggag cccctgctgc accacgcccg gggatggcc cgcgaccggg tcatgttcgg    12060
cacctcgacc tgggtcaatc cggggccgac ggaccgctg gccgatgagc tggccgcgct    12120
cccgctcccc gccgacgtgg tcgccgcctg gctctcgggc aacgcggagg cgctggtcgc    12180
ccgtgcggcc gggacccacc ggggctgagc cgcgccggga gccctccgga tgatgcgac    12240 ccgtcgccgg gggcagggga tccgccggac ggccgaaagc gcagccccg tcggaagcct    12300 ctttccggca cacgtgggca ggaggcggat cctggccggg ccgggcctac cgtcggcctg    12360
gtcagccacc ccgaccaacg gagatgtacg acatggcaaa gatccttttc gtggtgtccg    12420
```

```
gcgcggacca ctggaccctg gcggacggca cggcccaccc cacgggcttc tgggccgagg    12480
aggccgtggc gccgtaccgg gcgttcaccg acgccgggca cgaggtggtc gtcgccaccc    12540
cgggcggcgt cgtcccgacc gtggaccggg gcagcctggc gcccgacgtc aacggcgggc    12600
aggagggcgc cgacgcggtg gcggccggtc ttgaggcgtt cgaggagctg cggcggccgg    12660
tcgccctgga ggacgtggac ccggacgtgt acgacgccgt cttctacccc ggcggccacg    12720
gcccgatgga ggacctcgcg gtggaccccg tctccgggcg gctgctcgcc cgggtgctgg    12780
cttcgggcaa gccgctcggc gtggtctgcc acggcccggc ggcgctgctg gccgcgaccg    12840
gacccgacgg ccggtccgcg ttcgccgggt atcggctgac gggcttcacc aacgccgagg    12900
aggcccaggc gggcttcgcg gacaaggcga agtggctgct ccaggaccgg ctggtggcgc    12960
tgggcgcgga cttccaggaa ggtgagccct gggcgccgtt cgtcatcacc gaccggaacc    13020
tgatcacggg tcagaacccg gcctcctccg tcccgttggc cgccgaactg ctcaaccggc    13080
tcggctgacc ggccgatcgg cggttcgccg cccgccggc cgggctgttc agacccagtc     13140
ccgccgcgcg gcggctcgc agagctccag caccaccgcg cccgtctcgg gctcgtcccc      13200
ggagacgggc cggacgcgcg caccgaccgt caccaggtgc ggagccgccc ccacgatctg    13260
gcagcggaag acgaaccctt ccgagaaccg caccagggac tcgttgcgcg cagcctcggt    13320
atagcggtgg accacggcgg tccggacgac cacgccgtgg ccggtggtgc gttcgggctc    13380
cagttcgctc gacgcgcaca ccgggcacag cagccgccgg aacgaggcgg tgccgcacca    13440
gcggcagcga ttgtaggaga ggccgcactc ctcgtgcgcc ttctggacgg tgcccattgc    13500
tgtctgggac acggctcgac cccctgcgct cgactcggac gcgccgcacc tgcactgcgg    13560
gcgcgtccgc accatatggc actcagtgcc ggaccgtaaa ggcactgagt gcccattggt    13620
actcagttct cgccgacggc tgcctcgatc tgctgcacga cacgccacat cggggtgccc    13680
ttccgcgcga ccatcacgat cacctcccct ttcccgtcgc cgccaccgga gaccggaaag    13740
ggggtggccg gtgtggggac ggcaggccgc cccacacct ctcggaccag ggcgagcgca      13800
tgatccacag ccgcctcggg gtcgcccgcc ccgcccgaac gcagccacag ccgaagcccg    13860
ttgttgtgcg cggcgaccac cgaagcggcg atcacctcgg cccgcagctc cccgtcgcga    13920
ccctcgccga agcgaccccg cagatgtccg gcgagagtct gttcgtaacg gcgcaccacc    13980
gacagttcgt acgtccgcag ccccggcacc tcccgagtga ggcggtagcg ctgcacggag    14040
aactcggggt tggccgcgta catccgcagc acgatgcgcg cggcgtcgca caccgcgccg    14100
accgggtcgc tgtcgtcgac ggcggccagg aactcggtcg tctcggcgag gcagcgctcg    14160
tggtccggga agaccgcgtc ctccttggac gggaagtagc ggaagaacga acgcggcc       14220 accccggcca gcgccacgat gtcgtccacg gtcgtccgct cgaagcccg ctccaggaag      14280 agccggaagg ccgcctgtgc gagcacctcc cgcatgggtg ccttcttctc ggatcctcgc    14340
gcctcgctca tgcggcgaaa cgtagcaccg cgaggaggat tttggcactg cgtacccttta   14400 cagagggtac tgagtgccat aatctctcca tcagtacgaa tgacacccag gtgggaccac    14460
acccaggtag gcaggagagc cggcgtgagc ttgaggatcg ttgtctgtgt gaagtacgtg    14520
cccgacgcga ccggtgaccg gcgtttcgcc gatgacctga cgctggaccg tgaggatgtc    14580
gacggtctgt tgtcggagct ggacgagtac gcggtcgagc aggcgttgca gatcgctgac    14640
ggggcggacg atgcggagat caccgtggtg acgtgggtc cggaggatgc caaggacgcg      14700
ttgcgcaagg cgttgtcgat gggtgcggac aaggcggttc acgtcgagga cgacgatctg    14760
```

-continued

```
cacggcagtg atgtgatggg gacgtcgctg gtgctggcga aggctgtgga gaaggccggg    14820
tatgacctgg tgatctgtgg gatggcgtcg acggacggtg tgatgggtgt gctgccggcg    14880
ttgctggcgg agcgtctggg tgtgccgcag gtgacgttgc tgtccgaggt cgcggtggac    14940
ggtggtgtgg tgacggggcg gcgtgacggt gacacggcgt ccgagcagct tgaggcgtcg    15000
cttcccgcgg tggtgtcggt gaccgaccag tcgggtgagg cccgttaccc gtcgttcaag    15060
gggatcatgg cggcgaagaa gaagccggtg gagtcgctgg acctgacga tctgggtctg    15120 gacgcggacg aggtcggtct ggcgggtgcg tggacggtgg tggattccgc caccgagcgt    15180
ccggcgcgga cggcgggcac gatcgtgaag gacgaggggtg agggcggcag gcagctcgcc    15240
gggttcctcg cgggccagaa gttcatctag tccgcatgtc tttccccgct gttcctctct    15300
ctcgtccttt cttgtctgga gtgcgttgtc atggctgaag ttcttgttct ggtcgatcac    15360
gtggacggtg cggtccgcaa gcccaccctg gagctgctga cgctggcgcg tcgtgtcggt    15420
gacccggtcg ccgtggtgct gggtgccggt gccggggacg ctgccccggt gctgggtgag    15480
cacggtgcgg tgaaggtcct gacctcggac gccccggagt tcgcggatta tctggtggtg    15540
ccgaaggtcg acgcgctgc                                                 15559
```

<210> SEQ ID NO 2
<211> LENGTH: 1281
<212> TYPE: DNA
<213> ORGANISM: Streptomyces griseus

<400> SEQUENCE: 2

```
atgtctgctg agctgcctct gctgcggctt tccggcgccg ggttcgtcct gccggggccg      60
gacggccgcg cctgcaccga cctggacacc ttctggggtg tggtgcgcga cggggcgagc     120
tgcctctccc cgtacgccca tcccgaactc cccctccgta tcgccgggac cgtgaacggc     180 tgggaccccgg agaccgaact cccgctgtcg gaacggcaga tacgccgttc ctcgcgcgcc     240
gggctgatgg ccacgggtgc ggtgcaccgg cgctggagc acgccgggct gagcgcggac     300
gacctcgatc cggggcgtac cgcgctcgtc gcctgctcgc tccagttcgc gttcccggag     360
accgagcgct actacgccct ggcccgggac gaggggtcg ccgccctcgg catggagtac     420
tggctcaacg ggaccccgcc cagtgtggtg gcaccgtgg cctccggcct ccggctgccc     480
tgccagacgc tgagcgtggc gggctcctgc aatgtggcgc tgcggacgct ccacctcgtc     540
cagcagatgt tccggtgcgg ggacatcgac cgcgcgatcg tcgtcggcgt ggacaccacg     600
gtggaccccg tcttcgtggc aggcaccagc cacaccggac gcagcggcta ccgcgcgtcc     660
tcgctctccg acgacccgc cgacgtccgg ccgcacgacg agatccagac cggcaacgcc     720
accggggagg gcgcgctcgc cgtggtgctg gaaaacccgg cggcgaccgg ggaccgcccg     780
gggctgctgc accgcgcgca tctgcgcacc tcgcgctcca acggcccctc caccgtggcc     840
accgaccgcc cgccaacgt ggtgggcgac gtactgccca cgctggcttc ggcccggcgc     900
ggcctgggcg atctggcgtt cgtcaacgac tacgcggacg gcaaccggtt cgtcgaggac     960
cacctgtgcc aggcgctcgc cggggtgaag gaggcggccc ggtacggcgg ggagctgcgg    1020
ctcaccaacc aggaggcggt cttcgggcat gtcgccggaa ccggcggcct ggtcaaactc    1080
ctcggcagcc tcctcatgct gcgccacggc catatcgccc ccagcgccaa caccctggtc    1140
ccgtacgcgg gtctgccggg cgaccccgtg ctcgcggcg gcctggcgac cggcggagac    1200
agcgcgctgt gctcgcctc cggggcgggc ggcgacgcca cgagcatggt catcgaatac    1260
gaaggcggcg acttgccatg a                                             1281
```

<210> SEQ ID NO 3
<211> LENGTH: 426
<212> TYPE: PRT
<213> ORGANISM: Streptomyces griseus

<400> SEQUENCE: 3

```
Met Ser Ala Glu Leu Pro Leu Arg Leu Ser Gly Ala Gly Phe Val
1               5                   10                  15

Leu Pro Gly Pro Asp Gly Arg Ala Cys Thr Asp Leu Asp Thr Phe Trp
                20                  25                  30

Gly Val Val Arg Asp Gly Ala Ser Cys Leu Ser Pro Tyr Ala His Pro
            35                  40                  45

Glu Leu Pro Leu Arg Ile Ala Gly Thr Val Asn Gly Trp Asp Pro Glu
    50                  55                  60

Thr Glu Leu Pro Leu Ser Glu Arg Gln Ile Arg Arg Ser Ser Arg Ala
65                  70                  75                  80

Gly Leu Met Ala Thr Gly Ala Val His Arg Ala Leu Glu His Ala Gly
                85                  90                  95

Leu Ser Ala Asp Asp Leu Asp Pro Gly Arg Thr Ala Leu Val Ala Cys
                100                 105                 110

Ser Leu Gln Phe Ala Phe Pro Glu Thr Glu Arg Tyr Tyr Ala Leu Ala
            115                 120                 125

Arg Asp Glu Gly Val Ala Ala Leu Gly Met Glu Tyr Trp Leu Asn Gly
    130                 135                 140

Thr Pro Pro Ser Val Val Gly Thr Val Ala Ser Gly Leu Arg Leu Pro
145                 150                 155                 160

Cys Gln Thr Leu Ser Val Ala Gly Ser Cys Asn Val Ala Leu Arg Thr
                165                 170                 175

Leu His Leu Val Gln Gln Met Phe Arg Cys Gly Asp Ile Asp Arg Ala
            180                 185                 190

Ile Val Val Gly Val Asp Thr Thr Val Asp Pro Val Phe Val Ala Gly
    195                 200                 205

Thr Ser His Thr Gly Arg Ser Gly Tyr Arg Ala Ser Ser Leu Ser Asp
210                 215                 220

Asp Pro Ala Asp Val Arg Pro His Asp Glu Ile Gln Thr Gly Asn Ala
225                 230                 235                 240

Thr Gly Glu Gly Ala Leu Ala Val Val Leu Glu Asn Pro Ala Ala Thr
                245                 250                 255

Gly Asp Arg Pro Gly Leu Leu His Arg Ala His Leu Arg Thr Ser Arg
            260                 265                 270

Ser Asn Gly Pro Ser Thr Val Thr Gly Pro Pro Ala Asn Val Val
    275                 280                 285

Gly Asp Val Leu Ala Thr Leu Ala Ser Ala Arg Arg Gly Leu Gly Asp
    290                 295                 300

Leu Ala Phe Val Asn Asp Tyr Ala Asp Gly Asn Arg Phe Val Glu Asp
305                 310                 315                 320

His Leu Cys Gln Ala Leu Ala Gly Val Lys Glu Ala Ala Gly Tyr Gly
                325                 330                 335

Gly Glu Leu Arg Leu Thr Asn Gln Glu Ala Val Phe Gly His Val Ala
            340                 345                 350

Gly Thr Gly Gly Leu Val Lys Leu Leu Gly Ser Leu Leu Met Leu Arg
    355                 360                 365

His Gly His Ile Ala Pro Ser Ala Asn Thr Leu Val Pro Tyr Ala Gly
```

```
                      370             375             380
Leu Pro Gly Asp Pro Val Leu Ala Gly Gly Leu Ala Thr Gly Gly Asp
385                 390                 395                 400

Ser Ala Leu Val Leu Ala Ser Gly Ala Gly Gly Asp Ala Thr Ser Met
                405                 410                 415

Val Ile Glu Tyr Glu Gly Gly Asp Leu Pro
            420                 425

<210> SEQ ID NO 4
<211> LENGTH: 1278
<212> TYPE: DNA
<213> ORGANISM: Streptomyces griseus

<400> SEQUENCE: 4 atgggggttct gcctgcccgg tgcgggcgac gagccggtgc gcacggccga gcaggtctgg      60
gcggccgcct ccaccgggac cagtcatgtc gaacgcgacg gcttccacca cgggaccgta     120
cgcggtgccc gcgaggcgtt cggagagctg ctgccggaca taccggcccg ctatctgcgc     180
agctacgccg acgtccacct ctacgggctg atctcgctgg ccgaggcctg ccggacgcc     240 ggactcgatt acgggaaagg cgagttgaga ggggcggacg tgctgaccgc ccgggccggg     300
gtggacagca actacgacag ctaccgcgcc tggcacgacg ccgatccggc gacggtcact     360
ccctcggacg ccaagtccct cttcgtacgg ctcctggtgg cgggcacctc cagcgacgtc     420
ggccccgtcc aggccgcgct gctcggttcc accggcgcca actacacggt gagctgcggc     480
tgcgcctcct cctcggtgct gctcggcatc gcccgcatga tgatcgcctc cggccagagc     540
gacctggtcg tggtcaccgg ggtggaccgc ttcgacaccg aacgggtgct gcacggacac     600
cggttgcgcg aggtcgtcga gcgcgagggc gtgacggtgc ggcacaacag cgatccgccg     660
gcagcacccc gtcacgaccg gccgatgcgc ccgtacgacg cggcgggcga ctgcatgaac     720 tacgcgacg ggtcggtgac cctgatcctg gagagccgcg aacacgccgc cgcgcggggc     780
gcccggacgc acggggcggt cctcggccag gccaccacgc gcgggggcct gaacagcgcc     840
gtcgccatcg acaccggcgg tacggggctg ccgaagcgg cccgccgcgc cctgggcgac     900
catacctcgc tggggcggat cccctacgtc aacgggggcg gcgagggcga cgcgctgttc     960
acccggatcg agtccaacgc cgtcgcgccc ctgtggggcg accggtccga gcaggtgctg    1020
gtgagttcgc aggaggcgtg cttcgggcac agcggcgcgc cgctcggcaa tctgggcacg    1080
gcgctgacgc tgatgatgat gcgcgaggga gaggtctgcc ccacgccaa ctgcgcgacc    1140 ccgtcgcccg tctgcacatt cgacccggtc cccggcacca ggacgcgtgc gctgggcttc    1200
gaccgggccc tgagcttcaa ctaccaggtg gcggggtca acagcgcact gctgctggga    1260
ggtggcgatg tctgctga                                                  1278

<210> SEQ ID NO 5
<211> LENGTH: 425
<212> TYPE: PRT
<213> ORGANISM: Streptomyces griseus

<400> SEQUENCE: 5

Met Gly Phe Cys Leu Pro Gly Ala Gly Asp Glu Pro Val Arg Thr Ala
1               5                   10                  15

Glu Gln Val Trp Ala Ala Ala Ser Thr Gly Thr Ser His Val Glu Arg
            20                  25                  30

Asp Gly Phe His His Gly Thr Val Arg Gly Ala Arg Glu Ala Phe Gly
        35                  40                  45
```

Glu Leu Leu Pro Asp Ile Pro Ala Arg Tyr Leu Arg Ser Tyr Ala Asp
    50                  55                  60

Val His Leu Tyr Gly Leu Ile Ser Leu Ala Glu Ala Cys Arg Asp Ala
65                  70                  75                  80

Gly Leu Asp Tyr Gly Lys Gly Glu Leu Arg Gly Ala Asp Val Leu Thr
                85                  90                  95

Ala Arg Ala Gly Val Asp Ser Asn Tyr Asp Ser Tyr Arg Ala Trp His
            100                 105                 110

Asp Ala Asp Pro Ala Thr Val Thr Pro Ser Asp Ala Lys Ser Leu Phe
        115                 120                 125

Val Arg Leu Leu Val Ala Gly Thr Ser Ser Asp Val Gly Pro Val Gln
    130                 135                 140

Ala Ala Leu Leu Gly Ser Thr Gly Ala Asn Tyr Thr Val Ser Cys Gly
145                 150                 155                 160

Cys Ala Ser Ser Ser Val Leu Leu Gly Ile Ala Arg Met Met Ile Ala
                165                 170                 175

Ser Gly Gln Ser Asp Leu Val Val Val Thr Gly Val Asp Arg Phe Asp
            180                 185                 190

Thr Glu Arg Val Leu His Gly His Arg Leu Arg Glu Val Val Glu Arg
        195                 200                 205

Glu Gly Val Thr Val Arg His Asn Ser Asp Pro Ala Ala Pro Arg
210                 215                 220

His Asp Arg Pro Met Arg Pro Tyr Asp Ala Ala Gly Asp Cys Met Asn
225                 230                 235                 240

Tyr Gly Asp Gly Ser Val Thr Leu Ile Leu Glu Ser Arg Glu His Ala
                245                 250                 255

Ala Ala Arg Gly Ala Arg Thr His Gly Ala Val Leu Gly Gln Ala Thr
            260                 265                 270

Thr Arg Gly Gly Leu Asn Ser Ala Val Ala Ile Asp Thr Gly Gly Thr
        275                 280                 285

Gly Leu Ala Glu Ala Ala Arg Arg Ala Leu Gly Asp His Thr Ser Leu
    290                 295                 300

Gly Arg Ile Pro Tyr Val Asn Gly Gly Glu Gly Asp Ala Leu Phe
305                 310                 315                 320

Thr Arg Ile Glu Ser Asn Ala Val Arg Ala Leu Trp Gly Asp Arg Ser
                325                 330                 335

Glu Gln Val Leu Val Ser Ser Gln Glu Ala Cys Phe Gly His Ser Gly
            340                 345                 350

Ala Pro Leu Gly Asn Leu Gly Thr Ala Leu Thr Leu Met Met Met Arg
        355                 360                 365

Glu Gly Glu Val Cys Pro Thr Ala Asn Cys Ala Thr Pro Ser Pro Val
    370                 375                 380

Cys Thr Phe Asp Pro Val Pro Gly Thr Arg Thr Arg Ala Leu Gly Phe
385                 390                 395                 400

Asp Arg Ala Leu Ser Phe Asn Tyr Gln Val Gly Gly Val Asn Ser Ala
                405                 410                 415

Leu Leu Leu Gly Gly Gly Asp Val Cys
            420                 425

<210> SEQ ID NO 6
<211> LENGTH: 1658
<212> TYPE: DNA
<213> ORGANISM: Streptomyces griseus

<400> SEQUENCE: 6

```
atgtgctcga tccggcgtcc gccgccgtgc ccacggcgga gcagtgcgtg ctgggtcccc      60
tgctcaggcg acgtgccgcc gcagcaccgg cggcgccgta cgcgttgatg ccggacggtg     120
acctctggac gtacgcgcgc accctccggg agaccgagga cggccgccgc gcgctccagg     180
cgctgggagt cgtcccgggc gaactggtgc tgagctggct gcccaacgga cccgacgcgc     240
tgcgcgcctg gtacgggtc aacctggcgg cgcggtcct ggtgccgctc aacatcgcct       300
accggggtgc gatcctgcgt caggtgatcg ccgacagcgg ggccgaggtg ctgatctgcc     360
ggccgtcgct ggcggcccgg ctggaggatt cggacgacgc ggtgggggcg gtgcgcacgg     420
tggtcctgct gccggggccc gaggacgcgg cccaggacgt ggaggcgctc gccgggcggc     480
tggccacgcg cttccgggtg gagaccgcac tgcgcgcgga ccgggcggag ttcgcggagc     540
cggtgcccgc ccccggccg tgggacccgc agaccgtcat ctacacctcc gggacgaccg      600
gtccgtccaa gggcgtcgtc tcctcctacg cgcacctgta cagcagttgc accgccgcgt     660
tccacggcat ggccggaccg gaggaccgct atctgctgca actgccgctg ttccacgcgg     720
gcggcacgat cggcgcgtac gggatgctgg tgcacgccgg ttcggtgacg gtcgtgcccg     780
cgttcaccac cggggagttc tggccgctga tccggcggac ggggacgacc ctgtgcacgc     840
tgctcggcgt gatggcgacc tatctgctca agcagccgcc gctgccgcag gacaccgcgc     900
acccgttgcg ggcggcctac gtcatcccgt tcaccgaggg ggcgacggag ttctccaagc     960
ggttcggggt cccggtccgc gcgctgttca acatgaccga ggtgtcgtgt ccggtgctct    1020
ccgcgccgga ccaccacccg ggcgtcccga tgcactgcgg ggagccccgg ccggggatcg    1080
ccgcgcgggt cgtcgacgac cacgaccggg aggtggcgga cggcgaggcg ggcgaactgg    1140
tgctgcgcgc ggaccgtccg tggtcgttcc tgagcggcta cctcggccgg cccgccgaga    1200
cggccgcgt ctggcgcaac ggctggttcc acaccgggga caccttccgc cgggccccgg     1260
acggcgggct ggtcttcgtg gaccgcaaga aggacgccat ccgcaggcgc ggcgagaaca    1320
tctcctcctt cgaggtggag cgcaggcgg tggcccaccc gggggtgctg gaggcggcgg     1380
cggtggcggt gccggcgac gagggcgagg acgaggtgct gctggtggtg gcggaccgcg     1440
accctcggc cccggtcgac ccggcggcgc tgctggagtt cctgcgggag cggctggccc    1500
acttcatgct gccgcgctac atccgggtgc tgcccgagct cccgaagact cccaccggca    1560
agccgaccaa gcacacgctg cgcgccgagg cgtggtggc ggggacgtgg gaccgcgagg     1620
ccgcgggcat ccggatacgc agggagaaga tcgtatga                            1658
```

<210> SEQ ID NO 7
<211> LENGTH: 555
<212> TYPE: PRT
<213> ORGANISM: Streptomyces griseus

<400> SEQUENCE: 7

```
Met Ile Asp Asp Val Leu Asp Pro Ala Ser Ala Ala Val Pro Thr Ala
1               5                   10                  15

Glu Gln Cys Val Leu Gly Pro Leu Leu Arg Arg Arg Ala Ala Ala Ala
            20                  25                  30

Pro Ala Ala Pro Tyr Ala Leu Met Pro Asp Gly Asp Leu Trp Thr Tyr
        35                  40                  45

Ala Arg Thr Leu Arg Glu Thr Glu Glu Thr Ala Ala Ala Leu Gln Ala
    50                  55                  60

Leu Gly Val Val Pro Gly Glu Leu Val Leu Ser Trp Leu Pro Asn Gly
```

```
                65                  70                  75                  80
Pro Asp Ala Leu Arg Ala Trp Tyr Gly Val Asn Leu Ala Gly Ala Val
                    85                  90                  95

Leu Val Pro Leu Asn Ile Ala Tyr Arg Gly Ala Ile Leu Arg Gln Val
                100                 105                 110

Ile Ala Asp Ser Gly Ala Glu Val Leu Ile Cys Arg Pro Ser Leu Ala
                115                 120                 125

Ala Arg Leu Glu Asp Ser Asp Ala Val Gly Ala Val Arg Thr Val
            130                 135                 140

Val Leu Leu Pro Gly Pro Glu Asp Ala Ala Gln Asp Val Glu Ala Leu
145                 150                 155                 160

Ala Gly Arg Leu Ala Thr Arg Phe Arg Val Glu Thr Ala Leu Arg Ala
                165                 170                 175

Asp Arg Ala Glu Phe Ala Glu Pro Val Pro Ala Pro Arg Pro Trp Asp
                180                 185                 190

Pro Gln Thr Val Ile Tyr Thr Ser Gly Thr Thr Gly Pro Ser Lys Gly
            195                 200                 205

Val Val Ser Ser Tyr Ala His Leu Tyr Ser Ser Cys Thr Ala Ala Phe
210                 215                 220

His Gly Met Ala Gly Pro Glu Asp Arg Tyr Leu Leu Gln Leu Pro Leu
225                 230                 235                 240

Phe His Ala Gly Gly Thr Ile Gly Ala Tyr Gly Met Leu Val His Gly
                245                 250                 255

Gly Ser Val Thr Val Val Pro Ala Phe Thr Thr Gly Glu Phe Trp Pro
                260                 265                 270

Leu Ile Arg Arg Thr Gly Thr Thr Leu Cys Thr Leu Leu Gly Val Met
                275                 280                 285

Ala Thr Tyr Leu Leu Lys Gln Pro Pro Leu Pro Gln Asp Thr Ala His
            290                 295                 300

Pro Leu Arg Ala Ala Tyr Val Ile Pro Phe Thr Glu Gly Ala Thr Glu
305                 310                 315                 320

Phe Ser Lys Arg Phe Gly Val Pro Val Arg Ala Leu Phe Asn Met Thr
                325                 330                 335

Glu Val Ser Cys Pro Val Leu Ser Ala Pro Asp His His Pro Gly Val
                340                 345                 350

Pro Met His Cys Gly Glu Pro Arg Pro Gly Ile Ala Ala Arg Val Val
            355                 360                 365

Asp Asp His Asp Arg Glu Val Ala Asp Gly Glu Ala Gly Glu Leu Val
            370                 375                 380

Leu Arg Ala Asp Arg Pro Trp Ser Phe Leu Ser Gly Tyr Leu Gly Arg
385                 390                 395                 400

Pro Ala Glu Thr Ala Ala Val Trp Arg Asn Gly Trp Phe His Thr Gly
                405                 410                 415

Asp Thr Phe Arg Arg Ala Pro Asp Gly Gly Leu Val Phe Val Asp Arg
                420                 425                 430

Lys Lys Asp Ala Ile Arg Arg Gly Glu Asn Ile Ser Ser Phe Glu
            435                 440                 445

Val Glu Ala Gln Ala Val Ala His Pro Gly Val Leu Glu Ala Ala Ala
            450                 455                 460

Val Ala Val Pro Gly Asp Glu Gly Asp Glu Val Leu Leu Val Val
465                 470                 475                 480

Ala Asp Arg Asp Pro Ser Ala Pro Val Asp Pro Ala Ala Leu Leu Glu
                485                 490                 495
```

```
Phe Leu Arg Glu Arg Leu Ala His Phe Met Leu Pro Arg Tyr Ile Arg
            500                 505                 510

Val Leu Pro Glu Leu Pro Lys Thr Pro Thr Gly Lys Pro Thr Lys His
            515                 520                 525

Thr Leu Arg Ala Glu Gly Val Val Ala Gly Thr Trp Asp Arg Glu Ala
            530                 535                 540

Ala Gly Ile Arg Ile Arg Arg Glu Lys Ile Val
545                 550                 555
```